US006528066B1

(12) United States Patent
Grose et al.

(10) Patent No.: US 6,528,066 B1
(45) Date of Patent: Mar. 4, 2003

(54) VARIANT VARICELLA-ZOSTER VIRUSES AND METHODS OF USE

(75) Inventors: Charles F. Grose, Iowa City, IA (US); Richard Santos, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 47 days.

(21) Appl. No.: 09/661,596

(22) Filed: Sep. 14, 2000

Related U.S. Application Data

(60) Provisional application No. 60/153,779, filed on Sep. 14, 1999.

(51) Int. Cl.[7] .................. A61K 39/245; A61K 39/12
(52) U.S. Cl. .................. 424/229.1; 424/230.1; 424/204.1; 435/91.1; 435/91.33; 435/89; 536/23.72
(58) Field of Search .................. 435/89, 91.1, 91.33; 424/229.1, 230.1, 204.1; 536/23.72

(56) References Cited

U.S. PATENT DOCUMENTS

| | | | |
|---|---|---|---|
| 3,985,615 A | 10/1976 | Kubo | |
| 5,462,734 A | 10/1995 | Letchworth, III et al. | |
| 5,595,890 A | 1/1997 | Newton et al. | |
| 5,849,476 A | 12/1998 | Shiraki et al. | |
| 5,952,174 A | 9/1999 | Nikiforov et al. | |
| 6,087,170 A | * 7/2000 | Kemble | .......... 435/368 |

OTHER PUBLICATIONS

A. M. Arvin et al., "Live Attenuated Varicella Vaccine," *Annu. Rev. Microbiol.*, 50, 59–100 (1996).

A. M. Arvin et al., "Immunity to Varicella–Zoster Viral Glycoproteins, gp I (gp 90/58) and gp III (gp 118), and to a Nonglycosylated Protein, p. 170," *J. Immunol.*, 137, 1346–1351 (1986).

ATCC CCL–171, "*Homo sapiens* (human)," [online]. Retrieved on May 16, 2001. Retrieved from the Internet:<URL: http://phage.atcc.org/cgi–bin/searchengine/longview.cgi?view=ce, 317407, CCL–171&text=CCL.–.1,3 pages.

ATCC VR–568, "Varicella–Zoster," [online]. Retrieved on Jun. 5, 2001. Retrieved from the Internet:<URL: http://phage.atcc.org/cgi–bin/searchengine/longview.cgi?view=av,343894, VR–586&text=VR–586>, 2 pages.

ATCC VR–795, "Varicella–Zoster deposited as Varicella," [online]. Retrieved on May 16, 2001. Retrieved from the Internet:<URL: http://phage.atcc.org/cgi–bin/searchengine/longview.cgi?view=av,476976, VR–795&text=VR–7.9>, 2 pages.

ATCC VRL–1367, "Varicella–Zoster," [online]. Retrieved on Jun. 5, 2001. Retrieved from the Internet:<URL: http://phage.atcc.org/cgi–bin/searchengine/longview.cgi?view=av,871705, VR–1367&text=VR–1367>, 2 pages.

M. F. Bachman et al., "The influence of Antigen Organization on B Cell Responsiveness," *Science*, 262, 1448–1451 (1993).

R. E. Bergen et al., "Human T Cells Recognize Multiple Epitopes of an Immediate Early/Tegument Protein (IE62) and Glycoprotein I of Varicella Zoster Virus," *Viral Immunol.*, 4, 151–166 (1991).

J.I. Cohen et al., "Generation of varicella–zoster virus (VZV) and viral mutants from cosmid DNAs: VZV thymidylate synthetase is not essential for replication in vitro," *Proc. Natl. Acad. Sci. USA*, 90, 7376–7380 (1993).

N. L. Cole et al., "Colchicine treatment in the preparation of varicella–zoster virus inocula," *J. Virol. Methods*, 36, 111–118 (1992).

A.J. Davison et al., "The Complete DNA Sequence of Varicella–Zoster Virus," *J. Gen. Virol.*, 67, 1759–1816 (1986).

K. S. Dingwell et al., "Herpes simplex virus glycoproteins E and I facilitate cell–to–cell spread in vivo across junctions of cultured cells," *J. Virol.*, 68 834–845 (1994).

K. M. Duus et al., "Cell Surface Expression and Fusion by the Varicella–Zoster Virus gH:gL Glycoprotein Complex: Analysis by Laser Scanning Confocal Microscopy," *Virology*, 210, 429–440 (1995).

K. M. Duus et al., "Multiple Regulatory Effects of Varicella–Zoster Virus (VZV) gL on Trafficking Patterns and Fusogenic Properties of VZV gH," *J. Virol.*, 70, 8961–8971 (1996).

J. R. Ecker et al., "Varicella zoster virus DNA exists as two isomers," *Proc. Natl. Acad. Sci. USA*, 79, 156–160 (1982).

Frank et al., "Brainvox: An Interactive, Multimodal Visualization and Analysis System for Neuroanatomical Imaging," *Neuroimage*, 5, 13–30 (1997).

T. Gojobori et al., "Rates of evolution of the retroviral oncogene of Maloney murine sarcoma virus and of its cellular homologues," *Proc. Natl. Acad. Sci. USA*, 82, 4198–4201 (1985).

P. R. Kinchington et al., "Regulated Nuclear Localization of the Varicella–Zoster Virus Major Regulatory Protein, IE62," *J. Infect. Dis.*, 178(Suppl. 1), S16–21 (1998).

(List continued on next page.)

Primary Examiner—Ali R. Salimi
(74) Attorney, Agent, or Firm—Mueting, Raasch & Gebhardt, P.A.

(57) ABSTRACT

The present invention provides methods directed to detecting antibodies that specifically bind to a varicella zoster polypeptide, detecting the presence of a varicella zoster virus in an animal, diagnosing a disease caused by varicella zoster virus, and detecting a varicella zoster virus having a single nucleotide polymorphism in ORF68. The present invention also provides a vaccine composition, a method for producing a modified attenuated varicella zoster virus, isolated polynucleotides, and isolated polypeptides, and viruses.

3 Claims, 10 Drawing Sheets

OTHER PUBLICATIONS

Figure 2:
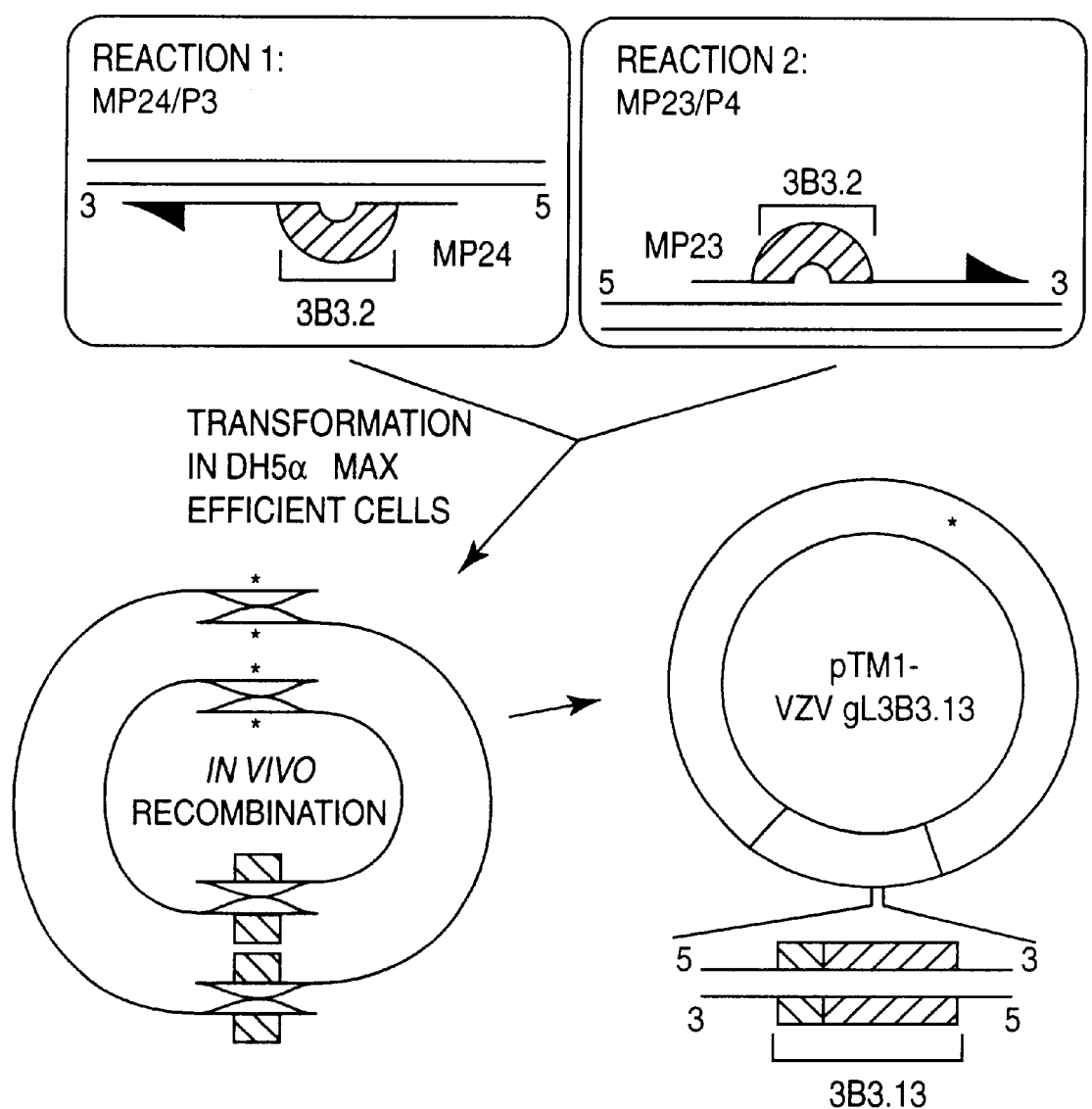

P. R. Kinchington et al., "Molecular basis for a geographic variation of varicella–zoster virus recognized by a peptide antibody," *Neurology, 45* (Suppl 8), S13–14 (1995).

P. LaRussa et al., "Restriction fragment length polymorphism of polymerase chain reaction products from vaccine and wild–type varicella–zoster virus isolates," *J. Virol., 66,* 1016–1020 (1992).

V. Litwin et al., "Receptor Properties of Two Varicella–Zoster Virus Glycoproteins, gpI and gpIV, Homologous to Herpes Simplex Virus gE and gI," *J. Virol., 66,* 3643–3651 (1992).

V. Litwin et al., "Cell Surface Expression of the Varicella–Zoster Virus Glycoproteins and Fc Receptor," *Virology, 178,* 263–272 (1990).

S. Mallory et al., "Mutational Analysis of the Role of Glycoprotein I in Varicella–Zoster Virus Replication and Its Effects on Glycoprotein E Conformation and Trafficking," *J. Virol., 71,* 8279–8288 (1997).

D. J. McGeoch et al., "Molecular phylogeny of the alpha-herpesvirinae subfamily and a proposed evolutionary timescale," *J. Mol. Biol., 238,* 9–22 (1994).

D. J. McGeoch et al., "Molecular phylogeny and evolutionary timescale for the family of mammalian herpesviruses," *J. Mol. Biol., 257,* 443–458 (1995).

J. F. Moffat et al., "Tropism of Varicella–Zoster Virus for Human $CD4^+$ and $CD8^+$ T Lymphocytes and Epidermal Cells in SCID–hu Mice," *J. Virol., 69,* 5236–5242 (1995).

J. F. Moffat et al., "Attenuation of the Vaccine Oka Strain of Varicella–Zoster Virus and Role of Glycoprotein C in Alphaherpesvirus Virulence Demonstrated in the SCID–hu Mouse," *J. Virol., 72,* 965–974 (1998).

E. A. Montalvo et al., "Assembly and Processing of the Disulfide–Linked Varicella–Zoster Virus Glycoprotein gpII(140)," *J. Virol., 61,* 2877–2884 (1987).

National Center for Biotechnology Information, National Library of Medicine, National Institutes of Health, Genbank X04370. Accession No. X04370 M14891 M16612, "The complete DNA sequence of varicella–zoster virus," [online]. *J. Gen. Virol.,* 67 (Pt 9) 1759–1816 (1986), [retrieved on May 29, 2001]. Retrieved from the Internet:<URL: http://www.ncbi.nlm.nih.gov/entrez/query.fcgi?cmd=Retrieve&db=Nucleotide&list_uids=599.8=GenBank>, 39 pages.

T. I. Ng et al., "Phosphorylation of Varicella–Zoster Virus Open Reading Frame (ORF) 62 Regulatory Product by Viral ORF 47–Associated Protein Kinase," *J. Virol., 68,* 1350–1359 (1994).

N. Nishimura et al., "A Di–Acidic Signal Required for Selective Export from the Endoplasmic Reticulum", *Science, 277,* 556–560 (1997).

J. K. Olson et al., "Complex formation facilitates endocytosis of the varicella–zoster virus gE:gI Fc receptor," *J. Virol., 72,* 1542–1551 (1998).

J. K. Olson et al., "Varicella–Zoster Virus Fc Receptor gE Glycoprotein: Serine/Threonine and Tyrosine Phosphorylation of Monomeric and Dimeric Forms," *J. Virol., 71,* 110–119 (1997).

J. K. Olson et al., "Endocytosis and Recycling of Varicella–Zoster Virus Fc Receptor Glycoprotein gE: Internalization Mediated by a YXXL Motif in the Cytoplasmic Tail," *J. Virol., 71,* 4042–4054 (1992).

J. A. Padilla et al, "High–resolution immuno–scanning electron microscopy using a non–coating method: study of herpes simplex virus glycoproteins on the surface of virus particles and infected cells," *J. Elect. Microscopy, 46,* 171–180 (1997).

B. Rentier, "Introduction", *Neurol., 45*(Suppl 8), S8 (1995).

J. E. Rodriguez et al., "Entry and egress of varicella virus blocked by same anti–gH monoclonal antibody," *Virology, 196,* 840–844 (1993).

J. Sambrook et al, *Molecular Cloning: A Laboratory Manual., Second Edition,* Cold Spring Harbor Laboratory Press (1989), (Cover Page, publication page and table of contents).

R. A. Santos et al., "Varicella–Zoster Virus gE Escape Mutant VZV–MSP Exhibits an Accelerated Cell–to–Cell Spread Phenotype in both Infected Cell Cultures and SCID–hu Mice," *Virology, 275,* 306–317 (Sep., 2000).

R. A. Santos et al., "Antigenic Variation of Varicella Zoster Virus Fc Receptor gE: Loss of a Major B Cell Epitope in the Ectodomain," *Virology, 249,* 21–31 (1998).

T. Shioda et al., "Small amino acid changes in V3 hypervariable region of gp120 can affect the T–cell–line and macrophage tropism of human immunodeficiency virus type 1," *Proc. Natl. Acad. Sci. USA, 89,* 9434–9438 (1992).

F. I. Smith et al., "Variation in influenza virus genes epidemiological, pathogenic and evolutionary consequences", *The Influenza Virues,* (R.M. Krug, Ed.), 319–359. Plenum Press, New York (1989).

P. G. Spear, "Glycoproteins Specified by Herpes Simplex Viruses," *The Herpesviruses, 3,* (B. Roizman, Ed.), 315–356, Plenum Press, New York (1985).

E. Szomolanyi–Tsuda et al., "T cell–independent antibody–mediated clearance of polyoma virus in T cell–deficient mice," *J. Exp. Med., 183,* 403–411 (1996).

M. Takahashi et al., "Development of a Live Attenuated Varicella Vaccine," *Biken J., 18,* 25–33 (1975).

T. A. Tatusova, et al. "Blast 2 Sequences, a new tool for comparing protein and nucleotide sequences," *FEMS Microbiol Lett, 174,* 247–250 (1999), and available at http://www.ncbi.nlm.nih.gov/gorf/bl2.html.

U.S. National Institutes of Health, "About NIH Image," [online]. Retrieved on May 29, 2001. Retrieved from the Internet:<URL: http://rsb.info.nih.gov/nih–image/about.html, 2 pages.

K. A. Weigle et al., "Common expression of varicella–zoster virual glycoprotein antigens in vitro and in chickenpox and zoster vesicles," *J. Infect. Dis., 148,* 630–638 (1983).

T. H. Weller, "Serial propagation in vitro of agents producing inclusion bodies derived from varicella and herpes zoster," *Proc. Soc. Exp. Biol. Med., 83,* 340–346 (1953).

S. A. Wharton et al., "Structure, function, and antigenicity of the hemagglutinin of influenza viruses," *The Influenza Viruses,* (R. M. Krug. Ed.), 153–171. Plenum Press, New York (1989).

M. Yang et al., "Retrograde, Transneuronal Spread of Pseudorabies Virus in Defined Neuronal Circuitry of the Rat Brain is Facilitated by gE Mutations that Reduce Virulence," *J. Virol., 73,* 4350–4359 (May, 1999).

Z. Yao et al., "Varicella–Zoster Virus Glycoprotein gpI/gpIV Receptor: Expression, Complex Formation, and Antigenicity within the Vaccinia Virus–T7 RNA polymerase Transfection System," *J. Virol., 67,* 305–314 (1993).

Z. Zhu et al, "Targeting of glycoprotein I (GE) of varicella–zoster virus to the trans–Golgi network by an AyRV sequence and an acidic amino acid–rich patch in the cytosolic domain of the molecule," *J. Virol.*, *70*, 6563–6575 (1996).

Z. Zhu et al., "Envelopment of varicella–zoster virus: targeting of viral glycoproteins to the trans–Golgi network," *J. Virol.*, *69* 7951–7959 (1995).

F. L. Graham et al., "Characteristics of a Human Cell Line Transformed by DNA from Human Adenovirus Type 5," *J. Gen. Virol.*, *36*, 59–74 (1977).

C. Grose et al., "Computer modeling of prototypic and aberrant nucleocapsids of varicella–zoster virus," *Virology*, *214*, 321–329 (1995).

C. Grose, "Glycoproteins Encoded by Varicella–Zoster Virus: Biosynthesis, Phosphorylation, and Intracellular Trafficking," *Annu.Rev. Microbiol.*, *44*, 59–80 (1990).

C. Grose, "Pathogenesis of Infection with Varicella Vaccine," *Infect. Dis. Clinics NA*, *10*, 489–505 (1996).

C. Grose et al., "Varicella–Zoster Virus: Isolation and Propagation in Human Melanoma Cells at 36 and 32° C.," *Infect. Immun.*, *19*, 199–203 (1978).

C. Grose et al., "Monoclonal Antibodies Against Three Major Glycoproteins of Varicella–Zoster Virus," *Infect. Immun.*, *'*, 381–388 (1983).

C. Grose, "The Synthesis of Glycoproteins in Human Melanoma Cells Infected with Varicella–Zoster Virus," *Virology*, *101*: 1–9 (1980).

B. H. Hahn et al., "Genetic variation in HTLV–III/LAV over time in patients with AIDS or at risk for AIDS," *Science*, *232*, 1548–1553 (1986).

R. Harson et al., "Egress of Varicella–Zoster Virus from the Melanoma Cell: a Tropism for the Melanocyte," *J. Virol.*, *69*, 4994–5010 (1995).

C. Hatfield et al., "Epitope Mapping and Tagging by Recombination PCR Mutagenesis," *BioTechniques*, *22*, 332–337 (1997).

J. Holland et al., "Rapid evolution of RNA genomes,"*Science*, *215*, 1577–1585 (1982).

M. Ito et al., "Human Leukocytes Kill Varicella–Zoster Virus–Infected Fibroblasts in the Presence of Murine Monoclonal Antibodies to Virus–Specific Glycoproteins," *J. Virol.*, *54*, 98–103 (1985).

D. H. Jones et al., "A Rapid Method for Site–Specific Mutagenesis and Directional Subcloning by Using the Polymerase Chain Reaction to Generate Recombinant Circles," *BioTechniques*, *8*, 178–183 (1990).

F. Jones et al., "Role of cytoplasmic vacuoles in varicella–zoster virus glycoprotein trafficking and virion envelopment," *J. Virol.*, *62*, 2701–2711 (1988).

P. R. Kinchington et al., "Regulated Nuclear Localization of the Varicella–Zoster Virus Major Regulatory Protein, IE62, " *J. Infect. Dis.*, *178*(Suppl. 1), S16–21 (1998).

P. R. Kinchington et al., "Molecular basis for a geographic variation of varicella–zoster virus recognized by a peptide antibody," *Neurology*, *45 (Suppl 8)*, S16–21 (1995).

P. LaRussa et al., "Restriction fragment length polymorphism of polymerase chain reaction products from vaccine and wild–type varicella–zoster virus isolates," *J. Virol.*, *66*, 1016–1020 (1992).

V. Litwin et al., "Receptor Properties of Two Varicella–Zoster Virus Glycoproteins, gpI and gpIV, Homologous to Herpes Simplex Virus gE and gI," *J. Virol.*, *66*, 3643–3651 (1992).

V. Litwin et al., "Cell Surface Expression of the Varicella–Zoster Virus Glycoproteins and Fc Receptor," *Virology*, *178*, 263–272 (1990).

S. Mallory et al., "Mutational Analysis of the Role of Glycoprotein E Confirmation and Trafficking, " *J. Virol.*, *71*, 8279–8288 (1997).

D. J. McGeoch et al., "Molecular phylogeny of the alphaherpesvirinae subfamily and a proposed evolutionary timescale," *J. Mol. Biol.*, *238*, 9–22 (1994).

D. J. McGeoch et al., "Molecular phylogeny and evolutionary timescale for the family of mammalian herpesviruses," *J. Mol. Biol.*, *247*, 443–458 (1995).

J. F. Moffat et al., "Tropism of Varicella–Zoster Virus for Human CD4$^+$ and CD8$^{+T}$ *Lymphocytes and Epidermal Cells in SCID–hu Mice*," *J. Virol.*, *69*, 5236–5242 (1995).

J. F. Moffat et al., "Attenuation of the Vaccine Oka Strain of Varicella–Zoster Virus and Role of Glycoprotein C in Alphaherpesvirus Virulence Demonstrated in the SCID–hu Mouse," *J. Virol.* , *72*, 965–974 (1998).

E. A, Montalvo et al., "Assembly and Processing of the Disulfide–Linked Varicella–Zoster Virus Glycoprotein gpII(140)," *J. Virol.*, *61*, 2877–2884 (1987).

National Center for Biotechnology Information, National Library of Medicine, National Institutes of Health, Genbank X04370. Accession Number X04370 M14891 M16612, "The complete DNA sequence of varicella–zoster virus," [online]. J. Gen. Virol., 67 (Pt 9) 1759–1816 (1986), [retrieved on May 29, 2001]. Retrieved from the Internet:<URL: http://www.ncbi.nlm.nih.gov/entrez/query-.fcgi?cmd=Retrieve&db=Nucleotide&list_uids=599.8=GenBank≦, 39 pages.

T. I. Ng et al., "Phosphorylation of Varicella–Zoster Virus Open Reading Frame (ORF) 62 Regulatory Product by Viral ORF 47–Associated Protein Kinase," *J. Virol.*, *68*, 1350–1359 (1994).

N. Nishimura et al., "A Di–Acidic Signal Required for Selective Export from the Endoplasmic Reticulum", *Science*, *277*, 556–560 (1997).

J. K. Olson et al., "Complex formation facilitates endocytosis of the varicella–zoster virus gE:gI Fc receptor," *J. Virol.*, *72*, 1542–1551 (1998).

J. K. Olson et al., "Varicella–Zoster Virus Fc Receptor gE Glycoprotein: Serine/Threonine and Tyrosine Phosphorylation of Monomeric and Dimeric Forms," *J. Virol.*, *71*, 110–119 ;(1997).

J. K. Olson et al., "Endocytosis and Recycling of Varicella–Zoster Virus Fc Receptor Glycoprotein gE: Internalization Mediated by a YXXL Motif in the Cytoplasmic Tail," *J. Virol.*, *71*, 4042–4054 (1992).

J. A. Padilla et al, "High–resolution immuno–scanning electron microscopy using a non–coating method: study of herpes simplex virus glycoproteins on the surface of virus particles and infected cells," *J. Elect. Microscopy*, *46*, 171–180 (1997).

B. Rentier, "Introduction", *Neurol.*, *45(Suppl. 8)*, S8 (1995).

J. E. Rodriguez et al., "Entry and egress of varicella virus blocked by same anti–gH monoclonal antibody," *Virology*, *196*, 840–844 (1993).

J. Sambrook et al, *Molecular Cloning: A Laboratory Manual.*, *Second Edition*, Cold Spring Harbor Laboratory Press (1989), (Cover Page, publication page and table of contents).

R. A. Santos et al., "Varicella–Zoster Virus gE Escape Mutant VZV–MSP Exhibits and Accelerated Cell–to–Cell Spread Phenotype in both Infected Cell Cultures and SCID–hu Mice," *Virology*, 275, 306–317 (Sep., 2000).

R. A. Santos et al., "Antigenic Variation of Varicella Zoster Virus Fc Receptor gE: Loss of a Major B Cell Epitope in the Ectodomain," *Virology*, 249, 21–31 (1998).

T. Shioda et al., "Small amino acid changes in V3 hypervariable region of gp120 can affect the T–cell–line and macrophage tropism of human immunodeficiency virus type 1," *Proc. Natl. Acad. Sci. USA*, 89, 9434–9438 (1992).

F. I. Smith et al., "Variation in influenza virus genes epidemiological, pathogenic, and evolutionary consequences", *The Influenza Virues*, (R.M. Krug. Ed.), 319–359. Plenum Press, New York (1989).

P. G. Spear, "Glycoproteins Specified by Herpes Simplex Viruses," *The Herpesviruses, 3*, (B. Roizman, Ed.). 315–356. Plenum Press, New York (1985).

E. Szomolanyi–Tsuda et al., "T cell–independent antibody–mediated clearance of polyoma virus in T cell–deficient mice," *J. Exp. Med.*, 183, 403–411 (1996).

M. Takahashi et al., "Development of a Live Attenuated Varicella Vaccine," *Biken J.*, 18, 25–33 (1975).

T. A. Tatusova, et al., "BLAST 2 SEQUENCES, a new tool for comparing protein and necleotide sequences," *FEMS Microbial Lett*, 174, 247–250 (1999), and available at http://www.ncbi.nlm.nih.gov/gorf/b12.html.

U.S. National Institutes of Health, "About NIH Image," [online]. Retrieved on May 29, 2001. Retrieved from the Internet:>URL: http://rsb.info.nih.gov/nih–image/about.html, 2 pages.

K. A. Weigle et al., "Common expression of varicella–zoster viral glycoprotein antigens in vitro and in chickenpox and zoster vesicles," *J. Infect. Dis.*, 148, 630–638 (1983).

T. H. Weller, "Serial propagation in vitro of agents producing inclusion bodies derived from varicella and herpes zoster," *Proc. Soc. Exp. Biol. Med.*, 83340–346 (1953).

S. A. Wharton et al., "Structure, function, and antigenicity of the hemagglutinin of influenza viruses," *The Influenza Viruses*, (R. M. Krug. Ed.), 153–171. Plenum Press, New York (1989).

M. Yang et al., "Retrograde, Transneuronal Spread of Pseudorabies Virus in Defined Neuronal Circuitry of the Rat Brain is Facilitated by gE Mutations that Reduce Virulence," *J. Virol.*, 73, 4350–4359 (May, 1999).

Z. Yao et al., "Varicella–Zoster Virus Glycoprotein gpI/gpIV Receptor: Expression, Complex Formation, and Antigenicity within the Vaccinia Virus–T7 RNA polymerase Transfection System," *J. Virol.*, 67, 305–314 (1993).

Z. Zhu et al., "Targeting of glycoprotein I (gE) of varicella–zoster virus to the trans–Golgi network by an AYRV sequence and an acidic amino acid–rich patch in the cytosolic domain of the molecule," *J. Virol.*, 70, 6563–6575 (1996).

Z. Zhu et al., "Envelopment of varicella–zoster virus: targeting of viral glycoproteins to the trans–Golgi network," *J. Virol.*, 69 7951–7959 (1995).

\* cited by examiner

*Fig. 1A*

(SEQ ID NO:72)

```
  1 MGTVNKPVVG VLMGFGIITG TLRITNPVRA SVLRYDDFHT DEDKLDTNSV
 51 YEPYYHSDHA ESSWVNRGES SRKAYDHNSP YIWPRNDYDG FLENAHEHHG
101 VYNQGRGIDS GERLMQPTQM SAQEDLGDDT GIHVIPTLNG DDRHKIVNVD
151 QRQYGDVFKG DLNPKPQGQR LIEVSVEENH PFTLRAPIQR IYGVRYTETW
201 SFLPSLTCTG DAAPAIQHIC LKHTTCFQDV VVDVDCAENT KEDQLAEISY
251 RFQGKKEADQ PWIVVNTSTL FDELELDPPE IEPGVLKVLR TEKQYLGVYI
301 WNMRGSDGTS TYATFLVTWK GDEKTRNPTP AVTPQPRGAE FHMWNYHSHV
```

*Fig. 1B*

```
                              3B3.13
            3B3.2                   3B3.11
            V   D   Q   R   Q   Y   G   D   V   F   K   G   D    (SEQ ID NO:73)
VZVgE       GTG GAC CAA CGT CAA TAC GGT GAC GTG TTT AAA GGA GAT  (SEQ ID NO:74)
(149-161)
                N
VZVgE-
D150N       GTG AAC CAA CGT CAA TAC GGT GAC GTG TTT AAA GGA GAT  (SEQ ID NO:75)
(149-161)
```

Fig. 6

Polymorphisms in gE

| bp | 119 | 448 | 660 | 1606 | 1808 |
|---|---|---|---|---|---|
| aa | T>I | D>N | silent | L>I | G>D |
|  | * | * | * | * | * |

| | | | | | |
|---|---|---|---|---|---|
| Dumas | —CACACCGAT-/-GTGGACCAA-/-ATATGTTTA-/-CTTCTACGA-/-TTTGGTAAC— |
| MSP | —CACACCGAT-/-GTGAACCAA-/-ATATGTTTA-/-CTTCTACGA-/-TTTGGTAAC— |
| Ellen | —CACATCGAT-/-GTGGACCAA-/-ATATGCTTA-/-CTTATACGA-/-TTTGGTAAC— |
| Iceland | —CACATCGAT-/-GTGGACCAA-/-ATATGCTTA-/-CTTATACGA-/-TTTGGTAAC— |
| 80-2 | —CACATCGAT-/-GTGGACCAA-/-ATATGCTTA-/-CTTATACGA-/-TTTGGTAAC— |
| Oka | —CACATCGAT-/-GTGGACCAA-/-ATATGTTTA-/-CTTCTACGA-/-TTTGGTAAC— |
| VSD | —CACACCGAT-/-GTGGACCAA-/-ATATGTTTA-/-CTTCTACGA-/-TTTGATAAC— |
| 32 | —CACACCGAT-/-GTGGACCAA-/-ATATGTTTA-/-CTTCTACGA-/-TTTGGTAAC— |
| VIA | —CACACCGAT-/-GTGGACCAA-/-ATATGTTTA-/-CTTCTACGA-/-TTTGGTAAC— |

Fig. 7

Polymorphisms in g1

| | bp | 15 | 546 |
|---|---|---|---|
| | aa | 5 Q>H | silent |
| Dumas | —ATCCAATGT -/- TCTCCGTCT— | | |
| MSP | —ATCCAATGT -/- TCTCCGTCT— | | |
| Ellen | —ATCCAATGT -/- TCTCCGTCT— | | |
| Iceland | —ATCCAATGT -/- TCTCCGTCT— | | |
| 80-2 | —ATCCAATGT -/- TCTCCGTCT— | | |
| Oka | —ATCCAATGT -/- TCTCC<u>A</u>TCT— | | |
| VSD | —ATCCAATGT -/- TCTCCGTCT— | | |
| 32 | —ATCCA<u>C</u>TGT -/- TCTCCGTCT— | | |
| VIA | —ATCCA<u>C</u>TGT -/- TCTCCGTCT— | | |

Fig. 8

Polymorphisms in gH

| bp<br>aa | 39<br>silent | 215<br>76 R>K | 573<br>silent | 806<br>269 P>L | 1254<br>silent |
|---|---|---|---|---|---|
| Dumas | CCTCTTTGG -/- GATAGAAAA | -/- ATTCTGGAA | -/- GGACCACCG | -/- AACACTATA | |
| MSP | CCTCTGTGG -/- GATAGAAAAA | -/- ATTCTGGAA | -/- GGACTACCG | -/- AACACTATA | |
| Ellen | CCTCTGTGG -/- GATAAAAAA | -/- ATTCTGGAA | -/- GGACTACCG | -/- AACACGATA | |
| Iceland | CCTCTGTGG -/- GATAAAAAA | -/- ATTCTGGAA | -/- GGACTACCG | -/- AACACTATA | |
| 80-2 | CCTCTGTGG -/- GATAAAAAA | -/- ATTCTGGAA | -/- GGACTACCG | -/- AACACTATA | |
| Oka | CCTCTTTGG -/- GATAGAAAA | -/- ATTCTTGAA | -/- GGACTACCG | -/- AACACTATA | |
| VSD | CCTCTTTGG -/- GATAGAAAA | -/- ATTCTGGAA | -/- GGACCACCG | -/- AACACTATA | |
| 32 | CCTCTTTGG -/- GATAGAAAA | -/- ATTCTGGAA | -/- GGACTACCG | -/- AACACTATA | |
| VIA | CCTCTTTGG -/- GATAGAAAA | -/- ATTCTGGAA | -/- GGACTACCG | -/- AACACTATA | |

| bp<br>aa | 2028<br>silent | 2099<br>700 R>K | 2181<br>silent | 2445<br>silent |
|---|---|---|---|---|
| Dumas | AAACCCTCAA -/- AGCAGGGAT | -/- TATTGCGGA | -/- CTGGCGGTA | |
| MSP | AAACCCTCAA -/- AGCAGGGAT | -/- TATTGCGGA | -/- CTGGCGGTA | |
| Ellen | AAACCCCAA -/- AGCAGAGAT | -/- TATTGTTGGA | -/- CTGGCGGTA | |
| Iceland | AAACCCCAA -/- AGCAGAGAT | -/- TATTGTTGGA | -/- CTGGCGGTA | |
| 80-2 | AAACCCCAA -/- AGCAGAGAT | -/- TATTGTTGGA | -/- CTGGCGGTA | |
| Oka | AAACCCTCAA -/- AGCAGGGAT | -/- TATTGCGGA | -/- CTGGCGGTA | |
| VSD | AAACCCTCAA -/- AGCAGGGAT | -/- TATTGCGGA | -/- CTGGCGGTA | |
| 32 | AAACCCTCAA -/- AGCAGGGAT | -/- TATTGCGGA | -/- CTGGCAGTA | |
| VIA | AAACCCTCAA -/- AGCAGGGAT | -/- TATTGCGGA | -/- CTGGCAGTA | |

*Fig. 9*

Polymorphisms in gL

```
Dumas
aa   8   9   10  11                      106 107 108
   —CTG CAG ATA GTT——||————————————————GTT GGT GAA—
     L   Q   I   V                       V   G   E
```
(SEQ ID NO:77)
(SEQ ID NO:78)

```
Oka
aa   8   9   10                          106 107 108
   —CTG CAG ATG ATA——||————————————————GTT GAT GAA—
     L   Q   M   I                       V   D   E
```
(SEQ ID NO:79)
(SEQ ID NO:80)

Fig. 10

Polymorphisms in IE62

| AA | 30 | 42 | 61 | 129 | 131 | 172 | 190 | 195 | 341 | 473 | 516 | 602 | 609 | 628 | 657 | 688 | 703 | 743 | 879 | 958 |
|---|---|---|---|---|---|---|---|---|---|---|---|---|---|---|---|---|---|---|---|---|
|   | * | S>A | * | * | * | * | * | N>D | * | * | * | A>V | * | S>G | A>T | * | V>A | * | * | R>G |
| Dumas | GCG | TCG | CAC | CTT | ACA | GTT | CAA | AAT | CCA | GCA | GTG | GCG | CGA | AGC | GCT | CCA | GTC | CTT | GGA | AGG |
| MSP | GCC | --- | --- | --- | --- | --- | --- | --- | --- | --- | --- | --- | --- | --- | --- | --- | --- | --- | --- | --- |
| Ellen | GCC | --- | CAT | CTC | ACG | GTC | CAG | GAT | CCG | --- | --- | --- | --- | --- | --- | --- | --- | --- | --- | GGG |
| Iceland | GCC | GCG | CAT | CTC | --- | --- | --- | --- | --- | --- | --- | --- | --- | --- | --- | --- | --- | --- | --- | --- |
| 80-2 | GCC | --- | CAT | CTC | --- | --- | --- | --- | CCG | GCG | GTA | --- | --- | GGC | --- | --- | GCC | --- | --- | --- |
| OKA | GCC | --- | CAT | CTC | --- | --- | --- | --- | CCG | --- | GTA | GTG | --- | --- | ACT | CCG | GCC | --- | --- | --- |
| VSD | GCC | --- | --- | --- | --- | --- | --- | --- | --- | --- | --- | --- | --- | --- | ACT | --- | GCC | --- | --- | --- |
| 32 | GCC | --- | --- | --- | --- | --- | --- | --- | --- | --- | --- | --- | --- | --- | --- | --- | --- | --- | GGG | GGG |
| VIA | GCC | --- | --- | --- | --- | --- | --- | --- | --- | --- | --- | --- | --- | --- | --- | --- | --- | CTC | --- | GGG |

| AA | 963 | 1035 | 1057 | 1071 | 1072 | 1080 | 1093 | 1143 | 1145 | 1201 | 1208 | 1208 | 1215 | 1228 | 1241 | 1243 | 1255 | 1260 |
|---|---|---|---|---|---|---|---|---|---|---|---|---|---|---|---|---|---|---|
|   | * | S>A | * | * | Q>R | * | * | * | * | H>R | S>A | * | Q>R | L>P | S>G | E>G | S>A | I>V |
| Dumas | TTG | GCA | CAG | CGA | CAG | GCA | GCA | GCA | CCA | CAC | TCA | TCA | CAG | CTG | AGC | GAG | TCC | ATC |
| MSP | --- | --- | --- | --- | --- | --- | --- | --- | --- | --- | --- | --- | --- | --- | --- | --- | --- | --- |
| Ellen | CTG | --- | --- | --- | --- | --- | GCG | --- | --- | --- | --- | --- | --- | --- | --- | --- | --- | --- |
| Iceland | --- | --- | --- | AGA | --- | --- | --- | --- | --- | --- | --- | --- | --- | --- | --- | --- | --- | --- |
| 80-2 | --- | --- | --- | AGA | --- | --- | --- | --- | --- | --- | --- | --- | --- | --- | --- | GGG | GCC | --- |
| OKA | --- | --- | --- | AGA | --- | --- | --- | GCG | --- | --- | GCA | --- | --- | CCG | --- | --- | --- | --- |
| VSD | --- | --- | --- | --- | --- | --- | --- | --- | --- | --- | --- | TCG | --- | --- | --- | --- | --- | --- |
| 32 | --- | CGG | --- | --- | CGG | GCG | GCG | --- | CCG | CGC | --- | --- | CGG | --- | GGC | --- | --- | --- |
| VIA | --- | CGG | --- | --- | CGG | GCG | GCG | --- | CCG | --- | --- | --- | --- | --- | GGC | --- | --- | GTC |

VARIANT VARICELLA-ZOSTER VIRUSES AND METHODS OF USE

CONTINUING APPLICATION DATA

This application claims the benefit of U.S. Provisional Application Ser. No. 60/153,779, filed Sep. 14, 1999, which is incorporated by reference herein.

GOVERNMENT FUNDING

The present invention was made with government support under Grant No. AI 22795, awarded by the National Institutes of Health. The Government has certain rights in this invention.

BACKGROUND

Varicella-zoster virus (VZV) is an ancient virus. Estimations of its origins have established that the modem herpesviruses arose some 60–80 million years ago. VZV is a member of the alphaherpesvirus subfamily of herpesviridae. It is the etiologic agent of chickenpox in childhood, after which the virus enters a latent state in the dorsal root ganglia; decades later, the same virus reactivates and causes the disease shingles (herpes zoster). The entire sequence of the 125 kbp VZV genome has been published (see Davison et al., *J. Gen. Virol.*, 67:1759–1816 (1986)). With the subsequent publication of sequence data from other herpesviruses, the alphaherpesvimuses have now been subdivided into two genera called Simplexvirus and Varicellovirus. VZV is considered to have one of the most stable genomes of all herpesviruses. The Oka strain of varicella vaccine derived from a Japanese child with chickenpox has a few minor genomic differences from North American strains, but to date no antigenic variation has been discovered amongst the major surface immunogens of the virion (Arvin et al., *Annu. Rev. Microbiol.*, 50:59–100 (1996)).

Based on their extensive analyses of herpesviral molecular evolutionary history, it has been estimated that herpesvirus DNA sequences mutate 10–100 times faster than the equivalent classes of sequences on the host genome. For glycoprotein gB, a highly conserved open reading frame (ORF) among all herpesviruses, it has been calculated that nonsynonymous substitutions have occurred at a rate of $2.7 \times 10^{-8}$ substitutions per site per year and synonymous substitutions at $10^{-7}$ substitutions per site per year. Convincing arguments have been made in favor of the concept of cospeciation; in other words, herpesvirus lineages arise by way of co-evolution with their specific host. In the case of VZV, the progenitor virus most likely arose 60–70 million years before the present.

Of all the human herpesviruses, VZV may undergo the fewest replication cycles during the lifetime of the infected host. Based on a probable schema of pathogenesis, the virus actively replicates for a period of 10–14 days after infection of the human host. During a bout of chickenpox, therefore, VZV has at most 20 replication cycles. Based on the current understanding of VZV latency and reactivation, no further replication occurs unless the individual develops herpes zoster in late adulthood. Because of the above scenario, the genetic stability of the VZV genome has been presumed.

VZV contains the smallest genome of the human herpesviruses, containing about 70 ORFs within the complete VZV-Dumas sequence. Of these ORFs, at least seven code for glycoproteins, of which glycoprotein B (gB), glycoprotein E (gE), glycoprotein H (gH), and glycoprotein I (gI) are present on the exterior of the virion. VZV gE, in complex with glycoprotein I (gI), acts as a human Fc receptor on the surface of infected cells (Litwin et al., *J. Virol.*, 66:3643–51 (1992), Litwin et al., *Virology*, 178:263–72 (1990)). The cytoplasmic tails of both gE and gI contain endocytosis motifs, allowing internalization and recycling of the complex to and from the cell (Olson et al., *J. Virol.*, 71:110–119 (1997), Olson et al., *J. Virol.*, 71:4042–4054 (1992)). The gE and gI cytoplasmic tails also are modified by both serine/threonine and tyrosine phosphorylation motifs. The fact that gE cannot be deleted suggests that it is essential (Cohen et al., *Proc. Natl. Acad. Sci. USA*, 90:7376–7380 (1993), Mallory et al., *J. Virol.*, 71:8279–88 (1997)).

In VZV infection in humans, VZV gE is the most abundantly produced viral glycoprotein during infection. VZV gE is a major antigenic determinant to which numerous humoral and cytolytic responses are observed (Arvin et al., *J. Immunol.*, 137:1346–1351 (1986); Bergen et al., *Viral Immunol.*, 4:151–166 (1991); and Ito et al., *J. Virol.*, 54:98–103 (1985)). Recently, an immunodominant B-cell epitope was demarcated in the gE ectodomain; the epitope is defined by murine monoclonal antibody (MAb) 3B3 (Duus et al., *J. Virol.*, 70:8961–8971 (1996); Hatfield et al., *BioTechniques* 22:332–337 (1997); and Grose, U.S. Pat. No. 5,710,348).

It has long been believed that varicella zoster virus exists in nature as a single serotype (Rentier, *Neurol.*, 45(Suppl. 8), S8 (1995), and that all varicella zoster viruses had essentially the same immunological properties. The first strain of varicella zoster virus that was sequenced was VZV-Dumas. Following the publication of this sequence, it was further believed that all varicella zoster viruses had essentially the same genetic properties as VZV-Dumas.

Significant progress has been made in the diagnosis of and vaccination against the sole VZV serotype that is believed to exist and cause disease in the United States. However, the production of the reagents used in diagnosis and vaccination of VZV is time consuming and expensive due to the slow growth rate of the strain grown to produce antigens for diagnostic and vaccine use.

SUMMARY OF THE INVENTION

The present invention represents a significant advance in the art of detecting and preventing varicella zoster virus infection and disease. During the characterization of a varicella zoster virus isolated from a patient, the surprising and unexpected observation was made that the virus had a different serotype. This strain was designated VZV-MSP. The molecular basis of the different serotype was found to be a single nucleotide polymorphism in the genome between VZV-Dumas and VZV-MSP. It was also determined that this single nucleotide polymorphism resulted in the loss of an epitope that is the epitope to which most protective antibody is produced upon vaccination with most currently used vaccines.

Typically, varicella zoster virus isolates can be divided into two groups with respect to growth rate in tissue culture cells. Some isolates, for instance VZV-Oka and VZV-Ellen, grow at a rate that results in complete lysis of a monolayer in about 5 to 7 days. Clinical isolates typically grow at a rate that results in complete lysis of a monolayer in about 4 to 5 days. Further investigation revealed that the new strain, VZV-MSP, unexpectedly and surprisingly had by in vitro tissue culture a growth rate that was significantly higher than previously characterized isolates, and was able to lyse a monolayer in about 2 days.

The present invention provides a method for detecting antibodies that specifically bind to a varicella zoster polypeptide. A biological sample that includes an antibody is contacted with a preparation that includes a varicella zoster polypeptide, for instance an isolated varicella zoster polypeptide or fragment thereof, to form a mixture. The varicella zoster polypeptide includes a polymorphism and can encoded by a polymorphism of ORF37. The polymorphism in the polypeptide encoded by the polymorphic ORF37 can be due to a single amino acid polymorphism, which can be present in the polypeptide as a leucine at amino acid 269. Alternatively, the varicella zoster polypeptide includes a polymorphism and can encoded by a polymorphism of ORF68. The polymorphism in the polypeptide encoded by the polymorphic ORF68 can be due to a single amino acid polymorphism, which can be present in the polypeptide as an asparagine at amino acid 150. The mixture is incubated under conditions to allow the antibody to specifically bind the polypeptide to form a polypeptide:antibody complex. The presence or absence of the polypeptide:antibody complex is then detected. Detecting the polypeptide:antibody complex indicates the presence of antibodies that specifically bind to a varicella zoster polypeptide.

The preparation can include whole varicella zoster virus, for instance VZV-MSP or a modified varicella zoster virus, where the modified virus has the ATCC designation VR-795 wherein the nucleotide sequence of the virus has been modified to comprise the polymorphism of ORF37 or ORF68. The biological sample can be blood, vesicle fluid, bone marrow, brain tissue, or combinations thereof. Also provided are kits for detecting antibodies that specifically bind to a varicella zoster polypeptide. This kits include a whole varicella zoster virus.

In another aspect, the present invention provides a method for detecting the presence of a varicella zoster virus in an animal. The method includes detecting the presence of an antibody to a varicella zoster virus polypeptide encoded by a polymorphic ORF of GenBank X04370. The ORF can be ORF37 or ORF68, where the encoded polypeptide includes a single amino acid polymorphism. When the polypeptide is encoded by ORF37, the single amino acid polymorphism present in the polypeptide can be a leucine at amino acid 269. When the polypeptide is encoded by ORF68, the single amino acid polymorphism present in the polypeptide can be an asparagine at amino acid 150. Optionally, the antibody that is detected does not specifically bind to the varicella zoster polypeptide encoded by ORF37 of GenBank Accession X04370 or ORF68 of GenBank Accession X04370.

The present invention is also directed to a method for diagnosing a disease, for instance chicken pox and shingles, caused by varicella zoster virus. The method includes contacting a polynucleotide, optionally an isolated polynucleotide, of a subject suspected of having a disease caused by varicella zoster virus with a primer pair. This is incubated under conditions suitable to form a detectable amplification product, and the primer pair will not form a detectable amplification product when incubated with a polynucleotide having the nucleotide sequence of GenBank Accession X04370. An amplification product is detected, where the detection indicates that the subject has a disease caused by varicella zoster virus. The polynucleotide of the subject can be present in a biological sample, including blood, vesicle fluid, bone marrow, brain tissue, or combinations thereof.

The polynucleotide that is amplified to result in a detectable amplification product can include a single nucleotide polymorphism relative to the nucleotide sequence of GenBank Accession X04370 (SEQ ID NO:76). The primer pair can include a first primer that includes nucleotides that hybridize with a polynucleotide of GenBank Accession X04370, and a second primer comprising nucleotides that hybridize with a polynucleotide of GenBank Accession X04370, with the proviso that the 3' nucleotide of the second primer hybridizes to the single nucleotide polymorphism relative to the nucleotide sequence of GenBank Accession X04370 and does not hybridize with the corresponding nucleotide present in the nucleotide sequence of GenBank Accession X04370. The single nucleotide polymorphism can be present in ORF37, and the single nucleotide polymorphism can be present at nucleotide 806 of ORF37. The nucleotide at nucleotide 806 can be a thymine. The single nucleotide polymorphism can be present in ORF68, and the single nucleotide polymorphism can be present at nucleotide 448 of ORF68. The nucleotide at nucleotide 448 can be an adenine. An example of a primer pair is CGATGACAGACATAAAATTGTAAATGTGA (SEQ ID NO:1) and CACCCAAGTATTGTTTTTCTGTCCG (SEQ ID NO:2). nucleotide of the second primer hybridizes to the single nucleotide polymorphism relative to the nucleotide sequence of GenBank Accession X04370 and does not hybridize with the corresponding nucleotide present in the nucleotide sequence of GenBank Accession X04370. The single nucleotide polymorphism can be present in ORF37, and the single nucleotide polymorphism can be present at nucleotide 806 of ORF37. The nucleotide at nucleotide 806 can be a thymine. The single nucleotide polymorphism can be present in ORF68, and the single nucleotide polymorphism can present at nucleotide 448 of ORF68. The nucleotide at nucleotide 448 can be an adenine. An example of a primer pair is CGATGACAGACATAAAATTGTAAATGTGA (SEQ ID NO:1) and
CACCCAAGTATTGTTTTTCTGTCCG (SEQ ID NO:2).

The present invention further provides a method for detecting a varicella zoster virus, for instance VZV-MSP, having a single nucleotide polymorphism in ORF68. The method includes contacting a polynucleotide with a primer pair and incubating under conditions suitable to form a detectable amplification product. The primer pair amplifies a portion of ORF68 of GenBank Accession X04370 and/or a polymorphism thereof, that includes nucleotide 448 of ORF68. The amplification product is exposed to a restriction endonuclease having nucleotide 448 in its recognition sequence. Examples of restriction endonuclease include AflI, AsuI, AvaII, Cfrl3I, Eco47I, NspIV, PshAI, Sau96I, and SinI. The amplification product is then detected. The presence of an amplification product that is not cleaved by the restriction endonuclease indicates the presence of a varicella zoster virus having a single nucleotide polymorphism in ORF68. The polynucleotide can be present in a biological sample, including, for instance, blood, vesicle fluid, bone marrow, brain tissue, or combinations thereof. Optionally, the polynucleotide can be isolated. An example of a primer pair is GGCATACTACCAATGACACG (SEQ ID NO:12) and
AAGCTCCAAGTCTCGGTGTACC (SEQ ID NO:71).

The present invention is directed to a vaccine composition that includes a modified attenuated varicella zoster virus. The modified attenuated virus has the ATCC designation VR-795, and the nucleotide sequence of the virus has been modified to contain a single nucleotide polymorphism. The single nucleotide polymorphism can be present in the coding sequence encoding glycoprotein H. For instance, the single nucleotide polymorphism in the virus can be present at nucleotide 806 of the coding sequence encoding glycoprotein H. The nucleotide present at nucleotide 806 can be a thymine. The single nucleotide polymorphism can be present in the coding sequence encoding glycoprotein E. For instance, the single nucleotide polymorphism in the virus is present at nucleotide 448 of the coding sequence encoding glycoprotein E. The nucleotide present at nucleotide 448 can be an adenine.

Also provided by the present invention is a method for producing a modified attenuated varicella zoster virus. The method includes growing the virus in a tissue culture preparation. The virus has the ATCC designation VR-795, and the nucleotide sequence of the virus has been modified to contain a single nucleotide polymorphism. The single nucleotide polymorphism can be present in the coding sequence encoding glycoprotein H. For instance, the single nucleotide polymorphism in the virus can be present at nucleotide 806 of the coding sequence encoding glycoprotein H. The nucleotide present at nucleotide 806 can be a thymine. The single nucleotide polymorphism can be present in the coding sequence encoding glycoprotein E. The single nucleotide polymorphism in the virus can be present at nucleotide 448 of the coding sequence encoding glycoprotein E. The nucleotide present at nucleotide 448 can be an adenine. The modified attenuated virus can have an in vitro growth rate that is greater than the in vitro growth rate of a second varicella zoster virus. The second varicella zoster virus can be, for instance, VZV-32, ATCC VR-586, ATCC VR-1367, or ATCC VR-795. The growth rate of the modified varicella virus can be at least about 4-fold greater than the second varicella zoster virus at 48 hours post infection. Optionally, the modified varicella virus can be isolated.

The present invention further provides isolated polynucleotides, including an isolated polynucleotide having the nucleotide sequence of nucleotides 66,074 to 68,599 of GenBank Accession X04370, with the proviso that nucleotide 66,879 is a thymine; and an isolated polynucleotide having the nucleotide sequence of nucleotides 115,808 to 117,679 of GenBank Accession X04370, with the proviso that nucleotide 116,255 is an adenine. Also provided are the isolated polypeptides encoded by each of the above two polynucleotides. The polynucleotide can be isolated from a varicella zoster virus.

Also provided are viruses having the designation VZV-MSP, VZV-VSD, VZV-VIA, or VZV-Iceland.

Definitions

As used herein, an antibody that can "specifically bind" a polypeptide is an antibody that interacts only with the epitope of the antigen that induced the synthesis of the antibody, or interacts with a structurally related epitope. "Epitope" refers to the site on an antigen to which specific B cells and/or T cells respond so that antibody is produced. As used herein, the term "polypeptide:antibody complex" refers to the complex that results when an antibody specifically binds to a polypeptide.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like. Coding sequence, coding region, and open reading frame are used interchangeably and refer to a polynucleotide that encodes a polypeptide, usually via mRNA, when placed under the control of appropriate regulatory sequences. The boundaries of the coding region are generally determined by a translation start codon at its 5' end and a translation stop codon at its 3' end.

An "ORF" followed immediately by a number, for instance ORF37 or ORF68, refers to a specific open reading frame of varicella zoster virus. The approximately 70 individual open reading frames of varicella zoster virus are known to the art, and are described in Davison et al. (*J. Gen. Virol.*, 67:1759–1816 (1986)) and at GenBank Accession X04370. GenBank Accession X04370 is also referred to herein as SEQ ID NO:76. For instance, ORF37 is the open reading frame encoded by nucleotides 66,074 to 68,599 of the nucleotide sequence at GenBank Accession X04370, and ORF68 is the open reading frame encoded by nucleotides 115,808 to 117,679 of the nucleotide sequence at GenBank Accession X04370. A "polymorphic ORF" followed immediately by a number, for instance polymorphic ORF37 or polymorphic ORF68, refers to an open reading frame of varicella zoster virus that has a nucleotide sequence similar to the appropriate nucleotide sequence of GenBank X04370, but includes a single nucleotide polymorphism. Moreover, a polymorphic ORF may contain an insertion or deletion of nucleotides, preferably an insertion of 3 nucleotides or a deletion of 3 nucleotides. When referring to a specific nucleotide of an ORF, the first nucleotide of the start codon is considered to be nucleotide 1, with the following amino acids labeled consecutively. When referring herein to a specific amino acid of a polypeptide encoded by an ORF, the first methionine (prior to any post-translational modification that may occur) is considered to be amino acid 1, with the following amino acids labeled consecutively.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences. A polynucleotide can be obtained directly from a natural source, for instance from a virus, or can be prepared with the aid of recombinant, enzymatic, or chemical techniques. A polynucleotide can be linear or circular in topology. A polynucleotide can be, for example, a portion of a vector, such as an expression or cloning vector, or a fragment.

An "isolated" polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities. An "isolated" varicella zoster virus means a varicella zoster virus has been removed from its natural environment, e.g, the cell that produced the virus.

As used herein, the term "whole varicella zoster virus" refers to a varicella zoster virus particle or virion. The particle can be infective, i.e., be able to reproduce when introduced to an appropriate tissue culture cell under the appropriate conditions, or the particle can be inactive, i.e., incapable of reproducing.

As used herein, a "biological sample" refers to a sample of tissue or fluid isolated from a subject, including but not limited to, for example, blood, plasma, serum, lymph tissue and lymph fluid, cerebrospinal fluid, bone marrow, brain tissue, samples of the skin, external secretions of the skin including vesicle fluid from a pox, organs, biopsies and also samples of in vitro cell culture constituents including but not limited to conditioned media resulting from the growth of cells and tissues in culture medium, and cell components, or combinations thereof. A "subject" is an animal, including, for instance, a mouse or a human, preferably a human.

As used herein, the term "whole varicella zoster virus particle" refers to an intact varicella zoster virus, for instance a varicella zoster virus that has been produced by a cell and not manipulated to cause the polypeptides that make up the envelop to disassociate from one another.

As used herein, a "primer pair" refers to two single stranded polynucleotides that can be used together to amplify a region of a polynucleotide, preferably by a polymerase chain reaction (PCR). The polynucleotide that results from amplifying a region of a polynucleotide is referred to as an "amplification product." The phrase "under conditions suitable to form a detectable amplification product" refers to the reactions conditions that result in an amplification product. For instance, in the case of a PCR, the conditions suitable to form a detectable amplification product include the appropriate temperatures, ions, and enzyme.

As used herein, the term "hybridize" refers to the ability of two complementary single stranded polynucleotides to base pair with each other, where an adenine of one polynucleotide will base pair to a thymine of a second polynucleotide and a cytosine of one polynucleotide will base pair to a guanine of a second polynucleotide. When the term "hybridize" is used to describe the interaction between a primer and a polynucleotide, hybridization requires that the 3' nucleotide of a primer be able to base pair with the corresponding nucleotide of the polynucleotide that is to be amplified. Typically, the inability of the 3' nucleotide of a primer to base pair with the polynucleotide that is to be amplified results in no amplification (see Newton et al., U.S. Pat. No. 5,595,890).

As used herein, the term "in vitro growth rate" refers to the rate at which a varicella zoster virus spreads from an infected tissue culture cell to an adjacent uninfected tissue culture cell. A tissue culture cell is a cell that replicate in vitro in a nutritive media. The in vitro growth rate of a varicella zoster virus can be measured as described herein.

As used herein, the term "vaccine composition" refers to a pharmaceutical composition containing an antigen, where the composition can be used to prevent or treat a disease or condition in a subject. "Vaccine composition" thus encompasses both subunit vaccines, as described below, as well as compositions containing whole killed, attenuated or inactivated virus. "Subunit vaccine composition" refers to a composition containing at least one immunogenic polypeptide, but not all antigens, derived from a varicella zoster virus. Such a subunit vaccine composition is substantially free of intact virus particles. Thus, a "subunit vaccine composition" is prepared from an isolated, preferably purified, immunogenic polypeptide from the virus. A subunit vaccine composition can comprise the subunit antigen or antigens of interest isolated from other antigens or polypeptides from the pathogen.

As used herein, an "attenuated varicella zoster virus" refers to a varicella zoster virus that is less virulent in humans and preferably, when introduced to a human in the appropriate manner, causes a protective immunological response such that resistance to infection will be enhanced and/or the clinical severity of the disease reduced.

As used herein, a "single nucleotide polymorphism" and a "single amino acid polymorphism" refers to a specific type of polymorphism in a polynucleotide and a polypeptide, respectively, and are described in greater detail herein.

As used herein, the term "re cognition sequence" refers to the site on a polynucleotide to which a restriction endonuclease binds prior to cleaving the polynucleotide.

Unless other wise specified, "a," "an," "the," and "at least one" are used interchangeably and mean one or more than one.

BRIEF DESCRIPTION OF THE FIGURES

FIG. 1. Sequence of the ectodomain of VZV gE. (A) The deduced amino acid sequence of the N-terminal 400 of 623 codons of wild-type VZV gE. The previously defined MAb 3B3 epitope is underlined. The aspartic acid residue altered in VZV-MSP is designated by an arrowhead at codon 150. The silent mutation is indicated by an arrowhead at codon 341. (B) Nucleotides 149–161 and deduced amino acid sequence of the MAb 3B3 epitope in the wild type VZV-32 strain (designated VZV gE) and the mutant VZV-MSP strain gE gene (designated VZV gE-D150N). The altered nucleotides (G to A) and amino acids (D to N) are underlined and marked with the arrow. The two additional codons inserted into the expression plasmid described in FIG. 4 are designated 3B3.2, while the original 3B3 epitope is designated 3B3.11.

FIG. 2. Recombination PCR mutagenesis. Two additional codons (3B3.2) were inserted into the MAb 3B3 epitope to produce plasmid gL 3B3.13 from plasmid gL 3B3.11.

FIG. 3. Quantitative analysis of VZV IE 62 by confocal microscopy. VZV-MSP or VZV-32 infected monolayers were examined by confocal microscopy at increasing times post-infection at ×4 magnification. The total number of pixels positive for VZV IE 62 within each image was quantitated with the Brainvox tal_support programs (University of Iowa) as described herein. The graph summarizes the results from four separate images. Error bars: +/−1 S.D.

FIG. 4. Infectious center assays of VZV-MSP and VZV-32.

FIG. 5. Summary of genetic analysis of VZV-MSP (A) Schematic diagram showing regions of the VZV-MSP genome where the nucleotide sequence has been determined. ORFs 31, 37, 47, 60, 61, 62, 66, 67, and 68 are shown. The polypeptide encoded by the ORF is shown in parentheses under the appropriate ORF. The horizontal arrows above the schematic of the VZV-MSP genome represent the location of the ORFs and the direction of transcription. $U_L$, unique long; IRs, internal repeat short ; $U_S$, unique short; TRs, terminal repeat short; shaded boxes, regions of the VZV-MSP that have been sequenced; hatched boxes, repeat sequences. (B) Summary of results of sequence analysis of amplified fragments. All mutations discovered are listed by the nucleotide number of the Dumas strain. Any substitutions within open reading frames are followed by the predicted amino acid expressed by VZV-MSP. Nucleotides, nucleotides that were sequenced (the numbering system used is that described in Davison et al., (*J. Gen. Virol.*, 67:1759–1816 (1986))); Size of Region, number of nucleotides sequenced; ORF(s), the ORF or region near an ORF that was sequenced; Substitutions, locations and nature of single nucleotide polymorphism. If the single nucleotide polymorphism encodes a mutation in the resulting polypeptide, the location and nature of the mutation is shown in parentheses. For instance, at position 269 of glycoprotein gH, the proline has been replaced with a leucine.

FIG. 6. Comparative sequence analysis of the VZV gE. VZV ORF 68 was amplified from the viral DNA of eight VZV strains, including VZV-MSP. Each sequence was compared to the prototype VZV-Dumas genotype. The location of each detected polymorphism is designated by nucleotide number (bp) of the gE gene. Any resulting single amino acid polymorphism that results in gE (e.g., T>I) is noted below the location of the appropriate detected polymorphism. Silent, the single nucleotide polymorphism did not result in a single amino acid polymorphism; asterisk, location of the single nucleotide polymorphism.

FIG. 7. Comparative sequence analysis of VZV gI. VZV ORF 67 was amplified from viral DNA of eight VZV strains. Each sequence was compared to prototype VZV-Dumas genotype. Any resulting single amino acid polymorphism that results in gI (e.g., Q>H) is noted below the location of the appropriate detected polymorphism. Silent, the single nucleotide polymorphism did not result in a single amino acid polymorphism.

FIG. 8. Comparative sequence analysis of VZV gH. VZV ORF 37 was amplified from viral DNA of eight VZV strains. Each DNA sequence was compared to the prototype VZV-Dumas genotype. Nucleotide variations from the VZV-Dumas genotppe were tabulated. The P269L mutation originally discovered in VZV-MSP was also present in six other VZV strains, including VZV-32. A total of nine polymorphisms within ORF 37 were discovered among the eight tested strains. Any resulting single amino acid polymorphism that results in gH (e.g., R>K) is noted below the location of the appropriate detected polymorphism. Silent, the single nucleotide polymorphism did not result in a single amino acid polymorphism.

FIG. 9. Comparative sequence analysis of VZV gL. VZV ORF 60 was amplified from eight VZV strains. Each sequence was compared to the VZV Dumas genotype. Only the gL gene of VZV Oka differed from the gL sequence of VZV Dumas.

FIG. 10. Comparative sequence analysis of the VZV IE 62 regulatory gene. VZV ORF 62 was amplified from eight VZV strains. Each sequence was compared to the VZV-Dumas genotype. A total of 38 polymorphisms were detected among the eight VZV strains. VZV-MSP contained only a silent substitution within codon 30 when compared to the VZV-Dumas gene. Any resulting single amino acid polymorphism that results in IE 62 (e.g., S>A) is noted below the location of the appropriate detected polymorphism. Asterisk, location of single nucleotide polymorphism that did not result in a single amino acid polymorphism

DETAILED DESCRIPTION OF THE INVENTION

Polynucleotides

The present invention provides polynucleotides, preferably isolated polynucleotides, having a (at least one) single nucleotide polymorphism. An isolated polynucleotide has a nucleotide sequence that is identical to a nucleotide sequence present in VZV-Dumas, but there is a nucleotide that is polymorphic between the isolated polynucleotide of the present invention and the corresponding polynucleotide present in VZV-Dumas. The nucleotide sequence of VZV-Dumas is present at GenBank Accession X04370. The term "polymorphism" refers to the coexistence of at least two different forms (i.e., at least two different nucleotide sequences or at least two different amino acid sequences) of a polynucleotide or a polypeptide in members of Varicella zoster. The polymorphism can be due to a single nucleotide that is different (a single nucleotide polymorphism). In contrast, a polymorphism can be due to several consecutive nucleotides, for instance 2, 3, or 4 consecutive nucleotides, that are different, which is not within the scope of the present definition of "single nucleotide polymorphism." In the isolated polynucleotides of the present invention, a polymorphism is due to, in increasing order of preference, the presence of 1 single nucleotide polymorphism, at least 1, at least 2, at least 3, most preferably at least 4 single nucleotide polymorphisms in the polynucleotide. Preferably, the isolated polynucleotides of the present invention include no greater than 4 single nucleotide polymorphisms. A single nucleotide polymorphism could be separated from another single nucleotide polymorphism by only one nucleotide.

An example of a polynucleotide of the present invention is a polymorphic ORF37 or the complement thereof, where a polymorphism is at nucleotide 806 of ORF37 (see FIG. 8). The nucleotide at nucleotide 806 can be a guanine, adenine, or thymine, preferably a thymine.

Another example of a polynucleotide of the present invention has the nucleotide sequence of nucleotides 101,650 to 103,081 (i.e., the region upstream of ORF60) of GenBank Accession X04370 or the complement thereof, but contains a single nucleotide polymorphism at nucleotide 102,203, or a single nucleotide polymorphism at nucleotide 102,575, or a single nucleotide polymorphism at nucleotide 102,617, or a single nucleotide polymorphism at nucleotide 102,969. The nucleotide at nucleotide 102,203 can be a guanine, cytosine, or thymine, preferably a guanine. The nucleotide at nucleotide 102,575 can be a guanine, cytosine, or thymine, preferably a guanine. The nucleotide at nucleotide 102,617 can be a guanine, adenine, or thymine, preferably a thymine. The nucleotide at nucleotide 102,969 can be a guanine, cytosine, or thymine, preferably a guanine.

A further example of a polynucleotide of the present invention has the nucleotide sequence of nucleotides 104,468 to 104,936 (i.e., the region upstream of ORF6 1) of GenBank Accession X04370 or the complement thereof, but contains a single nucleotide polymorphism at nucleotide 104,898. The nucleotide at nucleotide 104,898 can be a guanine, cytosine, or thymine, preferably a guanine.

Another example of a polynucleotide of the present invention is a polymorphic ORF62 or the complement thereof, where a polymorphism is at nucleotide 90 of ORF62 (see FIG. 10). The nucleotide at nucleotide 90 can be a guanine, adenine, or thymine, preferably a guanine.

Another example of a polynucleotide of the present invention is a polymorphic ORF66 or the complement thereof, where a polymorphism is at nucleotide 1,104 of ORF66. The nucleotide at nucleotide 1,104 can be a guanine, cytosine, or thymine, preferably a guanine.

Another example of a polynucleotide of the present invention is a polymorphic ORF68 or the complement thereof, where a polymorphism is at nucleotide 448 of ORF68 (see FIG. 6). The nucleotide at nucleotide 448 can be an adenine, cytosine, or thymine, preferably an adenine.

Other examples of polynucleotides of the present invention are shown in FIGS. 5–10.

The polynucleotides of the present invention can be obtained by recombinant techniques known to the art including, for instance, cloning from a member of Varicella zoster or mutagenizing a polynucleotide so that it has the nucleotide sequence of a polynucleotide of the present invention. Alternatively, a polynucleotide of the present invention can be chemically or enzymatically synthesized by, for instance, an oligonucleotide synthesizer or PCR.

The present invention further includes polynucleotides that are similar to polynucleotides of the present invention as described above, including nucleotides of a polymorphic ORF37 or a polymorphic ORF68, or the complements thereof. The similarity is referred to as structural similarity and is determined by aligning the residues of the two polynucleotides (i.e., the nucleotide sequence of the candidate polynucleotide and the nucleotide sequence of a preferred polynucleotide of the invention) to optimize the number of identical nucleotides along the lengths of their sequences; gaps in either or both sequences are permitted in making the alignment in order to optimize the number of shared nucleotides, although the nucleotides in each sequence must nonetheless remain in their proper order. Moreover, the nucleotide at the position of the single nucleotide polymorphism (e.g., the thymine at nucleotide 806 in a polymorphic ORF37) is invariant in the candidate polynucleotide. A candidate polynucleotide is the polynucleotide being compared to a preferred polynucleotide of the present invention. Preferably, two nucleotide sequences are compared using the Blastn program, version 2.0.14, of the BLAST 2 search algorithm, as described by Tatusova, et al. (*FEMS Microbiol Lett* 1999, 174:247–250), and available at http://www.ncbi.nlm.nih.gov/gorf/bl2.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, a polynucleotide includes a nucleotide sequence having a structural similarity with a preferred polynucleotide of the present invention of at least about 98%, more preferably at least about 99%, most preferably at least about 99.5% identity.

The present invention further includes isolated polynucleotide fragments. A polynucleotide fragment is a portion of an isolated polynucleotide as described herein, where the portion is preferably at least about 15, more preferably at least about 20, most preferably at least about 25 consecutive nucleotides and includes at least one single nucleotide polymorphism. The single nucleotide polymorphism can be at any location in the polynucleotide fragment, and preferably is the nucleotide at one of the 3' ends of the fragment (when the polynucleotide fragment is double stranded) or the nucleotide at the 3' end of the fragment (when the polynucleotide fragment is single stranded).

A polynucleotide of the invention can be inserted in a vector. Construction of vectors containing a polynucleotide of the invention employs standard ligation techniques known in the art. See, for instance, Sambrook et al, *Molecular Cloning: A Laboratory Manual.*, Cold Spring Harbor Laboratory Press (1989). A vector can provide for further cloning (amplification of the polynucleotide), i.e., a cloning vector, or for expression of the polypeptide encoded by the coding sequence, i.e., an expression vector. The term vector includes, but is not limited to, plasmid vectors, viral vectors, cosmid vectors, or artificial chromosome vectors. Typically, a vector is capable of replication in a bacterial host, for instance *E. coli*. Preferably the vector is a plasmid.

Selection of a vector depends upon a variety of desired characteristics in the resulting construct, such as a selection marker, vector replication rate, and the like. Suitable host cells for cloning or expressing the vectors herein are prokaryote or eukaryotic cells. Preferably the host cell secretes minimal amounts of proteolytic enzymes. Suitable prokaryotes include eubacteria, such as gram-negative or gram-positive organisms. Preferably, *E. coli* is used.

Suitable host cells for the expression of the polypeptides of the invention, preferably encoded by a polymorphic ORF37 or a polymorphic ORF68 as described herein and containing a single amino acid polymorphism can be derived from multicellular organisms. Such host cells are capable of complex processing and glycosylation activities. Vertebrate or invertebrate culture can be used. Numerous baculoviral strains and variants and corresponding permissive insect host cells from hosts such as *Spodoptera frugiperda, Aedes aegypti, Aedes albopictus, Drosophila melanogaster, Trichoplusia ni,* and *Bombyx mori* are known to the art.

Vertebrate cells can also be used as hosts. Examples of useful mammalian host cell lines are monkey kidney CV1 line transformed by SV40 (CAS-7, ATCC CRL-1651); human embryonic kidney line (293 or 293 cells subcloned for growth in suspension culture, Graham et al., *J. Gen. Virol.*, 36:59 (1977)); baby hamster kidney cells (BHK, ATCC CCL 10); Chinese hamster ovary cells/-DHFR (CHO); CHO-K1 (ATCC CCL-61); CHO-D; mouse sertoli cells (TM4); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI 38, ATCC CCL 75); human liver cells (Hep G2, HB 8065); mouse mammary tumor (MMT 060562, ATCC CCL 51); TRI cells; MRC 5 cells; FS4 cells; and a human hepatoma line (Hep G2).

Suitable plasmids for expression in *E. coli*, for example, include pUC(X), pKK223-3, pKK233-2, pTrc99A, and pET-(X) wherein (X) denotes a vector family in which numerous constructs are available. pUC(X) vectors can be obtained from Pharmacia Biotech (Piscataway, NH) or Sigma Chemical Co. (St. Louis, Mo.). pKK223-3, pKK233-2 and pTrc99A can be obtained from Pharmacia Biotech. pET-(X) vectors can be obtained from Promega (Madison, Wis. Stratagene (La Jolla, Calif.) and Novagen (Madison, Wis.). To facilitate replication inside a host cell, the vector preferably includes an origin of replication (known as an "ori") or replicon. For example, ColE1 and P15A replicons are commonly used in plasmids that are to be propagated in *E. coli.*

Suitable plasmids for expression in eukaryotic cells, for example, include the EPITAG vectors available from Invitrogen (Carlsbad, Calif.) for mammalian cells. Examples of suitable EPITAG vectors include pcDNA3.1/myc-His and pEF1/myc-His. Other plasmids that can be used in mammalian cells include, for example, pRc/RSV (Invitrogen) and pSecTag2 (Invitrogen). Suitable plasmids for expression in insect cells include, for instance, pIZ/V5-His (Invitrogen), and pBlueBac4.5 (Invitrogen).

An expression vector optionally includes regulatory sequences operably linked to the coding sequence. The invention is not limited by the use of any particular promoter, and a wide variety are known. Promoters act as regulatory signals that bind RNA polymerase in a cell to initiate transcription of a downstream (3' direction) coding sequence. The promoter used in the invention can be a constitutive or an inducible promoter. It can be, but need not be, heterologous with respect to the host cell. Preferred promoters for bacterial transformation include lac, lacUV5, tac, trc, T7, SP6 and ara.

Promoter sequences are known for eukaryotes. Most eukaryotic coding sequences have an AT-rich region located approximately 25 to 30 bases upstream from the site where transcription is initiated. Another sequence found 70 to 80 bases upstream from the start of transcription of many genes is the CXCAAT region where X may be any nucleotide. At the 3' end of most eukaryotic genes is an AATAAA sequence that may be a signal for addition of the poly A tail to the 3' end of the coding sequence. All these sequences are suitably inserted into eukaryotic expression vectors.

Transcription of a coding sequence encoding a polypeptide of the present invention in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, and Hepatitis-B virus.

Transcription of a coding sequence encoding a polypeptide of the present invention by eukaryotes can be increased by inserting an enhancer sequence into the vector. Enhancers are cis-acting elements of DNA, usually having about 10 to 300 bp, that act on a promoter to increase its transcription. Enhancers are relatively orientation- and position-independent, having been found 5' and 3' to coding sequences, within an intron as well as within the coding sequence itself. Many enhancer sequences are now known from mammalian genes (globin, elastase, albumin, alpha-fetoprotein, and insulin). Enhancers from eukaryotic cell viruses are also known and include the SV40 enhancer on the late side of the replication origin, the cytomegalovirus early promoter enhancer, the polyoma enhancer on the late side of the replication origin, and adenovirus enhancers. The enhancer may be spliced into the vector at a position 5' or 3' to the coding sequence encoding a polypeptide of the present invention, but is preferably located at a site 5' of the promoter.

An expression vector can optionally include a ribosome binding site (a Shine Dalgarno site for prokaryotic systems or a Kozak site for eukaryotic systems) and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The polynucleotide used to transform the host cell can optionally further include a transcription termination sequence. The rrnB terminators, which is a stretch of DNA that contains two terminators, T1 and T2, is an often used terminator that is incorporated into bacterial expression systems. Transcription termination sequences in vectors for eukaryotic cells typically include a polyadenylation signal 3' of the coding sequence.

The polynucleotide used to transform the host cell optionally includes one or more marker sequences, which typically encode a molecule that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, tetracycline, neomycin, and formulations of phleomycin D1 including, for example, the formulation available under the trade-name ZEOCIN (Invitrogen).

Polypeptides

The present invention is also directed to polypeptides, preferably isolated polypeptides, encoded by polynucleotides of the present invention. A polypeptide has an amino acid sequence that is identical to an amino acid sequence encoded by a coding sequence present in VZV-Dumas, but there is an amino acid that is polymorphic between the polypeptide of the present invention and the corresponding polypeptide encoded by VZV-Dumas. The polymorphism can be due to a single amino acid that is different (a single amino acid polymorphism). In contrast, a polymorphism can be due to several consecutive amino acids, for instance 2, 3, or 4 consecutive amino acids, that are polymorphic, which is not within the scope of the present definition of "single amino acid polymorphism." In the polypeptides of the present invention, a polymorphism is due to, in increasing order of preferance, the presence of 1 single amino acid polymorphism, at least 1, at least 2, at least 3, most preferably at least 4 single amino acid polymorphisms in the polypeptide. Preferably, the isolated polypeptides of the present invention include no greater than 4 single amino acid polymorphisms. A single amino acid polymorphism could be separated from another single amino acid polymorphism by only one amino acid.

Preferably, a polypeptide of the present invention has immunogenic activity. "Immunogenic activity" refers to an amino acid sequence which elicits an immunological response in a subject. An immunological response to a polypeptide is the development in a subject of a cellular and/or antibody-mediated immune response to the polypeptide fragment. Usually, an immunological response includes but is not limited to one or more of the following effects: the production of antibodies, B cells, helper T cells, suppressor T cells, and/or cytotoxic T cells, directed specifically to an epitope or epitopes of the polypeptide fragment.

The polypeptides of the present invention can be obtained from, for instance, a biological sample from a subject infected with a varicella zoster virus that encodes the polypeptide. The polypeptide can be obtained from tissue culture cells that have, for instance, been infected with a varicella zoster virus that encodes the polypeptide or contain a recombinant polynucleotide, preferably a polynucleotide of the invention, that encodes the polypeptide of the invention. Alternatively, the polypeptide can be obtained from a prokaryotic cell, for instance Eschericia coli, that contains a recombinant polynucleotide, preferably a polynucleotide of the invention, that encodes the polypeptide of the invention. The polypeptides of the present invention can also be obtained by chemical synthesis.

An example of a polypeptide of the present invention is encoded by a polymorphic ORF37, where a polymorphism is at amino acid 269 (see FIG. 8). When referring herein to a specific amino acid of a polypeptide encoded by an open reading frame, the first methionine is considered to be amino acid 1, with the following amino acids labeled consecutively. The polypeptide encoded by ORF37 is referred to in the art as glycoprotein H, gH, and gpIII. Preferably, the amino acid at position 269 in the polypeptide encoded by a polymorphic ORF37 is an amino acid other than proline, more preferably, the amino acid is a nonpolar (hydrophobic) amino acid, for instance alanine, leucine, isoleucine, valine, phenylalanine, tryptophan, or tyrosine, most preferably, the amino acid is leucine.

An example of a polypeptide of the present invention is encoded by a polymorphic ORF68, where a polymorphism is at amino acid 150 (see FIG. 6). The polypeptide encoded by nucleotides ORF68 is referred to in the art as glycoprotein E, gE, and gpI. Preferably, the amino acid at position 150 in the polypeptide encoded by a polymorphic ORF68 is an amino acid other than aspartic acid, more preferably, the amino acid is asparagine, lysine, histidine, or glutamic acid, most preferably, the amino acid is asparagine.

Other examples of polypeptides of the present invention are shown in FIGS. 5–10.

The present invention further includes polypeptides having similarity with the polypeptides of the present invention as described above, including the polypeptide encoded by a polymorphic ORF37 or a polymorphic ORF68. The similarity is referred to as structural similarity and is generally determined by aligning the residues of the two amino acid sequences (i.e., a candidate amino acid sequence and the amino acid sequence of a preferred polypeptide of the present invention) to optimize the number of identical amino acids along the lengths of their sequences; gaps in either or both sequences are permitted in making the alignment in order to optimize the number of identical amino acids, although the amino acids in each sequence must nonetheless remain in their proper order. Moreover, the amino acid at the position of the single amino acid polymorphism (e.g., the leucine at amino acid 269 in the polypeptide encoded by a polymorphic ORF37) is invariant in the candidate polypeptide. A candidate amino acid sequence is the amino acid sequence being compared to an amino acid sequence present in a preferred polypeptide of the present invention. Preferably, two amino acid sequences are compared using the Blastp program, version 2.0.14, of the BLAST 2 search algorithm, as described by Tatusova et al. (*FEMS Microbiol. Lett.*, 174:247–250 (1999)), and available at http://www.ncbi.nlm.nih.gov/gorf/bl2.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identities." Preferably, a polypeptide includes an amino acid sequence having a structural similarity with a preferred polypeptide of the present invention of, in increasing order of preference, at least about 96%, at least about 97%, at least about 98%, and most preferably, at least about 99% identity.

The present invention further includes polypeptide fragments. A polypeptide fragment is a portion of a polypeptide as described herein, where the portion includes at least one single amino acid polymorphism. Preferably, the polypeptide fragment has immunogenic activity. Preferably, a polypeptide fragment is at least about 8, more preferably at least about 12, most preferably at least about 20 amino acids in length.

Viruses

The present invention further provides isolated varicella zoster viruses. Preferably, the genome of an isolated varicella zoster virus of the present invention includes, in increasing order of preference, 1, at least 1, at least 2, at least 3, most preferably at least 4 single nucleotide polymorphisms when compared to the nucleotide sequence of GenBank Accession X04370. Preferably, the genome of an isolated varicella zoster virus of the present invention includes no greater than 4 single nucleotide polymorphisms. Examples of isolated varicella zoster viruses of the present invention include VZV-MSP, VZV-VSD, VZV-VIA, VZV-Iceland. Alternatively, the isolated varicella zoster virus can be a modified varicella zoster virus, preferably a modified attenuated varicella zoster virus. Modified varicella zoster viruses are described in greater detail herein.

A single nucleotide polymorphism can be present in a coding sequence where it can result in the encoded polypeptide containing a single amino acid polymorphism when compared to the polypeptides encoded by the nucleotide sequence of GenBank X04370. Alternatively, a single nucleotide polymorphism can be silent, i.e., not alter the amino acid sequence of a polypeptide encoded by a coding sequence. A single nucleotide polymorphism can be present in a region of the genome that is not a coding sequence. In an isolated varicella zoster virus of the present invention that encodes a polypeptide having a single amino acid polymorphism, the varicella virus may have a serotype that is different than the serotype known to the art. Preferably, the serotype of an isolated varicella zoster virus of the invention is one that does not contain the epitope to which the monoclonal antibody 3B3 binds. Monoclonal antibody is available from the ATCC (accession number HB-12377). An example of a varicella zoster virus having this serotype is VZV-MSP.

Preferably, the isolated varicella zoster viruses of the present invention have the ability to spread from one cell to another at a rate that is greater than previously characterized varicella zoster viruses. This phenotype, which is also referred to herein as in vitro growth rate and cell-to-cell spread, can be measured by methods that are known to the art, including, for instance, the methods described in Example 2 (i.e., laser scanning confocal microscopy combined with pixel intensity measurement, infectious center assays, and replication in the SCID-hu mouse). Examples of previously characterized varicella zoster viruses that can be used as a baseline for measuring the in vitro growth rate of an isolated varicella virus of the present invention include VZV-32, Oka strain (see Kubo, U.S. Pat. No. 3,985,615), or the varicella zoster viruses having the designations ATCC VR-586, ATCC VR-1367, or ATCC VR-795. Examples of tissue culture cells that can be used include human melanoma cells (including, for instance, MeWo cells), lung fibroblasts (including, for instance, MRC-5 cells, which have the ATCC designation CCL-171), cells derived from human embryos, simian cells, or guinea pig cells.

Preferably, when the infectious center assay is used to measure the in vitro growth rate of a varicella zoster virus, tissue culture cells are added to the well of a 35-mm tissue culture plate and grown until they form a substantially confluent monolayer. The well is inoculated with between about 300 infectious centers to about 700 infectious centers, preferably about 500 infectious centers, i.e., an aliquot of the appropriate varicella zoster virus to result in the initial infection of about 500 cells. The resulting number of infectious centers in the well is measured at 24 hours after inoculation and at 48 hours after inoculation. Preferably, the number of infectious centers of a varicella zoster virus at 48 hours after inoculation is at least about 1.5-fold greater, more preferably at least about 2-fold greater, most preferably at least about 3-fold greater than a previously characterized varicella zoster virus.

Preferably, when laser scanning confocal microscopy combined with pixel intensity measurement is used to measure the in vitro growth rate of a varicella zoster virus, tissue culture cells are inoculated with the varicella zoster virus to be measured. These infected cells are then used to inoculate uninfected cells at a 1:8 ratio of infected to uninfected cells. The spread of the varicella zoster virus is then determined at 24 hours after inoculation at the 1:8 ratio and at 48 hours after inoculation at the 1:8 ratio. The spread of the varicella zoster virus away from a single cell that initially contained the virus can be measured by assaying for evidence of virus in adjacent cells. For instance, the presence of viral nucleic acid or a viral encoded polypeptide can be measured. Preferably, the presence of a viral encoded polypeptide is measured. Preferably, the viral encoded polypeptide is IE62. Preferably, the spread of a varicella zoster virus at 24 hours after inoculation at the 1:8 ratio is at least about 1.5-fold greater, more preferably at least about 2-fold greater than a previously characterized varicella zoster virus. Preferably, the spread of a varicella zoster virus at 48 hours after inoculation at the 1:8 ratio is at least about 2-fold greater, more preferably at least about 4-fold greater than a previously characterized varicella zoster virus.

The present invention is also directed at modifying a varicella zoster virus so that it has an in vitro growth rate that is greater than the in vitro growth rate prior to modification. A varicella zoster virus can be modified by altering the genome of the varicella zoster virus. Preferably, the genome is modified to contain, in increasing order of preference, 1 single nucleotide polymorphism, at least 1, at least 2, at least 3, most preferably, at least 4 single nucleotide polymorphisms. Preferably, the genome is modified to include no greater than 4 single nucleotide polymorphisms. The single nucleotide polymorphisms that could be incorporated into the genome of a varicella zoster virus are described herein. Methods of modifying a genome of a varicella zoster virus are known to the art (see, for instance, Cohen et al., *Proc. Natl. Acad. Sci. USA*, 90:7376–7380 (1993)). Preferably, recombinant DNA techniques are used to make the modification. Preferably, the single nucleotide polymorphisms that could be incorporated into a varicella zoster virus include nucleotide 806 of ORF37, where the single nucleotide polymorphism is a thymine, and/or nucleotide 448 of ORF68, where the single nucleotide polymorphism is an adenine. Examples of varicella zoster viruses that could be modified include a clinical isolate, Oka strain (see Kubo, U.S. Pat. No. 3,985,615), ATCC VR-586, ATCC VR-1367, or ATCC VR-795, preferably ATCC VR-795. It is expected that varicella zoster virus that is presently used to produce, for instance, antigen for diagnostic assays or whole virus for use in vaccine compositions, can be modified by this method. Diagnostic assays and vaccine compositions are described in greater detail herein. The modified virus will grow at a faster rate and result in lowered production costs.

Another aspect of the present invention is directed to methods for producing a varicella zoster virus that has a high in vitro growth rate. Preferably, the varicella zoster virus has an in vitro growth rate that is greater than the in vitro growth rate of a second varicella zoster virus, including, for instance, a clinical isolate, Oka strain (see Kubo, U.S. Pat. No. 3,985,615), VZV-32, ATCC VR-586, ATCC VR-1367, or ATCC VR-795. The method can further include isolation of the varicella virus that has the high in vitro growth rate.

Methods of Use

The present invention provides methods for detecting a varicella zoster virus. These methods are useful in, for instance, detecting a varicella zoster virus in an animal, diagnosing a disease caused by a varicella zoster virus, and detecting a varicella zoster virus having a single nucleotide polyporphism. Preferably, such diagnostic systems are in kit form. Kits are described in greater detail herein. In some aspects of the invention, preferably the varicella zoster virus detected is one having a serotype that is different than VZV-32, or the varicella zoster viruses having the designations ATCC VR-586, ATCC VR-1367, or ATCC VR-795, or having a single nucleotide polymorphism when compared to the nucleotide sequence of GenBank Accession X04370. Preferably, the varicella zoster virus detected is one to which the monoclonal antibody 3B3 does not bind. In some aspects of the invention, detecting a varicella zoster virus includes detecting antibodies that specifically bind to a varicella zoster polypeptide. Whether an antibody specifically binds a polypeptide or non-specifically binds a polypeptide can be determined using methods that are known in the art. Preferably, the polypeptide is gE, gH, gB, or IE62, most preferably gE. The methods include contacting an antibody with a preparation that includes a varicella zoster polypeptide to result in a mixture. Preferably, the antibody is present in a biological sample, more preferably blood, vesicle fluid, bone marrow, or brain tissue.

In this aspect of the invention the varicella zoster virus polypeptide contains a polymorphism. Such polypeptides are described herein. Preferably, the varicella zoster virus polypeptide is encoded by a polymorphic ORF68, and the encoded polypeptide includes an asparagine at amino acid 150. Alternatively and optionally, the varicella zoster virus polypeptide is encoded by a polymorphism of ORF37, and the encoded polypeptide includes a leucine at amino acid 269. The varicella zoster polypeptide in the preparation can be an isolated varicella zoster polypeptide or fragment thereof. Alternatively, preparation can further include whole varicella zoster virus, preferably VZV-MSP, VZV-VSD, VZV-VIA, or VZV-Iceland, more preferably, VZV-MSP.

The method farther includes incubating the mixture under conditions to allow the antibody to specifically bind the polypeptide to form a polypeptide:antibody complex. The preparation that includes the varicella zoster virus may also includes reagents, for instance a buffer, that provide conditions appropriate for the formation of the polypeptide:antibody complex. The polypeptide:antibody complex is then detected. The detection of antibodies is known in the art and can include, for instance, immunofluorescence and peroxidase.

The methods for detecting the presence of antibodies that specifically bind to a varicella zoster polypeptide can be used in various formats that have been used to detect antibody to varicella zoster virus, including complement fixation, indirect fluorescent antibody, fluorescent antibody to membrane antigen, neutralization, indirect hemagglutination, immune adherence hemagglutination, radioimmunoassay, latex agglutination, and enzyme-linked immunosorbent assay.

Other methods for detecting a varicella zoster virus include the amplification of a polynucleotide, preferably by PCR. The polynucleotide can be one that is, for instance, isolated from a subject, preferably a subject suspected of having a disease caused by varicella zoster virus. Preferably, the polynucleotide is from a subject, for instance a biological sample, preferably blood, vesicle fluid, bone marrow, or brain tissue. In some aspects of the invention, the method includes contacting a polynucleotide, preferably an isolated polynucleotide, with a primer pair, incubating under conditions suitable to form a detectable amplification product, and detecting the amplification product. Detection indicates that the subject has a disease caused by varicella zoster virus.

The primer pair is one that will not form a detectable amplification product when incubated with a polynucleotide having the nucleotide sequence of GenBank Accession X04370, and preferably will form a detectable amplification product with a polynucleotide containing a single nucleotide polymorphism described herein. Preferably, one of the primers of the primer pair has a nucleotide sequence that hybridizes to a nucleotide sequence of GenBank Accession X04370; however, the 3' nucleotide of the primer corresponds to a single nucleotide polymorphism present in the varicella zoster virus that is to be detected. This method is known to the art as amplification refractory mutation system (ARMS; see Newton et al., U.S. Pat. No. 5,595,890). For instance, a primer pair could be CGATGACAGACAT-AAAATTGTAAATGTGA (SEQ ID NO:1), where the underlined nucleotide corresponds to the single nucleotide polymorphism present in VZV-MSP in the coding sequence of nucleotides 115,808 to 117,679 (i.e., the polymorphic ORF68 coding sequence), and CACCCAAGTAT-TGTTTTTCTGTCCG (SEQ ID NO:2). Optionally, an additional amplification can be done to detect a varicella zoster virus that does not have the single nucleotide polymorphism by using, for instance, a primer pair that will form a detectable amplification product when incubated with a polynucleotide having the nucleotide sequence of GenBank Accession X04370. An example of such a primer pair is CGATGACAGACATAAAATTGTAAATGTGG (SEQ ID NO:3), and CACCCAAGTATTGTTTTTCTGTCCG (SEQ ID NO:2). Other primer pairs can be designed using methods known to the art to detect other single nucleotide polymorphisms described herein.

In another aspect of the invention that involves detecting a varicella zoster virus by amplification of a polynucleotide, preferably by PCR, the method is directed to detecting a varicella zoster virus having a single nucleotide polymorphism, preferably at nucleotide 448 of ORF68. Preferably, in the varicella zoster virus to be detected, nucleotide 448 of ORF68 is a cytosine, thymine, or adenine, more preferably an adenine. The method includes contacting a polynucleotide with a primer pair and incubating under conditions suitable to form a detectable amplification product. The amplification product is then exposed to a restriction endonuclease, preferably one that has the recognition sequence that includes nucleotide 448 and is no longer able to cleave when that nucleotide of the recognition sequence is not a guanine. Examples of such restriction endonuclease are AflI, AsuI, AvaII, Cfrl 3I, Eco47I, NspIV, PshAI, Sau96I, and SinI. In VZV-Dumas and other varicella zoster viruses, the nucleotide at position 448 of ORF68 in the viral genome is a guanine, and is cleaved by the above-identified restriction endonucleases. When the nucleotide at position 448 of a polymorphic ORF68 is a cytosine, thymine, or adenine, more preferably an adenine, the restriction endonuclease is no longer able to cleave the amplification product. Thus, the method further includes detecting the amplification product after exposure to the restriction endonuclease. The presence of an amplification product that is not cleaved by, for instance, AvaII, indicates the presence of a varicella zoster virus having a single nucleotide polymorphism at nucleotide 448.

The primer pair that is used in this aspect of the invention must amplify a region of varicella zoster virus genomic DNA that includes nucleotide 116,255. Without intending to be limiting, an example of a primer pair includes GGCAT-ACTACCAATGACACG (SEQ ID NO:12) and AAGCTC-CAAGTCTCGGTGTACC (SEQ ID NO:71), as well as some of the primers listed in Table 1. Other primers can be designed using methods known in the art.

The methods that involve detecting a varicella zoster virus by amplification of a polynucleotide, preferably by PCR, can also be used to determine the percentage of a population that has a particular single nucleotide polymorphism. Methods of screening populations for the presence of a single nucleotide polymorphism are known to the art. For instance, PCR is sensitive enough to allow samples from a large number of subjects to be pooled and assayed for the presence of a varicella zoster virus having a single nucleotide polymorphism.

The present invention also provides a kit for detecting a varicella zoster virus. The kit includes a varicella zoster polypeptide as described herein (when detecting antibody to varicella zoster virus) or a primer pair as described herein (when amplifying a polynucleotide) in a suitable packaging material in an amount sufficient for at least one assay. Optionally, other reagents such as buffers and solutions needed to practice the invention are also included. Instructions for use of the packaged polypeptide or primer pair are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the polypeptide or primer pair can be used for detecting a varicella zoster virus. In addition, the packaging material contains instructions indicating how the materials within the kit are employed to detect a varicella zoster virus. As used herein, the term "package" refers to a solid matrix or material such as glass, plastic, paper, foil, and the like, capable of holding within fixed limits a polypeptide or a primer pair. Thus, for example, a package can be a glass vial used to contain milligram quantities of a primer pair, or it can be a microtiter plate well to which microgram quantities of a polypeptide have been affixed. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is also directed to vaccines. In one aspect, the present invention is directed to vaccine compositions. Preferably, the subject receiving the vaccine composition will display a protective immunological response such that resistance to infection will be enhanced and/or the clinical severity of the disease reduced. A vaccine composition can include a modified varicella zoster virus, more preferably a modified attenuated varicella zoster virus. A varicella zoster virus can be modified as described above under "Viruses." In other alphaherpesviruses, for instance, pseudorabies virus (PRV), it has been found that spread of the virus in an infected animal is facilitated by gE mutations that reduce virulence (Yang et al., *J. Virol.*, 73:4350 (1999)), it has been found that increasing the in vitro growth rate does not result in an increased virulence of the virus. It is expected that the varicella zoster viruses used as a source of viral antigen for vaccination can be modified to have an increased in vitro growth rate, and not have a increase in virulence. Preferably, the varicella zoster virus that is modified to have an increased in vitro growth rate is Oka strain (see Kubo, U.S. Pat. No. 3,985,615), or ATCC VR-795. The modified varicella zoster virus of the vaccine composition can a live virus, or an inactivated whole virus preparation. The virulence of a varicella zoster virus modified to have a higher in vitro growth rate can be determined using methods known in the art, for instance by using human volunteers.

In another aspect, the vaccine composition can include an isolated varicella zoster virus polypeptide of the present invention or a fragment thereof. Varicella zoster virus polypeptides of the present invention are described herein.

The vaccine composition includes polypeptide or modified varicella zoster viruses having immunogenic activity. Immunogenic carriers can be used to enhance the immunogenicity of the polypeptide or modified varicella zoster viruses. Such carriers include but are not limited to other polypeptides, polysaccharides, liposomes, and bacterial cells and membranes. Polypeptide carriers may be joined to the polypeptides or modified varicella zoster viruses of the present invention to form fusion polypeptides by recombinant or synthetic means or by chemical coupling. Useful carriers and means of coupling such carriers to polypeptide antigens are known in the art.

The vaccine compositions may be formulated by means known in the art. The formulations include those suitable for parental (including subcutaneous, intramuscular, intraperitoneal, and intravenous administration. They are typically prepared as injectables, either as liquid solutions or suspensions. Solid forms suitable for solution in, or suspension in, liquid prior to injection may also be prepared. The composition may also, for example, be emulsified, or the polypeptide or modified varicella zoster virus encapsulated in liposomes. Where mucosal immunity is desired and the vaccine includes a polypeptide or an inactivated varicella virus, the vaccine compositions may advantageously contain an adjuvant such as the nontoxic cholera toxin B subunit (see, e.g., U.S. Pat. No. 5,462,734). Cholera toxin B subunit is commerically available, for example, from Sigma Chemical Company, St. Louis, Mo. Other suitable adjuvants are available and may be substituted therefor.

The polypeptide or modified varicella zoster virus can be mixed with pharmaceutically acceptable excipients or carriers. Suitable excipients include but are not limited to water, saline, dextrose, glycerol, ethanol, or the like and combinations thereof. In addition, if desired, the vaccine compositions may contain minor amounts of auxiliary substances such as wetting or emulsiwing agents, pH buffering agents, and/or adjuvants which enhance the effectiveness of the vaccine. Such additional formulations and modes of administration as are known in the art may also be used.

The present invention is illustrated by the following examples. It is to be understood that the particular examples, materials, amounts, and procedures are to be interpreted broadly in accordance with the scope and spirit of the invention as set forth herein.

EXAMPLE 1

Identification of Single Nucleotide Polymorphisms in ORF 68 (the gE gene) of VZV-MSP This example demonstrates the presence of a single nucleotide polymorphism in gE. Because of the important functions of gE, this discovery was completely unexpected. This example provides a more complete characterization of the altered biological properties and genetic composition of this contemporary variant in VZV evolution. For the first time, a VZV variant virus has been discovered which has a cell-to-cell spread phenotype clearly distinguishable from previously characterized VZV strains.

Materials and Methods
Viruses and Cells

The mutant VZV was isolated from a 6 year old boy with leukemia, who contracted chickenpox and was hospitalized for intravenous acyclovir treatment in late 1995. The child's illness responded to treatment and no unusual sequelae were observed. The child's vesicle fluid was inoculated onto MRC-5 cells in glass tubes. The isolate was designated VZV-MSP because the child lived in Minnesota. The VZV-32 laboratory strain was isolated in Texas in 1976 from an otherwise healthy child with chickenpox (Grose, *Virology*, 101:1–9 (1980)). This virus has never been passaged more than 20 times. The VZV Oka strain was isolated from a Japanese child with chickenpox and attenuated by M. Takahashi in Japan in the 1970s (Takahashi et al., *Biken J.*, 18:25–33 (1975)). All viruses were subcultured in either MRC-5 cells or human melanoma cells (MeWo strain, available from C. Grose, University of Iowa, Iowa). MeWo cells are highly permissive for VZV replication but no infectious virus is released into the culture medium (Grose, *Virology*, 101:1–9 (1980)). Therefore, transfer of infectivity is carried out by trypsin dispersion of infected cells and relayering of infected cells onto an uninfected monolayer at a ratio of 1:8 (infected to uninfected cells). The HSV-1 Miyama strain was propagated in the FL line derived from human amnion cells (Padilla et al, *J. Elect. Microscopy*, 46:171–180 (1997)).

Antibodies and Immunodetection by Confocal Microscopy

MAb 3B3 was produced in this laboratory (Grose et al., *Infect. Immun.*, 40:381–388 (1983)). The antigen for mouse immunization was VZV-32 infected cells. MAb 3B3 attaches to VZV gE even under stringent conditions of buffers containing 1% SDS. Other monoclonal antibodies to VZV gE (MAb 711), VZV gI (MAb 6B5) and VZV gH (MAb 206) were also produced and characterized in this laboratory and are described in Grose (*Annu. Rev. Microbiol.*, 44: 59–80 (1990). Conditions for immunodetection of VZV proteins by laser scanning confocal microscopy have been outlined by Duus et al., (*J. Virol.*, 70:8961–8971 (1996)). Immunoblotting was performed with the above antibodies as described (Grose, *Annu. Rev. Microbiol.*, 44:59–80 (1990)).

Epitope Mapping by Recombination PCR Mutagenesis

The technique of recombination PCR mutagenesis has been adapted to investigate epitope mapping and tagging (Yao et al., *J. Virol.*, 67:305–314 (1993), Hatfield et al., *BioTechniques*, 22:332–337 (1997)). By this methodology, the epitope of MAb 3B3 was initially defined between amino acids 151–161 in the ectodomain of the 623-amino acid gE glycoprotein. The methodology for producing plasmid pTM1-VZV gL 3B3.11 is described in detail by Hatfield et al., (*BioTechniques*, 22:332–337 (1997)). As part of the investigation in Results (FIG. 2), an additional two codons were inserted at the N-terminus of the 11-amino acid 3B3 epitope, to produce a 13-amino acid epitope tag in the VZV gL protein. The mutating primers included the following: MP23 (sense) CAT ACT GTG TCG ACC AAA GGC AAT ACG GTG ACG TG (SEQ ID NO:4) and MP24 (antisense) TTG CCT TTGGGTC GAC ACA GTA TGC GAT TGT GAT AG (SEQ ID NO:5). PCR amplification was performed under the following parameters: 94° C. denaturation for 30 seconds, 50° C. annealing for 30 seconds, 72° C. extension for 5 minutes; after 25 cycles, there was a final extension at 72° C. for 7 minutes. PCR products were combined and transformed into cells where the overlapping regions underwent recombination to yield a plasmid containing the mutagenized insert. Plasmid purification was performed with a Qiagen Maxi Kit. The newly designated pTM1-VZV gL 3B3.13 plasmid was partially sequenced at the University of Iowa DNA Core Facility to confirm the authenticity of the insertional mutagenesis. This PCR mutagenesis protocol is very reliable with a error frequency of less than 0.025% (Jones et al., *BioTechniques*, 8:178–183 (1990)).

Subcloning of VZV-MSP gE

The subdloning of wild type VZV gE has been described previously (Yao et al., *J. Virol.*, 67:305–314 (1993)). Briefly, two flanking PCR primers were utilized which amplified the VZV-MSP gE ORF directly from VZV-MSP infected melanoma cells. These primers also created a Sac I and a Spe I restriction enzyme site at the 5' and 3' ends, respectively. The primers were the following: Nco gpI (sense) CGA CCC GGG GAG CTC CCA TGG GGA CAG TTA ATA AAC C (SEQ ID NO:6) and IP2 (anti-sense) CGC TCT AGA ACT AGT GGA TCC CCC GGG GAA TTT GTC ACA GGC TTT T (SEQ ID NO:7). PCR amplification was performed using AmpliTaq (Applied Biosystems, Foster City, Calif.) under the following conditions: 94° C. denaturation for 40 seconds, 50° C. annealing for 40 seconds, 72° C. extension for 4 minutes; after 35 cycles, there was a final extension at 72° C. for 7 minutes. After amplification, the PCR fragment was digested with Sac I and Spe I before cloning into the multiple cloning site of the expression vector pTM1.

Imaging of Viral Particles

Clean coverslips were coated with carbon, hydrophilized, irradiated with ultraviolet light for 12 hours, followed by a glow discharge for a few seconds and then sterilization by dry heat (160° C. overnight). MeWo cells were cultivated on the glass coverslips. When the cells became confluent, they were co-cultivated with either VZV-32 or VZV-MSP infected cells at a 1:8 ratio and incubated at 32° C. At the designated times after infection, the cells were prefixed with 1% glutaraldehyde in PBS at 4° C. for 1 hour, rinsed in chilled PBS followed by postfixation with 1% osmium tetraoxide in PBS at 4° C. for 1 hour, and then dehydrated in a graded ethanol series. Finally, after two changes in 100% ethanol, the specimens were subjected to a critical point drying method. In the case of HSV-1 samples, FL cells prepared on coverslips were inoculated with HSV-1 Miyama strain at an MOI of 10. Twenty four hours after virus inoculation, coverslips were washed with PBS and processed as described for VZV. Subsequently, the specimens were mounted onto aluminum plates and observed with either a Hitachi S4000 or a Hitachi S-900 SEM. Imaging was performed at the University of Iowa Central Microscopy Research Facility and the University of Wisconsin-Madison Integrated Microscopy Facility.

Results

Analysis of the VZV Isolate by Confocal Microscopy

The virus designated VZV-MSP was initially isolated in human fibroblast monolayers. The cytopathic effect (CPE) was compatible with VZV, but the isolate was poorly reactive with antibodies in a commercial VZV diagnostic kit. Since the isolate did not stain with antibodies to herpes simplex virus (HSV) types 1 and 2 nor did its CPE resemble that of HSV, the virus isolate was further analyzed. When the isolate (VZV passage 1) was received, the infected cell monolayer was trypsin-dispersed and inoculated onto human melanoma cells (VZV passage 2). When CPE was apparent in 5 days, the infected cell monolayer was trypsin-dispersed one more time and inoculated onto 35 mm monolayers for examination by laser scanning confocal microscopy (VZV passage 3). The low passage VZV-32 strain was included in separate dishes as a control virus. When CPE covered about 70% of each monolayer, the infected monolayers were probed with MAb 3B3 against gE and MAb 6B5 against gI and examined by confocal microscopy. In prior studies, it has been shown that these two MAbs do not cross-react with other viral or cellular proteins (Grose, *Annu. Rev. Microbiol.*, 44:59–80 (1990)). As expected from numerous published experiments, MAb 3B3 and MAb 6B5 reacted with the laboratory strain VZV-32. In marked contrast, the anti-gE MAb 3B3 did not attach to cells infected with the VZV-MSP strain, even though MAb 6B5 did bind the infected cells strongly. As an additional control, the anti-gH MAb 206 was added to cultures individually infected with both VZV strains; all VZV-infected cultures were positive in this assay.

The next question addressed was whether the VZV-MSP strain failed to express the entire glycoprotein or whether it has lost an epitope on the glycoprotein. Monoclonal antibodies produced in the epitope-mapping of gE were used. It was previously established that the 3B3 epitope consisted of at least 11 amino acids 151–161 of gE (Duus et al., *J. Virol.*, 70:8961–8971 (1996)). Another monoclonal antibody, MAb 711, attaches to another as yet undefined epitope on the ectodomain of gE. This epitope does not overlap with the 3B3 epitope. Therefore, the above experiment was repeated with MAb 711 as the immunoprobe of VZV-32 and VZV-MSP infected monolayers. Both monolayers stained positively, a result which indicated that gE was expressed in VZV-MSP infected cells but appeared to have lost either a small segment of its ectodomain or just the 3B3 epitope.

Sequence Analysis of VZV-MSP gE

To further investigate the nature of the gE mutation, we used PCR amplification techniques to first determine whether a full-length gE gene (VZV ORF 68) was present in the mutant strain. The full length gene was amplified. Thereafter, primers were used to amplify overlapping portions of the gE gene, each overlapping portion about 300 bases in size, beginning at the upstream region of ORF 68. Each fragment was subjected to DNA sequencing and each sequence was compared with the published Davison and Scott (Davison et al., *J. Gen. Virol.*, 67:1759–1816 (1986)) sequence of the Dumas strain (FIG. 1A; Genbank Accession number X04370). After analysis of the first 337 codons of VZV-MSP gE ORF, we found the first and most important base change in codon 150 (FIG. 1B, arrow); the substitution involved a replacement of a guanine by an adenine. Of great interest, this point mutation led to a change in amino acid from aspartic acid to asparagine (FIG. 1B). Since this alteration in gE occurred one amino acid away from the deduced 3B3 epitope, which is underlined in FIG. 1A, the sequence data strongly suggested that amino acid 150 was a previously unrecognized contributor to the 3B3 epitope. Further sequencing of VZV-MSP gE revealed one silent mutation in codon 341 of VZV-MSP gE. All other codons were identical to those in the gE sequence of the Dumas strain.

Epitope Mapping of VZV-MSP gE

In an earlier experiment, we had evaluated the 3B3 epitope by inserting the 11-amino-acid sequence into the unrelated VZV ORF 60, namely, the gL glycoprotein (Duus et al., *J. Virol.*, 70:8961–8971 (1996)). The epitope tag within gL was recognized by MAb 3B3 when observed by laser scanning confocal microscopy. To evaluate the contribution of the aspartic acid residue to formation of the epitope, the gL epitope mapping and tagging experiment was repeated in order to insert the aspartic acid residue in its correct location at the N-terminus of the 3B3 epitope. In order to obtain the proper parameters for the mutagenesis primers, one additional codon was inserted along with an aspartic acid (FIG. 1B). The pTM-1 expression plasmids, including gL-3B3.11 and gL-3B3.13, were transfected into HeLa cells and observed by confocal microscopy after labeling with MAb 3B3. Cells transfected with the gL-3B3.11 plasmid were positive in a restricted cytoplasmic pattern, as previously described by Duus et al., (*J. Virol.*, 70:8961–8971 (1996)). Cells transfected with the gL-3B3.13 were not only more intensely stained, the pattern was more widely distributed throughout the cytoplasm. Cells transfected with the pTM-1 gL plasmid alone were negative.

Subcloning the VZV-MSP gE ORF

After completion of the above experiment, we sought to confirm the epitope experiments by amplifying the entire gE gene from VZV-MSP DNA and inserting it into a pTM-1 expression vector. We had previously cloned wild-type gE into the same expression vector; the same primers were used for the second cloning experiment (Yao et al., *J. Virol.*, 67:305–314 (1993)). After transient transfection with these two forms of VZV gE as well as the pTM-1 vector as a control, the cell lysates were solubilized and subjected to electrophoresis followed by transfer to membranes. Additional control samples for the transfection immunoblotting experiments included MeWo cell monolayers infected with three VZV strains: VZV-32, VZV-Oka and VZV-MSP. Uninfected MeWo cells served as a negative control. All samples were blotted with MAb 3B3 followed by detection using chemiluminesence. The MAb attached to VZV-32, VZV Oka and VZV gE wild type, but not to VZV-MSP, VZV MSP gE or the vector and uninfected cell controls. When VZV-MSP gE was subsequently immunoblotted with a polyclonal monospecific antibody to gE, the result was positive. Thus, these results confirmed that VZV-MSP gE by itself was expressed but lacked the 3B3 epitope.

Alterations in Topography of Egress of Viral Particles

In previously published studies, it was shown that the egress of wild type VZV particles onto the surface of infected cells occurs in a distinctive pattern which was termed "viral highways" (Harson et al., J. Virol., 69:4994–5010 (1995)). The viral highways are composed of thousands of viral particles which emerge in long rows across the surface of the syncytia. When the distribution of VZV-32 and VZV-MSP particles were compared at a low magnification level by scanning electron microscopy (SEM), wild type virions were again arranged in a pattern consistent with viral highways. Cells infected with the VZV-Oka strain show a similar pattern of viral highways (Grose, Infect. Dis. Clinics NA, 10: 489–505 (1996)). In contrast, no such topographical pattern was observed on samples infected with VZV-MSP; instead, viral particles were distributed more uniformly over the cell surface. After observation of numerous monolayers by SEM, it appeared that the number of VZV wild type virions present on the cell surface was less than those of VZV-MSP. The topographical arrangement of VZV-MSP particles also exhibited a high degree of similarity with that of HSV-1, in which thousands of particles covered the cell surface.

In a VZV-infected monolayer, cytopathic effect follows the longitudinal axis of the cells. In VZV-infected human melanoma cell cultures, individual syncytial foci enlarge and eventually merge until the entire monolayer has become a single syncytium. Virions only emerge after syncytia are formed but the virions are never released into the culture medium. If syncytial formation is blocked by adding anti-gH antibody into the culture medium, virions do not egress until the antibody is removed. Based on the imaging studies in this as well as previous reports, it is postulated that virions exit at the leading edge of syncytial foci which are merging. Further, VZV egress (gE/gI mediated) and VZV-induced cell-to-cell fusion (gH/gL mediated) are separate but inter-dependent events. The mutation on VZV-MSP gE appears to lessen that interdependence.

EXAMPLE 2

Identification of Single Nucleotide Polymorphisms in other ORFs of VZV-MSP and Assessment of Cell-to-cell Spread This example provides a more complete characterization of the altered biological properties and genetic composition of this contemporary variant in VZV evolution. For the first time, a varicella zoster virus variant is described which has a cell-to-cell spread phenotype clearly distinguishable from previously characterized varicella zoster virus strains.

Cells, viruses and transfer of infectivity. VZV-MSP was isolated in Minnesota in late 1995. VZV-32 was isolated in Texas in the 1970s (Grose et al., *Infect. Immun.*, 19:199–203 (1978)). Reserve stocks of VZV-32 and VZV-MSP were prepared; thus low passages (<20) were used in all experiments in this report. VZV-Oka was isolated in Japan and attenuated in the 1970s (Takahashi et al., *Biken J.*, 18:25–33 (1975)). VZV-Dumas was isolated in Holland and sequenced in its entirety by Davison et al., (Davison et al., *J. Gen. Virol.*, 67:1759–816 (1986)). All strains were propagated in human melanoma cells (MeWo strain). MeWo cells are highly permissive for VZV replication with no release of infectious virus into the culture medium (Grose, *Virology* 101:1–9 (1980)). Transfer of infectivity was carried out by inoculation of trypsin-dispersed infected cells onto an uninfected monolayer at a 1:8 ratio of infected: uninfected cells unless otherwise noted. Similarly, infectious center assays were carried out by described methods; these assays included both melanoma cell and human neonatal foreskin cell substrates (Cole et al., *J. Virol. Methods*, 36:111–8 (1992), Grose et al., Infect. *Immun.*, 19:199–203 (1978)).

Imaging by confocal microscopy. Replicate 35-mm monolayers of MeWo cells were overlaid with VZV-infected cells at a 1:8 ratio of infected:uninfected cells. At 4, 8, 12, 24, and 48 hours post-infection, the monolayers were fixed and permeabilized with 0.5 ml 2% paraformaldehyde with 0.05% Triton X-100. Cells were probed with an anti-IE 62 mouse monoclonal ascites (MAb 5C6, available from C. Grose, University of Iowa, Iowa) at a dilution of 1:1,000 (Ng et al., *J. Virol.*, 68:1350–1359 (1994)). The secondary antibody was goat anti-mouse IgG F(ab')$_2$ conjugated to Alexa 488 at a dilution of 1:2,500 (Molecular Probes, Eugene, Oregon). Cell nuclei were stained with TOTO-3 (Molecular Probes), a dimeric cyanine nucleic acid stain, at a dilution of 1:10,000. Samples were examined with a BioRad 1024 laser scanning confocal microscope, as described (Duus et al., *Virology* 210:429–440 (1995)).

Quantitative Analysis of Confocal Images. Confocal images were converted to TIFF format images (Confocal Assistant, v. 4.02, Bio-Rad Laboratories (Hercules, Calif.), available from ftp://ftp.genetics.bio-rad.com/Public/confocal/cas) and transferred to a Silicon Graphics Indy workstation in order to produce the color prints by Showcase software program (Silicon Graphics, Mountain View, Calif.)). Confocal images also were analyzed with the Brainvox tal_support programs (Frank et al., *Neuroimage*, 5:13–30 (1997)). Similar analyses can be performed with the public domain NIH Image program, which was developed at the U.S. National Institutes of Health (http://rsb.info.nih.gov/nih-image/).

Replication in the SCID-hu mouse. The SCID-hu mouse has been established as an animal model for VZV replication (Moffat et al., *J. Virol.*, 69:5236–42 (1995)). In this model, C.B-17 scid/scid mice were implanted with fetal skin tissue subcutaneously as full thickness dermal grafts. Human fetal tissues were obtained with informed consent according to federal and state regulations and were screened for human immunodeficiency virus. The general care of the experimental animals used for this study was in accordance with the National Institutes of Health guidelines for laboratory animals and in compliance with the Animal Welfare Act (Public Law 94–279) as well as the Stanford University Administrative Panel on Laboratory Animal Care. Animal inoculations were performed according to the previously described protocol (Moffat et al., *J. Virol.*, 69:5236–42 (1995)), viz., an aliquot of infected cell suspension containing $10^5$ infectious centers was injected into each implant. Mock-infected implants were injected with human cells alone. Skin implants were harvested at 7, 14 and 21 days post-inoculation. The implants were fixed in 4% paraformaldehyde, paraffin-embedded, cut into 3-$\mu$m sections, and stained with hematoxylin and eosin. Tissue sections were examined on a Leitz Diaplan light microscope, and digital images were acquired with an Optronics DEI 750 digital camera (Optronics Engineering, Goleta, Calif.). Digital images were formatted as described above.

Isolation of viral DNA. For all viral strains, a 25 cm² monolayer of MeWo cells was infected as described above. After development of 80–100% cytopathology, the infected monolayer was washed thrice with 0.5 ml of 0.01 M phosphate buffered saline (PBS), pH 7.4. Infected cells were then harvested by dislodging into 0.5 ml of PBS. Viral DNA was collected with a DNA easy Kit following the Blood and Body Fluid Protocol (Qiagen Inc, Valencia, Calif.). Following DNA easy protocol, DNA was placed onto a Microcon 50 filter (Millipore, Bedford, Mass.) and washed twice with 0.5 ml of Nanopure water (Bamstead/Thermolyne, Dubuque, Iowa). Viral DNA was resuspended in 100 µL of Nanopure water. DNA concentration was assessed visually after 1% agarose gel electrophoresis.

PCR amplification and sequencing of VZV genes. For each ORF, a pair of flanking primers was designed to amplify the gene of interest. PCR amplifications were performed with the Expand High-Fidelity PCR System (Boehringer Mannheim, Indianapolis, Ind.). This system utilizes both Taq DNA and Pwo DNA polymerases, with the 3'-5' proofreading activity of Pwo DNA polymerase allowing increased fidelity ($8.5 \times 10^{-6}$ per bp error rate) (Boehringer Mannheim). After amplification, the PCR product was sequenced by using the dye terminator cycle sequencing chemistry with AmpliTaq DNA polymerase, FS enzyme (Perkin Elmer Applied Biosystems, Foster City, Calif.). Sequencing reactions were performed on and analyzed with an Applied Biosystems Model 373A stretch fluorescent automated sequencer (Perkin Elmer) at the University of Iowa DNA facility. All genes were PCR amplified twice and each PCR fragment was sequenced at least twice to confirm reported mutations. Each DNA sequence was compared to the prototype VZV-Dumas sequence. The accession number for the complete VZV-Dumas sequence is X04370. The primers used for amplification and/or sequencing the amplified fragments are shown in Table 1.

TABLE 1

VZV sequencing and amplification primers

| Protein[1] | Primer[2] | bp[3] | Seq/Amp[4] | Sequence[5] |
|---|---|---|---|---|
| gB (ORF 31) | Scp 1 (S) | −163 to −136 | Seq/Amp | GGCGTTTTCATAACCTCCGTTACGGGGG (SEQ ID NO:8) |
| | Scp 2 (AS) | 2685 to 2658 | Seq/Amp | CCCTGTGATGCGTAATGGAGACACATGA (SEQ ID NO:9) |
| | Sp 1 (A) | 309 to 328 | Seq | CTTTGTAATATACCGTCGCC (SEQ ID NO:10) |
| | Sp 2 (S) | 201 to 220 | Seq | CGTACGATTAGAACCAACTC (SEQ ID NO:11) |
| | Sp 3 (S) | 569 to 588 | Seq | GGCATACTACCAATGACACG (SEQ ID NO:12) |
| | Sp 4 (S) | 929 to 948 | Seq | AGTGGCGTGAGGTTGAAGAC (SEQ ID NO:13) |
| | Sp 5 (S) | 1264 to 1283 | Seq | CACCCGACTCGAAATACCAG (SEQ ID NO:14) |
| | Sp 6 (S) | 1615 to 1634 | Seq | TCTGGTAGTACTACGCGTTG (SEQ ID NO:15) |
| | Sp 7 (S) | 1948 to 1970 | Seq | GACTACAGTGAAATTCAACGCCG (SEQ ID NO:16) |
| | Sp 8 (S) | 2259 to 2279 | Seq | CCCGATGAAGGCATTATATCC (SEQ ID NO:17) |
| | Sp 9 (A) | 1418 to 1437 | Amp | TAGCTGGCACCACGACGAGG (SEQ ID NO:18) |
| | Sp 10 (A) | 2565 to 2584 | Amp | TGCGAACACGGGAGTATCCT (SEQ ID NO:19) |
| gH (ORF 37) | Sp 2 (S) | 104 to 131 | Seq | CTGCTCTTCTACGAGAATATTCCGACCG (SEQ ID NO:20) |
| | Sp 3 (A) | 223 to 199 | Seq | CGTGTTTTCTATCATTTCCCCAGTG (SEQ ID NO:21) |
| | Sp 4 (S) | 448 to 471 | Seq | ACTACGTTCCCACCAAACCCCCTTG (SEQ ID NO:22) |
| | Sp 5 (S) | 850 to 873 | Seq | GCGGTTACAAGCGACACCACATGG (SEQ ID NO:23) |
| | Sp 6 (S) | 1165 to 1191 | Seq | CTGTTAGATGAGATCGTAGATGTTCAG (SEQ ID NO:24) |
| | Sp 7 (S) | 1498 to 1514 | Seq | GCTACAGAGAGGCAGGCT (SEQ ID NO:25) |
| | Sp 8 (S) | 1816 to 1840 | Seq | TTGCATACCCAACTAGACGAATCTG (SEQ ID NO:26) |
| | Sp 9 (S) | 2129 to 2152 | Seq | TAGAGACGGTCGCACTGCCCCATC (SEQ ID NO:27) |
| | Sp 10 (S) | −32 to −5 | Seq/Amp | CGGTGATATTGTAGCGCAAGTAACAGC (SEQ ID NO:28) |
| | Sp 11 (A) | 2605 to 2580 | Seq/Amp | CCCAAAGGTAGTGTGTATTATTCGCG (SEQ ID NO:29) |
| | Sp 13 (A) | 223 to 198 | Seq | CGTCTCCTTCGTGTGTTG (SEQ ID NO:30) |
| | Sp 14 (A) | 1005 to 988 | Seq | ATCCAAACTCTCTTCGGG (SEQ ID NO:31) |
| | Sp 15 (A) | 2218 to 2199 | Seq | TCGCCCCCGTGGTTAGATAC (SEQ ID NO:32) |
| gE (ORF 68) | Ip2 (A) | 2061 to 2039 | Seq/Amp | CGCTCTAGAACTAGTGGATCCCCCGGGGAATT TGTCACAGGCTTTT (SEQ ID NO:7) |
| | NcogpI (S) | 1 to 11 | Amp | CGACCCGGGGAGCTCCCATGGGGACAGTTAAT AAACC (SEQ ID NO:6) |
| | Sp 1 (S) | 1452 to 1470 | Seq | GCATGTTGAAGCCGTAGCA (SEQ ID NO:33) |
| | Sp 3 (S) | 199 to 217 | Seq | ATGCGCGGCTCCGATGGTA (SEQ ID NO:34) |
| | Sp 4 (A) | 505 to 486 | Seq | GGCCTTGGGGTTTTGGATTA (SEQ ID NO:35) |
| | Sp 6 (S) | −70 to −48 | Seq | GTCCATGGTTTTAGACCTCGGG (SEQ ID NO:36) |
| | Sp 7 (S) | 543 to 561 | Seq | GTTTACTTTACGCGCACCG (SEQ ID NO:37) |
| | Sp 8 (S) | 823 to 840 | Seq | GAATTAGACCCCCCCGAG (SEQ ID NO:38) |

TABLE 1-continued

VZV sequencing and amplification primers

| Protein[1] | Primer[2] | bp[3] | Seq/Amp[4] | Sequence[5] |
|---|---|---|---|---|
| | Sp 9 (S) | 1127 to 1146 | Seq | TAGAGTGGTTGTATGTCCCC (SEQ ID NO:39) |
| | Sp 10 (S) | 1601 to 1619 | Seq | CACTTCTACGATATGCCGC (SEQ ID NO:40) |
| | Sp 12 (A) | 846 to 827 | Seq | TTCAATCTCGGGGGGGTCTA (SEQ ID NO:41) |
| | Sp 13 (A) | 1790 to 1772 | Seq | TCCGTAGATTCCGAGTCCT (SEQ ID NO:42) |
| gL (ORF 60) | P1 (S) | −1 to 16 | Seq/Amp | CAAGCGCCATGGCATCACATAAAT (SEQ ID NO:43) |
| | P2 (A) | 913 to 886 | Amp | AAACACTAGTCCATGTGCATGTCCCGC (SEQ ID NO:44) |
| | Sp 1 (A) | 548 to 530 | Seq | GCTTGCGGGTTTTTTTGGT (SEQ ID NO:45) |
| | Sp 2 (A) | 320 to 302 | Seq | GCCAGCCCCTTTAAGGTGA (SEQ ID NO:46) |
| | Sp 4 (S) | 473 to 494 | Seq | GCCAATGAAATGAAACTATCGG (SEQ ID NO:47) |
| gI (ORF 67) | Scp 1 (S) | −60 to −33 | Seq/Amp | CGGCTCACAGAGCTGCTCTTCGGTGTAG (SEQ ID NO:48) |
| | Scp 2 (A) | 1154 to 1137 | Seq/Amp | TAATCCTTCCCCTCATATCACAACGCGT (SEQ ID NO:49) |
| | Sp 1 (A) | 995 to 978 | Seq | GCGGCCTCCAACATCACA (SEQ ID NO:50) |
| | Sp 2 (A) | 383 to 365 | Seq | CCAGCATCCGGCTCTGTTG (SEQ ID NO:51) |
| | Sp 4 (S) | 314 to 337 | Seq | CGTGTAGGTACAAACATTCGTGGC (SEQ ID NO:52) |
| ORF 47 | ScP 1 (S) | −349 to −320 | Amp | ATCTAATCCGTGGGGGTGCGAGTGTACAAG (SEQ ID NO:53) |
| | ScP 2 (A) | 103 to 132 | Amp | TCCATGTTCGGTGATGTCTTCTGTAGGCGTG (SEQ ID NO:54) |
| | Sp 1 (S) | 3 to 22 | Seq | GGATGCTGACGACACACCCC (SEQ ID NO:55) |
| | Sp 2 (A) | 163 to 182 | Seq | GTTGCAGTTGACGGATTGGC (SEQ ID NO:56) |
| | Sp 3 (S) | 341 to 360 | Seq | TTGTACCCATCTTCACGCTC (SEQ ID NO:57) |
| | Sp 4 (S) | 743 to 762 | Seq | ATCGAACGTGCGGCCTGACC (SEQ ID NO:58) |
| | Sp 5 (S) | 1135 to 1154 | Seq | CTTCCCGGACAACTGCCCAT (SEQ ID NO:59) |
| IE62 (ORF 62) | Scp 1 (S) | −79 to −50 | Seq/Amp | CACCAACCGCAATCGCAATCCTTTGAAGGC (SEQ ID NO:60) |
| | Scp 2 (AS) | 3990 to 3961 | Seq/Amp | TATTAACAACAAACAGTCCGCGCGCCAGTG (SEQ ID NO:61) |
| | Sp 1 (S) | 318 to 342 | Seq | GCCGAGGTCTTCCACACCCGATTCT (SEQ ID NO:62) |
| | Sp 2 (S) | 749 to 773 | Seq | TTTGAAGGTTAAGGTCCCACTCCCG (SEQ ID NO:63) |
| | Sp 3 (S) | 1142 to 1166 | Seq | TACAGGCAGCAGGTCCGGACGCGAA (SEQ ID NO:64) |
| | Sp 4 (S) | 1511 to 1535 | Seq | TTACGAGGCCTCAACGGAACCCGTG (SEQ ID NO:65) |
| | Sp 5 (S) | 1925 to 1949 | Seq | GATCTCCCGCGGTCACCCTTCTCCA (SEQ ID NO:66) |
| | Sp 6 (S) | 2309 to 2333 | Seq | CAAGGCGTACTGTACCCCCGAAACC (SEQ ID NO:67) |
| | Sp 7 (S) | 2685 to 2709 | Seq | ACTCATGCCTGGGCCGGGAACTGGA (SEQ ID NO:68) |
| | Sp 8 (S) | 3098 to 3122 | Seq | CGTCGCATACACCGTGTGTACCCGC (SEQ ID NO:69) |
| | Sp 9 (S) | 3500 to 3524 | Seq | TGCCCTCCCCCCGATTCCCAGAGTA (SEQ ID NO:70) |

[1]The protein that is encoded by the listed ORF.
[2]The designation of the primer.
[3]The base pairs to which the primer hybridizes. The numbering used denotes the transcriptional start site as +1.
[4]Seq, the primer was used as a primer in a sequencing reaction; Amp, the primer was used as a primer in PCR. Some primers were used in both sequencing and amplification.
[5]The nucleotide sequence of the primer, listed 5' to 3'.

Results

Cell-to-cell spread phenotype of VZV-MSP. During the initial assessment of VZV-MSP, it was observed that the egress of VZV-MSP particles in cell culture differed from that of other typical VZV laboratory strains, such as VZV-32 and VZV-Oka. Like other VZV strains, however, infectious virus was not released into the culture medium. The fact that greater numbers of VZV-MSP particles were present on the surface suggested that cell-to-cell spread may be increased. Cell-to-cell spread has been assessed in both herpes simplex virus type 1 (HSV-1) and pseudorabies virus (PRV) through measurement of plaque size in permissive cells or number of cells infected within a typical plaque. Neither technique is easily applicable in the VZV system given the formation of irregularly shaped syncytia by VZV in cell culture and the absence of cell-free virus in tissue culture. Therefore, a technique was developed to assess cell-to-cell spread through confocal microscopic examination.

The spread of low-passage VZV-MSP was compared to the low-passage laboratory strain VZV-32. Human melanoma cells were inoculated with either VZV-32 or VZV-MSP at a 1:8 ratio of infected:uninfected cells. At increasing intervals post-infection, the infected monolayers were probed with an antibody against the VZV immediate early protein 62 (IE 62). The number of cells expressing IE 62 and the intracellular localization of the protein were determined. This assay was based on the observation by Kinchington et al., (*J. Infect. Dis.*, 178 Suppl 1:S16–21 (1998)) that VZV IE 62 is present in the nuclei of infected cells during early stages of infection, but then appears in the cytoplasm during later stages.

At the time point of four hours post-infection, comparing VZV-32 and VZV-MSP by confocal microscopy represents the number of infected cells originally overlaid onto each monolayer. Both monolayers contained similar levels of IE 62 positive cells. At twenty-four hours post-infection the difference in extent of spread between VZV-MSP and VZV-32 was apparent. For VZV-32 at 24 hours, 6–8 cells with advanced infection were present in each focus; EE 62 was present in both nucleus and cytoplasm. A few scattered cells adjacent to the infectious focus contained nuclei with IE 62 concentrated near the membrane; these cells represented a recent transfer of infectivity from the central focus. When the VZV-MSP culture was examined at 24 hours, large syncytia had already formed. A typical syncytium contained 20–30 nuclei, an infectious focus 3 to 4 fold larger than that seen with VZV-32. This experiment was repeated four times with equivalent results.

Quantitative analysis of confocal images of VZV IE 62. To quantify the difference in cell-to-cell spread, multiple confocal images were analyzed with the image analysis programs called Brainvox tal-support programs. Each confocal image is made up of 512×512 pixels, for a total of 262,144 pixels. The green fluorescence channel representing the presence of VZV IE 62 within each confocal image was analyzed. The image analysis program initially assigns a relative signal intensity within each pixel of the confocal image. Then, a threshold of signal intensity is calculated to remove background signals. This analysis facilitated quantification of all pixels within each confocal image that contained IE 62. Thus, confocal microscopy of IE 62 coupled with image analysis facilitated a comparison of the extent of viral spread between two different VZV strains.

Figure 3:
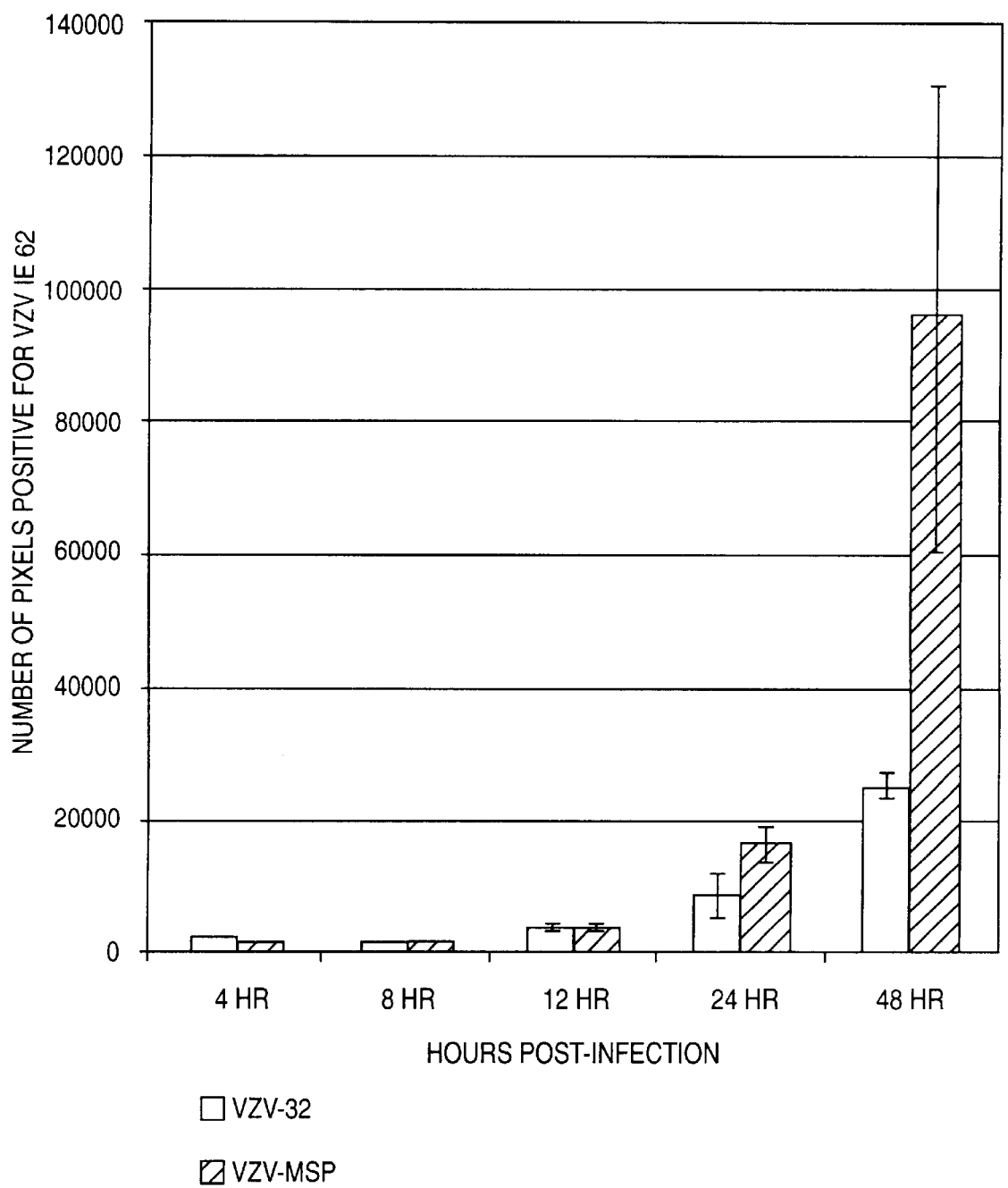
Figure 4:
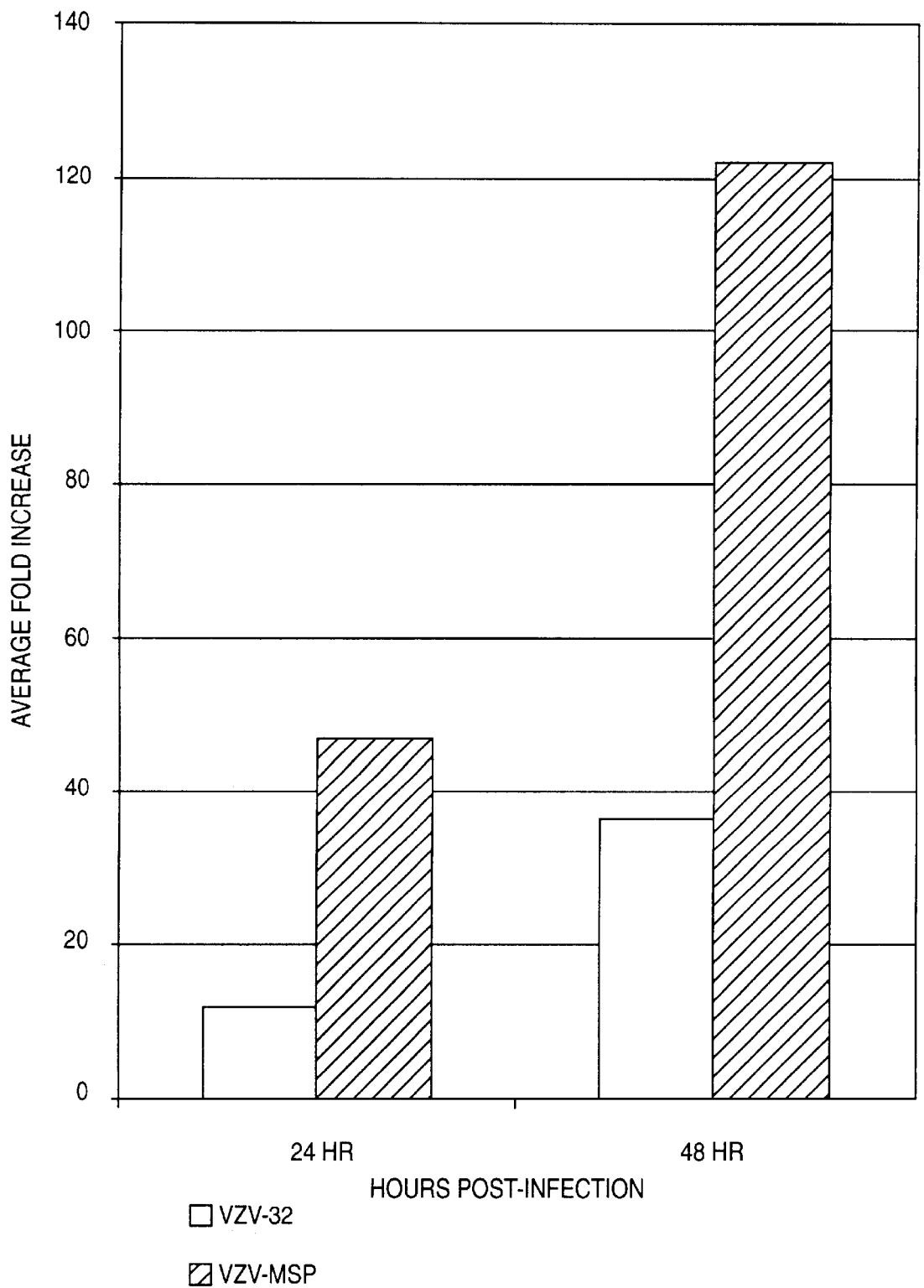

The results for this analysis are shown in FIG. 3. There was no major difference between the extent of IE 62 spread for VZV-32 and VZV-MSP at 4, 8, and 12 hours post-infection. The results at both 4 and 8 hours, in particular, demonstrated that each monolayer was infected with a similar inoculum of infected cells. Also, the lack of a difference between the three time points (4 hours–12 hours) confirmed that the replication cycle for both VZV strains was greater than 12 hours, in agreement with previous studies. However, at twenty-four hours post-infection, there was a noticeable difference between spread of VZV-MSP and VZV-32. The extent of VZV-MSP spread was at least two-fold greater than VZV-32. At forty-eight hours post-infection, this difference increased further, as VZV-MSP spread was four-fold greater than VZV-32. Thus, image analysis provided a new method by which to measure differences in cell-to-cell spread between VZV strains. Again, this methodology is particularly suited for VZV because cell free virus is not released spontaneously from infected cell cultures; even after sonic disruption of infected monolayers, most viral particles remain attached to remnants of outer cellular membranes.

VZV infectious center assays. Because the results in the previous experiments represented a new application of confocal microscopy, a traditional method was also used to confirm the differences in VZV cell-to-cell spread, namely, infectious center assays. For these titrations, the initial virus inocula were replicate samples of VZV-infected cells frozen and stored in liquid nitrogen. After freezing, one aliquot was thawed and titrated from each lot. The inoculum for each 35-mm tissue culture dish was 500 infectious centers. Two dishes were harvested and assayed at each of the following time points: immediately after inoculation (0 hour), 24 hours, and 48 hours post-inoculation (FIG. 4). When comparing the average fold increase of VZV-MSP infectious centers to VZV-32 infectious centers, the spread of VZV-MSP was consistently greater than the spread of VZV-32 over both the first 24 hour period (24 hr pi) and the second 24 hr period (48 hr pi). Otherwise stated, at 48 hours post-infection, the cytopathic effect of VZV-MSP was complete, while numerous infectious center titrations with VZV-32 demonstrated that a 60–72 hr interval was required for similar spread (Grose et al., *Infect. Immun.*, 19:199–203 (1978)). Furthermore, the rapidity of VZV-32 spread was not altered over the initial 20 passages. VZV-Oka and VZV-Ellen titrations exhibited a time course similar to that of VZV-32. Therefore, results from both quantitative confocal microscopic image analyses and infectious center assays documented that the spread of VZV-MSP was 3–4 fold greater than the spread of VZV-32.

Growth of VZV-MSP in the SCID-hu mouse. The SCID-hu mouse has provided the first reproducible animal model of VZV pathogenesis. Published studies have documented the pathology of viral infection in human thymus/liver and skin implants after inoculation with parental and vaccine Oka strains as well as low passage wild type virus (Moffat et al., *J. Virol*, 69:5236–42 (1995), Moffat et al., *J. Virol.*, 72:965–974 (1998)). To assess whether VZV-MSP showed enhanced pathology in the SCID-hu mouse model, skin implants infected with VZV-MSP were harvested at 7, 14, and 21 days after infection. At 7 days post-infection, numerous foci of infection were visible in the epidermis of the human skin implant. By 14 days the foci coalesced into large necrotic lesions with histopathology typical of varicella vesicles. These vesicles were characterized by epidermal hyperplasia, balloon cells, and the separation of the keratin roof from the epidermis. After 21 days, the infection had spread into the dermis and destroyed the entire implant. Samples of the implants also were examined by previously described electron microscopy methods; the virion formation closely resembled that shown in FIG. 2 of the report by Moffat et al., (*J. Virol.*, 72:965–974 (1998)). Mock infected skin implants showed normal skin structure consisting of a thin layer of keratinocytes above the dermis and hair follicles.

Prior published studies had not shown such a rapid progression of pathology in the SCID-hu mouse infected with VZV. To further assess this aspect of VZV infection in the animal model, another experiment was performed with a clinical isolate passaged even fewer times than VZV-32; in addition, the low passage parent VZV-Oka strain was included. Again, the skin samples were collected and examined at days 7, 14, and 21 post-inoculation. When all the specimens were reviewed, the histopathology of the clinical isolate and parental VZV-Oka at 21 days post-inoculation were similar, and for both strains the histopathology was approaching that caused by VZV-MSP at 14 days post-inoculation. Even at 21 days, however, the former two viral strains never caused the total destruction seen after VZV-MSP infection. In short, the progression of VZV-MSP through the skin implant was noticeably more extensive than seen with other viral strains tested in the SCID-hu animal model.

Genetic analysis of other major glycoproteins of VZV-MSP. After documenting the enhanced cell-to-cell spread of VZV-MSP, it was determined whether mutations were present in ORFs other than gE that may be contributing to this phenotype. Specifically, ORFs 31, 37, 60, and 67 coding for VZV gB, gH, gL, and gI, respectively, were analyzed. The ORFs were amplified from the VZV-MSP viral genome and sequenced, then compared to the published VZV-Dumas sequence. Neither gI nor gL gene contained any nucleotide differences when compared to the nucleotide sequences of VZV-Dumas. Further, the gB sequence was identical to that of VZV-Dumas. However, VZV-MSP gH contained a single point mutation within codon 269 (CCA→CTA), converting a proline residue in the predicted VZV-Dumas peptide sequence to a leucine residue in VZV-MSP gH.

Figure 5:
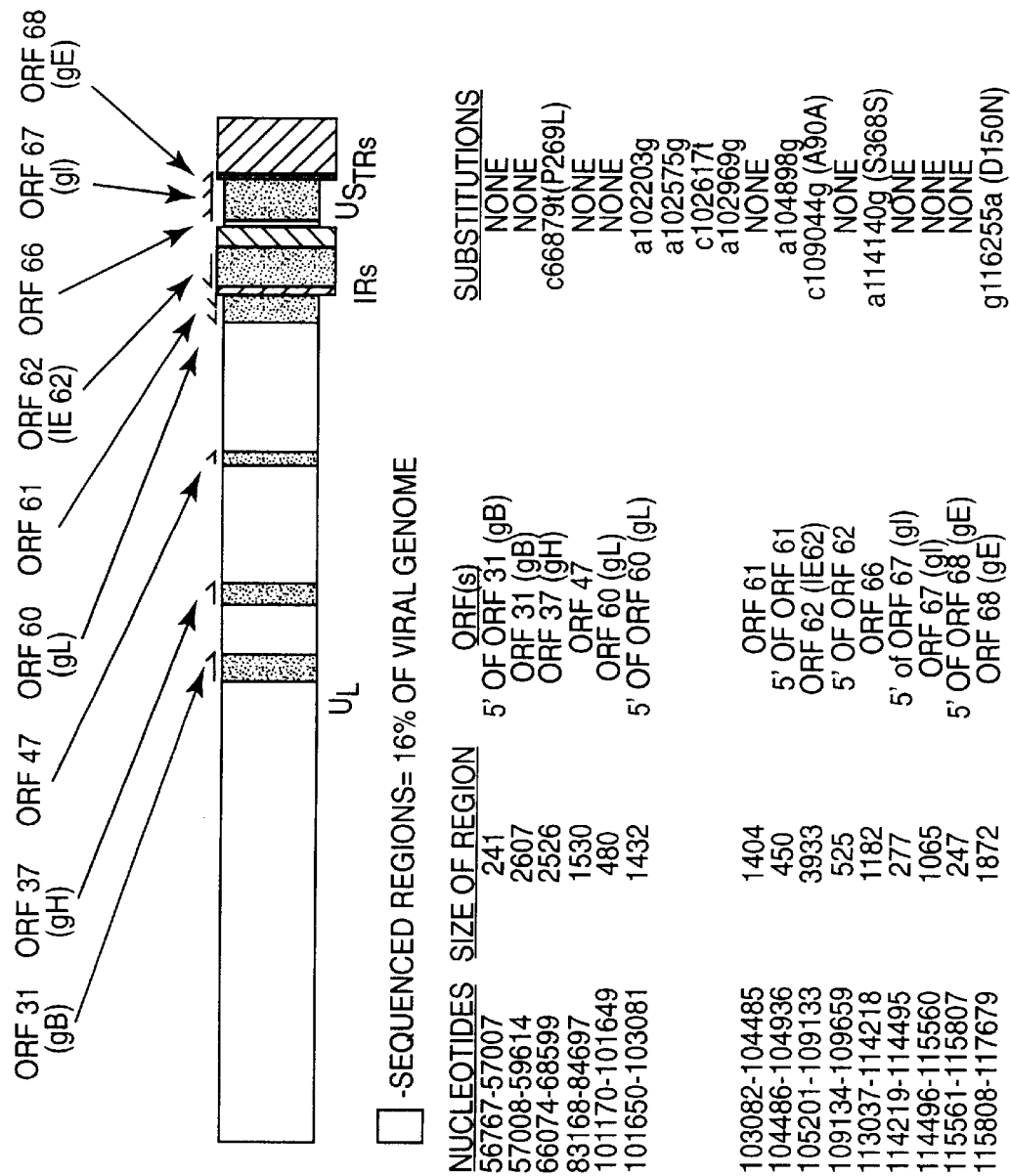

Given the presence of mutations within VZV-MSP gE and gH, a similar genetic analyses of VZV-32 was performed. As expected, VZV-32 lacked the D150N mutation within gE. VZV-32 gH, however, revealed the identical point mutation found within codon 269 of VZV-MSP gH. Thus, the mutation within VZV-MSP gH cannot account for the VZV-MSP cell-spread phenotype. VZV-32 contained one additional mutation within ORF 67 (gI) which would lead to a Q5H substitution (CAA→CAT). This substitution was within the probable leader sequence of VZV gI and thus would not be present in mature gi (Davison et al., *J. Gen. Virol.*, 67:1759–816 (1986)). Altogether, within five major glycoprotein ORFs, VZV-MSP contained two point mutations which caused amino acid substitutions when compared to VZV-Dumas: D150N in gE, and P269L in gH (FIG. 5).

In addition to 5 ORFs, we sequenced major portions of the 5' untranslated regions of ORFs 31, 60, 67 and 68. All regions were identical to VZV-Dumas except for that of ORF 60. The latter region contained four polymorphisms; these ranged from 554 to 1320 nucleotides from the ORF 60 initiation codon (FIG. 5). It is very unlikely that these polymorphisms will alter the expression of gL since they are located over 500 nucleotides upstream of the gL start site.

Genetic analysis of VZV-MSP regulatory proteins and kinases. Although viral glycoproteins are the most likely candidates for mediating the cell-to-cell spread phenotype of VZV-MSP, we considered the possibility that an alteration in immediate early (IE) regulatory events may contribute to this enhanced cell-to-cell spread phenotype. VZV expresses one predominant species, IE 62, which acts as the major regulatory protein for viral gene expression. This protein contains a potent acidic activation domain at its N-terminus and is a component of the virus particle. Therefore, the IE 62 gene of VZV-MSP was sequenced, but detected only one silent polymorphism within codon 30 when compared to the Dumas strain (GCG→GCC) (FIG. 5). Thus, the peptide sequence of VZV-MSP IE 62 was identical to the predicted VZV-Dumas sequence. Further, we sequenced the 5' untranslated region containing 525 nucleotides and this region was identical to VZV-Dumas. In addition, we sequenced the adjacent VZV-MSP ORF 61, which encodes the functional homolog of HSV-1 ICP0. Again, the nucleotide sequence was identical to VZV-Dumas.

Previous studies have shown that the viral protein kinase VZV ORF 47 can phosphorylate IE 62 (Ng, et al., 1994). Also, VZV ORF 66 encodes a protein kinase which has been shown to affect the intracellular localization and transactivation function of IE 62. Based upon these results, we wanted to determine whether mutations in these viral kinases could affect the function of IE 62 within VZV-MSP infected cells. Therefore, we sequenced both protein kinase genes within the VZV-MSP genome and found both to be identical to the prototype VZV-Dumas sequence (FIG. 5). Thus, there was no genetic evidence of polymorphisms within either of two regulatory ORFs or either of two viral protein kinase ORFs. In short, after sequence analysis of over 15% of the VZV-MSP genome, the main impression was a striing similarity with VZV-Dumas except for the notable exceptions mentioned earlier.

EXAMPLE 3

Single Nucleotide Polymorphisms in Major Open Reading Frames of other Varicella Zoster Viruses Materials and Methods Viruses. VZV-MSP was isolated in Minnesota in late 1995. VZV-32 was isolated in Texas in the 1970s. VZV-Oka was isolated in Japan and attenuated in the 1970s. VZV-VSD was a wildtype virus collected in South Dakota in the 1980s. VZV-VIA was isolated in Iowa from a child with chickenpox in the 1990s. VZV-Iceland was isolated in Iceland from vesicle fluid of a child with chickenpox in the 1990s. VZV-Ellen was originally isolated in Georgia from a child with chickenpox in the 1960s and obtained from the American Type Culture Collection. VZV 80-2 was originally isolated in Pennsylvania from an adult with herpes zoster in the 1980s.

Propagation of viruses. All viral strains except VZV 80-2 virus were propagated in human melanoma cells (MeWo strain). Transfer of infectivity was performed by inoculation of trypsin dispersed infected cells onto an uninfected monolayer at a 1:8 ratio. Each 25 cm$^2$ VZV- infected monolayer was allowed to incubate until cytopathology reached 80%. The monolayer was then washed thrice with 5 ml of 0.01 M phosphate buffered saline (PBS) of pH 7.4. Cells were dislodged by scraping into 0.5 ml PBS. Viral DNA was collected from the cells using the DNeasy Tissue Kit following the DNeasy Protocol for Cultured Animal Cells (Qiagen Inc). Collected DNA was cleaned by placing on a Microcon 50 filter and washing twice with 0.5 ml of Nanopure water. (Bamstead/Thermolyne). Viral DNA was resuspended in 100 μl of Nanopure water. The VZV 80-2 viral genome DNA was present in two cloned restriction enzyme libraries prepared by Ecker et al., (*Proc. Natl. Acad. Sci. USA*, 79:156–160 (1982)).

PCR amplification and sequencing of viral DNA. PCR amplification was performed with primers flanking the region of interest (Table 1). The Expand High Fidelity PCR System was used in the PCR amplification procedure (Roche Molecular Biochemicals). This system includes Taq DNA and Pwo DNA polymerases, with the 3'–5' proofreading activity of the Pwo DNA polymerase to increase the fidelity (Roche Molecular Biochemicals). Electrophoresis of each sample was carried out in a 1% agarose gel to determine concentration. The DNA sequencing reactions were performed using dye terminator cycle sequencing chemistry with AmpliTaq DNA polymerase, FS enzyme (PE Applied Biosystems, Foster City, Calif.). Reactions were run and subsequently analyzed with an Applied Biosystems Model 373A stretch fluorescent automated sequencer at the University of Iowa DNA Facility. Sequences were further analyzed using the program DNASIS V2.0 (Hitachi Software Engineering Co.). Any region of a VZV genome which differed in sequence from that of the prototypic VZV Dumas was re-amplified in a second PCR step and subjected to a second sequencing analysis.

Results
Polymorphisms in the VZV gE Gene

The VZV gE gene was of greatest interest because of the discovery of the gE mutant strain VZV-MSP. Surprisingly, six gE polymorphisms were found among the eight tested strains and isolates, four of which caused amino acid substitutions (FIG. 6). However, none of the tested strains contained the D150N mutation within the 3B3 epitope of VZV-MSP. VZV-Ellen, VZV-Iceland, and VZV 80-2 had three identical polymorphisms. One was a synonymous mutation within codon 220. Two non-synonymous mutations in these three strains caused amino acid substitutions within codons 40 (T→I) and 536 (L→I). The vaccine strain VZV-Oka also contained the mutation within codon 40, but lacked the other two mutations found within VZV-Ellen, VZV-Iceland, and VZV 80-2. VZV-VSD was the only strain tested which contained a polymorphism within the gE cytoplasmic domain of gE. Interestingly, this change within codon 603 (G→D) inserted an additional acidic amino acid adjacent to the acidic casein kinase II phosphorylation site of gE. VZV-32 and VZV-VIA were the only strains tested that did not contain gE substitutions when compared to the Dumas strain. Since the mutations previously found in VZV-MSP gE were not discovered in any other strain, VZV-MSP gE retained a unique sequence among all currently tested strains and isolates.

Polymorphisms in the VZV gI Gene

The discovery of several polymorphisms in the gE gene of the 8 strains was unexpected. Since VZV gE and gI proteins are commonly found in a complex in the infected cell culture, the gI gene was the next obvious candidate for further genetic analysis. Sequencing of ORF 67 led to the discovery of two changes from the published Dumas sequence (FIG. 7). VZV-32 had an A to C substitution at bp 15 of the ORF that resulted in a glutamine to histidine substitution. VZV Oka also had a silent change of G to A at bp 546. The number of gI sequence variants was less than that seen with gE and may suggest that gI function requires a more rigid amino acid sequence.

Polymorphisms in the VZV gH Gene

Next to the VZV gE:gI complex, the gH:gI complex has been most extensively studied because of its role in cell-to-cell fusion. Overall, the eight strains contained nine polymorphisms, three of which caused amino acid substitutions (FIG. 8). Again, VZV-Ellen, VZV-Iceland, and VZV 80-2 were remarkably similar, with identical changes within codons 76 (R→K) and 700 (R→K) as well as silent substitutions within codons 13, 676 and 727. VZV-Ellen possessed a unique polymorphism within codon 418 that allowed differentiation from VZV-Iceland and VZV 80-2. VZV-32 and VZV-VIA both contained a silent change within codon 815 not present in any other tested strain. VZV-MSP contained only the P269L polymorphism shared by seven strains, including VZV-32.

Polymorphisms in the VZV gL Gene

In a manner similar to gE and gI, gL is invariably linked with the gH protein in VZV-infected cultures. For this reason, the gL ORF was a another candidate gene for sequence analysis. The result was striking: only VZV-Oka gL gene differed from prototype Dumas gL gene (FIG. 9). The first change included the insertion of a methionine codon between amino acids 9 and 10. Secondly, there was a G to A substitution at bp 320 of VZV-Dumas that resulted in a glycine to aspartic acid change in the protein. The fact that the gL genes from the 7 other strains were identical to the prototype gL gene may suggest, as with the gI protein, that gL function requires a protein that is restricted in its genetic variability.

Polymorphisms in the VZV gB Gene

The gB gene is one of the most conserved genes among all herpesviruses. In the case of VZV, this protein is important in the infectious cycle of the virus, based on the previous evidence that addition of anti-gB monoclonal antibody to an infected culture inhibits the progression of infection (Montalvo et al., *J. Virol.*, 61:2877–2884 (1987)). Of the eight strains in which gB was sequenced, 7 were identical to the prototype Dumas gB gene. As with the gL gene, only the Oka gB gene was different from Dumas. The Oka gB had three alterations: an A to C change at bp 217, which led to an amino acid substitution of a threonine to a proline at residue 73; a G to T change at bp 391 resulting in a aspartic acid to a tyrosine substitution at amino acid 131; finally, a silent change of A to C at bp 294. In short, the sequence of gB was highly constrained.

Polymorphisms in the VZV IE62 Gene

The fact that polymorphisms were easily discernible in the major glycoprotein structural genes led to examining whether a similar situation existed in the major VZV regulatory gene called IE62. Overall, 38 polymorphisms were found in the IE 62 gene of the eight tested strains, when compared to the VZV-Dumas IE 62 gene (FIG. 10). As was the case with the gE and gH gene sequences, VZV-Ellen, VZV-Iceland, and VZV 80-2 showed remarkable similarity in their IE 62 genes. Identical silent substitutions within IE 62 were present in these strains at codons 61, 129, and 1071. Also, these three strains contained an identical polymorphism at codon 703 (V→A). VZV-Oka was similar to these three strains, as it shared the silent IE 62 substitutions within codons 61 and 129, but lacked the change at codon 1071. VZV-Oka shared additional polymorphisms with VZV-Ellen at codons 341 and 958 (R→G) that were not present in VZV-Iceland and VZV 80-2. VZV-Ellen revealed nine unique substitutions in addition to those shared with VZV-Iceland, VZV 80-2 and VZV-Oka.

VZV-32 and VZV-VIA both contained identical polymorphisms within IE 62 at codons 516,1057 (Q→R), 1072 (Q→R), 1080, and 1241. VZV-32 also contained five unique changes as well as containing the R958G mutation found in VZV-Ellen and VZV-Oka. VZV-VIA revealed four unique polymorphisms, which combined with the unique changes within VZV-32 allow differentiation of VZV-32 and VZV-VIA. VZV-VSD contained one unique substitution (A→V at codon 602) but otherwise was identical to the Dumas strain. Overall, numerous mutations were found within IE 62 among the tested VZV strains. However, VZV-MSP IE 62 contained no polymorphisms, other than the synonymous substitution found within codon 30, when compared to the Dumas strain. Thus, there was no genetic evidence that IE62 contributed to the VZV-MSP phenotype Polymorphisms in the VZV Protein Kinase Gene The VZV genome encodes at least two putative protein kinases, one in the UL region (ORF 47) and the second in the US region of the genome (ORF 66). The ORF 47 kinase is known to phosphorylate the IE62 gene product. Sequencing of the ORF47 protein revealed two variations from Dumas. VZV Ellen, Oka and Iceland shared a silent A to G transition at nucleotide 1449. VZV Ellen had a unique transversion of T to C at nucleotide 913, which caused an amino acid change from serine to proline. The VZV 80-2 gene 47 was not sequenced because neither cloned VZV DNA library contained a complete ORF (Ecker et al., *Proc. Natl. Acad. Sci. USA*, 79:156–160 (1982)).

Transitions Versus Transversions

Mutations that result in the substitution of a pyrimidine for a pyrimidine or a purine for a purine are called transitions. Substitutions of a purine for a pyrimidine and vice versa are transversions. Transversions are much less common than transitions in the human genome. When the number of transitions and transversions were counted for the sequenced VZV genes, 78% were transitions. Interestingly, all three substitutions in gB were transversions. This result was in contrast with the other genes. The gE gene had 1 transversion and 5 transitions. The gH gene had 3 transversions and 6 transitions. The gI gene had 1 transversion and 1 transition. The gL gene had 6 transitions. The ORF 47 gene had 2 transitions. The IE62 gene had 5 transversions and 33 transitions. Even though there were many polymorphisms in some IE62 genes, the fact that the IE62 gene of the VZV-MSP strain differed by only one transversion from VZV-Dumas should be noted.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

| Sequence Listing Free Text | |
|---|---|
| SEQ ID NOs:1–71 | Oligonucleotide primer |
| SEQ ID NO:75 | Portion of polypeptide encoded by VZV-MSP ORF68 |

What is claimed is:

1. An isolated polynucleotide comprising the nucleotide sequence of nucleotides 115,808 to 117,679 of SEQ ID NO:76, with the proviso that nucleotide 116,255 is an adenine.

2. The polynucleotide of claim 1 wherein the polynucleotide is isolated from a varicella zoster virus.

3. An isolated polynucleotide consisting essentially of the nucleotide sequence of nucleotides 115,808 to 117,679 of SEQ ID NO:76, with the proviso that nucleotide 116,255 is an adenine.

* * * * *

UNITED STATES PATENT AND TRADEMARK OFFICE
CERTIFICATE OF CORRECTION

PATENT NO.      : 6,528,066 B1
DATED           : March 4, 2003
INVENTOR(S)     : Grose et al.

It is certified that error appears in the above-identified patent and that said Letters Patent is hereby corrected as shown below:

Column 8,
Line 4, please delete "other wise" and insert -- otherwise --.

Column 19,
Line 35, please delete "AvaII" and insert -- AvaII --.

Column 22,
Line 50, please delete "subdloning" and insert -- subcloning --.

Column 23,
Line 21, please delete "S4000" and insert -- S-4000 --.

Column 34,
Line 6, please delete "striing" and insert -- striking --.

Column 36,
Line 54, please delete "linases" and insert -- kinases --.

Signed and Sealed this

Twenty-second Day of July, 2003

JAMES E. ROGAN
*Director of the United States Patent and Trademark Office*

SEQUENCE LISTING

```
<160> NUMBER OF SEQ ID NOS: 80

<210> SEQ ID NO 1
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 1
cgatgacaga cataaaattg taaatgtga                                            29

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 2
cacccaagta ttgtttttct gtccg                                                25

<210> SEQ ID NO 3
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 3
cgatgacaga cataaaattg taaatgtgg                                            29

<210> SEQ ID NO 4
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 4
catactgtgt cgaccaaagg caatacggtg acgtg                                     35

<210> SEQ ID NO 5
```

```
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 5
ttgcctttgg tcgacacagt atgcgattgt gatag                              35

<210> SEQ ID NO 6
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 6
cgacccgggg agctcccatg gggacagtta ataaacc                            37

<210> SEQ ID NO 7
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 7
cgctctagaa ctagtggatc ccccggggaa tttgtcacag gctttt                  46

<210> SEQ ID NO 8
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 8
ggcgttttca taacctccgt tacggggg                                      28

<210> SEQ ID NO 9
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 9
ccctgtgatg cgtaatggag acacatga                                      28

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 10
ctttgtaata taccgtcgcc                                               20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
```

-continued cgtacgatta gaaccaactc                                                    20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 12
ggcatactac caatgacacg                                                    20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 13
agtggcgtga ggttgaagac                                                    20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 14
cacccgactc gaaataccag                                                    20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 15
tctggtagta ctacgcgttg                                                    20

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 16
gactacagtg aaattcaacg ccg                                                23

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 17
cccgatgaag gcattatatc c                                                  21

<210> SEQ ID NO 18
<211> LENGTH: 20
<212> TYPE: DNA

```
<213> ORGANISM: Artificial Sequence
<220> FEATURE:
<223> OTHER INFORMATION: Oligonucleotide primer

<400> SEQUENCE: 18
tagctggcac cacgacgagg                                              20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 19
tgcgaacacg ggagtatcct                                              20

<210> SEQ ID NO 20
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 20
ctgctcttct acgagaatat tccgaccg                                     28

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 21
cgtgttttct atcatttccc cagtg                                        25

<210> SEQ ID NO 22
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 22
actacgttcc caccaaaccc ccttg                                        25

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 23
gcggttacaa gcgacaccac atgg                                         24

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 24
ctgttagatg agatcgtaga tgttcag                                      27
```

```
<210> SEQ ID NO 25
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 25
gctacagaga ggcaggct                                              18

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 26
ttgcataccc aactagacga atctg                                      25

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 27
tagagacggt cgcactgccc catc                                       24

<210> SEQ ID NO 28
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 28
cggtgatatt gtagcgcaag taacagc                                    27

<210> SEQ ID NO 29
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 29
cccaaaggta gtgtgtatta ttcgcg                                     26

<210> SEQ ID NO 30
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 30
cgtctccttc gtgtgttg                                              18

<210> SEQ ID NO 31
<211> LENGTH: 18
<212> TYPE: DNA
<213> ORGANISM: Artificial Sequence
<220> FEATURE:
```

-continued

<223> OTHER INFORMATION: Oligonucleotide primer

<400> SEQUENCE: 31
atccaaactc tcttcggg                                    18

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 32
tcgcccccgt ggttagatac                                  20

<210> SEQ ID NO 33
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 33
gcatgttgaa gccgtagca                                   19

<210> SEQ ID NO 34
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 34
atgcgcggct ccgatggta                                   19

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 35
ggccttgggg ttttggatta                                  20

<210> SEQ ID NO 36
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 36
gtccatggtt ttagacctcg gg                               22

<210> SEQ ID NO 37
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 37
gtttacttta cgcgcaccg                                   19

<210> SEQ ID NO 38
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 38
gaattagacc cccccgag                                                 18

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 39
tagagtggtt gtatgtcccc                                               20

<210> SEQ ID NO 40
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 40
cacttctacg atatgccgc                                                19

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 41
ttcaatctcg gggggtcta                                                20

<210> SEQ ID NO 42
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 42
tccgtagatt ccgagtcct                                                19

<210> SEQ ID NO 43
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 43
caagcgccat ggcatcacat aaat                                          24

<210> SEQ ID NO 44
<211> LENGTH: 27
<212> TYPE: DNA
<213> ORGANISM: Artificial Sequence
<220> FEATURE:
<223> OTHER INFORMATION: Oligonucleotide primer -continued

```
<400> SEQUENCE: 44
aaacactagt ccatgtgcat gtcccgc                                           27

<210> SEQ ID NO 45
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 45
gcttgcgggt tttttggt                                                     19

<210> SEQ ID NO 46
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 46
gccagcccct ttaaggtga                                                    19

<210> SEQ ID NO 47
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 47
gccaatgaaa tgaaactatc gg                                                22

<210> SEQ ID NO 48
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 48
cggctcacag agctgctctt cggtgtag                                          28

<210> SEQ ID NO 49
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 49
taatccttcc cctcatatca caacgcgt                                          28

<210> SEQ ID NO 50
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 50
gcggcctcca acatcaca                                                     18

<210> SEQ ID NO 51
<211> LENGTH: 19
```

```
<212> TYPE: DNA
<213> ORGANISM: Artificial Sequence
<220> FEATURE:
<223> OTHER INFORMATION: Oligonucleotide primer

<400> SEQUENCE: 51
ccagcatccg gctctgttg                                              19

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 52
cgtgtaggta caaacattcg tggc                                        24

<210> SEQ ID NO 53
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 53
atctaatccg tggggtgcg agtgtacaag                                   30

<210> SEQ ID NO 54
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 54
tccatgttcg gtgatgtctt ctgtaggcgt g                                31

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 55
ggatgctgac gacacacccc                                             20

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 56
gttgcagttg acggattggc                                             20

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 57
```

-continued ttgtacccat cttcacgctc                               20

<210> SEQ ID NO 58
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 58
atcgaacgtg cggcctgacc                               20

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 59
cttcccggac aactgcccat                               20

<210> SEQ ID NO 60
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 60
caccaaccgc aatcgcaatc ctttgaaggc                    30

<210> SEQ ID NO 61
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 61
tattaacaac aaacagtccg cgcgccagtg                    30

<210> SEQ ID NO 62
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 62
gccgaggtct tccacacccg attct                         25

<210> SEQ ID NO 63
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 63
tttgaaggtt aagtcccac tcccg                          25

<210> SEQ ID NO 64
<211> LENGTH: 25
<212> TYPE: DNA
<213> ORGANISM: Artificial Sequence

```
<220> FEATURE:
<223> OTHER INFORMATION: Oligonucleotide primer

<400> SEQUENCE: 64
tacaggcagc aggtccggac gcgaa                                          25

<210> SEQ ID NO 65
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 65
ttacgaggcc tcaacggaac ccgtg                                          25

<210> SEQ ID NO 66
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 66
gatctcccgc ggtcaccctt ctcca                                          25

<210> SEQ ID NO 67
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 67
caaggcgtac tgtacccccg aaacc                                          25

<210> SEQ ID NO 68
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 68
actcatgcct gggccgggaa ctgga                                          25

<210> SEQ ID NO 69
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 69
cgtcgcatac accgtgtgta cccgc                                          25

<210> SEQ ID NO 70
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 70
tgccctcccc ccgattccca gagta                                          25
```

-continued

<210> SEQ ID NO 71
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 71
aagctccaag tctcggtgta cc 22

<210> SEQ ID NO 72
<211> LENGTH: 350
<212> TYPE: PRT
<213> ORGANISM: VARICELLA ZOSTER

<400> SEQUENCE: 72
```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320
```

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val
            340                 345                 350

<210> SEQ ID NO 73
<211> LENGTH: 13
<212> TYPE: PRT
<213> ORGANISM: VARICELLA ZOSTER

<400> SEQUENCE: 73

Val Asp Gln Arg Gln Tyr Gly Asp Val Phe Lys Gly Asp
1               5                   10

<210> SEQ ID NO 74
<211> LENGTH: 39
<212> TYPE: DNA
<213> ORGANISM: VARICELLA ZOSTER

<400> SEQUENCE: 74
gtggaccaac gtcaatacgg tgacgtgttt aaaggagat                            39

<210> SEQ ID NO 75
<211> LENGTH: 39
<212> TYPE: DNA
<213> ORGANISM: VARICELLA ZOSTER

<400> SEQUENCE: 75
gtgaaccaac gtcaatacgg tgacgtgttt aaaggagat                            39

<210> SEQ ID NO 76
<211> LENGTH: 124884
<212> TYPE: DNA
<213> ORGANISM: Varicella zoster

<400> SEQUENCE: 76
aggccagccc tctcgcggcc ccctcgagag agaaaaaaaa aagcgacccc acctccccgc      60
gcgtttgcgg ggcgaccatc ggggggggatg ggattttttg ccgggaaacc cccccccgcc    120
agcctttaac aaaacccgcg ccttttgcgt ccacccctcg tttactgctc ggatggcgac    180
cgtgcactac tcccgccgac ctgggacccc gccggtcacc ctcacgtcgt ccccccagcat   240
ggatgacgtt gcgaccccca tccctacct acccacatac gccgaggccg tgcagacgc     300
gccccccccct tacagaagcc gcgagagtct ggtgttctcc ccgcctcttt ttcctcacgt   360
ggagaatggc accacccaac agtcttacga ttgcctagac tgcgcttatg atggaatcca    420
cagacttcag ctggcttttc taagaattcg caaatgctgt gtaccggctt ttttaattct    480
ttttggtatt ctcaccctta ctgctgtcgt ggtcgccatt gttgccgttt ttcccgagga    540
acctcccaac tcaactacat gaaactactg tccggaaggg aaggtatt attctcgctt       600
gcagcttgtc gcgcgtgtat gcacaacaaa agctatatat gtcaccaaag ccaacgtcgc     660
catctggagt actacaccca gtacgttgca taacctgtcc atttgcattt tcagttgcgc     720
ggacgccttt ctccgggatc gtggccttgg acatcaacc agtggaataa gaaccgccgg     780
tggtcttgtt tgaacgacga gtggcgacgc gttgttctgc ataagctctg tatgctgata    840
cataaacaca gagtctgtat cgctatcaga ttcccgaaca ccttccggta ccccatactc    900
cgatacccctg gacattgcgg atcccaaaaa tataatatta acaggatttg cttatacttt   960
gctacagctt atataaattt atgtgcgata catcttaagt gcatccgtac gttatttata  1020

```
cattgcctgt cacgtgaaaa gactgtgtta cccaataaag gttctacaaa aaatgcttta   1080
ttgggtgttt gtttaatagc tattatcgta acccaccccc gtaaaatcat aaaatgcatg   1140
taatttctga gacacttgca tatgggcatg ttcccgcatt tattatgggc tccactctgg   1200
tgcgtcccag tttaaacgcc accgccgagg aaaatcccgc gtcagaaacg cgatgtttat   1260
tacgagtgct tgcggggaga actgtagacc tgccaggcga aggaacgtta cacattacct   1320
gtaccaaaac ctatgtaatt attggcaaat atagcaaacc cggcgaacgt cttagccttg   1380
cccgtctaat agggcgtgca atgacgcctg gaggtgcaag gacatttatt attttggcga   1440
tgaaggaaaa gcgatccaca acgcttgggt atgaatgtgg tacgggcttg catttactgg   1500
ctccatctat gggtacattt ctccgcacac acggtttaag taacagagat ctctgtttat   1560 ggcgggtaa tatttatgat atgcatatgc aacgtcttat gttttgggag aatatcgcgc   1620
aaaataccac tgaaacacct tgtataacgt cgacgttaac atgcaacttg acagaagact   1680
ctggtgaagc cgcacttacc acgtcagacc gacccactct cccaaccccta acagcccaag   1740 gaagaccaac agtttccaac attcgtggaa tattgaaagg atcccccgt caacagccgg   1800 tctgtcaccg ggttagattt gccgaaccta cggagggcgt attgatgtaa tcactaaata   1860
aaatacacct tttttcgatt gtacgtattt ttatttaaat gtgtagttca tagtccgccg   1920
acagccgctc gggcttttcc cccacataca acatgatcgt atgcctcgga tgcaccggtc   1980
caacactccg ccgagaaggg ggatttacaa tgacagtgat acccaatagc cgccagatgt   2040
acacccagct gtccggactc cagcatcatc tgctgagttg cggcgctgaa gggtgcatcg   2100 cataggggtgt tataattagc catttccggt aacagtcgtt gggaatttag gaggctgcaa   2160
aacggctgta ggtcaacata cattggggat tcagatggtt tatctcgacg tccaagtcca   2220
atcaaaaaag cgtgtaaatc atcagcccgg ccgcatgttg ctcgaagagc ataaacctc   2280 ttaacaccgt acagagggga tggcgtcggt gcatgtgagt tggcagggca tgtccacgtt   2340
gtttccaacg ccagtggcgg tataacttgt gtaaacgacg ccaacgggtc aggtttaaga   2400
ttcactcgga tgggttgact gctttcggaa gctcccgttg tatccattaa ttaaacgttc   2460
ggtacacgtc tggtgtgtgt tttacccgaa tcagagacgg aattgcaaag atattggttt   2520
gaaagcaatg taatcccgcc catatatccc caacgtcgcc ttaaaaactc ccacaatatt   2580
acatttttat tagtctttta ttaatataga atcacataaa caattgataa aatcaagggg   2640
tggtgtataa tgattaaaaa tataaattga tatgttttac aagcatgaaa taggtattta   2700
ctattctaac aggtaaatat gcttaatgat taaaaataca aattagtatg ttttgacaag   2760
catgaaaaag gtatttttta ttttagcagt taaaggtact acacttaaaa tatttaccgt   2820
atggacgggc gtcagaaaga tgcccggccc aagttgagag ggtacattca acacgaccac   2880
actcgcgttg gtgggtgatt agggcctcta aaacaccggc cagacatgac ccgggtgtat   2940
attcttgtaa cacttgaacg ttacaactga tatcatcata ttccacaaat ttagagccac   3000
ggacaactat attagcaatg cggcaatca taacaaacat ataagtagta atacacgtga   3060
tatcactaaa acgttgctgg cgcaacagtt cggggagagt acgagacccc aaatcgttgt   3120
ccctgtttag aagaagacat cttacaaaag gccccagctt taactttaaa ttctccaaaa   3180
gtgacttcga ggttgcaaca atgggattat ttgtgtagat gggcaagttt tttgccgcta   3240 acatttttaat ccacgttaac agttcatccg cagactccaa cgcttcaatc aaagattctc   3300
cacgtatgac tctctcacgc aacgcgcggg caatacgtga gtccattta tatgactcaa   3360
```

-continued

```
aggtacgata aagttcatgt ccgtacaaca tcaactccgg ccaagatgtg ttttgtttta    3420
tccccggaaa acatccaccg gaagcccatg aatcaccctc ttgtattgtg gcatatcgga    3480
ctaccagttt ttcaattgtt tcatctaaat ggcgtaccga gtcaatggtc acgctggctc    3540
ccgcggtgga gacgacttca atagcacggc ccgtaattcg atcgaccggg atatcatact    3600
cttttcgaat acgctctcgg cgggcgtctc tcttggaaaa tcgcaacctg tacgattcgt    3660
catgtgtctg atcatttctt tctcccgtgg tcattgcagg aggcgttgta ggacgccgtc    3720
ttcgatttga cagggatcga tcacggtgtt ttcttgaact ttgagtgtta taagatctgg    3780
atgatcgtcg atgtccccgt tcgatgcgtg catatccagt ctccacgtct cttcctccat    3840
gatggtttga atcgggtaat acaacaacca aagttttcgg gcgattgtgg tggtagcttt    3900
cacgccttcc gtgccttcgt ttggaatacc gtggattata tgctgtatct gcagtacgct    3960
ccacatacac agttctagac gttgtggagt cctcgcctgg agtggagcca atagcttcat    4020
catttgccca atcggtgact tccaatgcaa agtcatccga aggttcgtct ggtagcaaat    4080
tcataaagtc ttcacaaata gtagacacgt ctgggtcggt tggaattgaa gcagaggcca    4140
tggctgcaaa atatctgaca attgcgtgtt tgcagttgcc tgtatcttcc gccaatgttg    4200
tagaatttat aggctcaccc aaccccgcaa tgggcgtgtt tagtcacatg attaatgctt    4260
ctgggagttt tcactttccc caaacaagct tacctgcacc ctttgttcgt aatgcataaa    4320 ataaccact gctatagcaa atatgacgat ataaaaacat tttatagcaa ggccggacat    4380
tactgtagcg caacatgttg tgcatatacc acgtattccc cccgtattga tatgatttaa    4440
atgattatcc ttggttggtt ttggtctaac ataagatata agctctacta tagcgagcgt    4500
gcatacaaca acccaggcca gaatccgaat gtatgtgggg tataataacg cgcatggtgt    4560
atatgcaacg ccaagcgtta aaagcacaat acatccagat gatatatgag cgataacctc    4620
caaaagcatc aataacgtaa caacctttatg catatataaa aaacttatag ggtcagcatt    4680 aaatactttta ctcataccat cccgtcgcat ggaaacatca cataacaacc ttgccaactt    4740
tgtatatggg taaccaagaa gaatgttcga aataacccgt gttacgtaat tcagtgaata    4800
tgatgtgggg gatattaact cacaggatga tcggaatggc ccaaacatac gacgtattcg    4860
tcgaaattgt aaatacatac catatacaaa ccatgcaaaa aaaatcattt ttagctgcac    4920
gcaccaaaaa taagcgtgac aattacgtgt tcccagaaca attcgaattt tgtcatgcaa    4980
aggtgtagaa atagcggttt ttaccatagt atctcctgat aatagatttt cccggcagct    5040
gtaatcgtat ccagataggc catccaaaaa cgttgagtgg tttacaaacg ttacatatat    5100
aagagagttg ttataagacc cccatacaac cggtccacca ttaatcaccg tggttgcata    5160
cacacactca tgttcaaact ttacacgagc ggtataccat agggtaaaaa cagcatgtcc    5220
gctaagtaga cacataatta taaaatgttc tgtcttgatt cctaaagcct gcatgacccg    5280
tggaagatgg caattcaagc acgatgtagt atcacacggt tggtgttaac tcgaagttaa    5340
atttggataa ttaggtactt ctagagtaaa gattgtatgc atgcgattgc tatcgcactt    5400
tgtagcaaaa cattgttgtg caagcgaaat acacaaacgg ttgtgatgat ccactcgcag    5460
agacacaaat gtccggggag ccgttcttcc tccgcgatgg ggatatcgaa gacaagtgaa    5520
cccttttgtt ccgcatatga gctgaaataa cacccagtcc cttttgatgg cgatacactt    5580
tgatgatgtt aaggtatatt cgcgatcacg cccggggaaa tgaacagcaa tatgctccac    5640
aatagattct aatattgtgc tgtcgacaaa ggcctccagt gtaaatgcgt ccagacaagt    5700 tacccccgcgc tcttttagag cctttgttaa agatatttgc ggggagctaa atatttgttt    5760
```

```
attacgcgca accttacgtt caaaaaactc tgcgtattcc cccccaaggt tatgtaaaat    5820
aaattgcact ggaacattcg actgcggtct tgaatgaaaa tgaaagtttg ccgggtttct    5880
atgtgatgtc acaaacgcta atatatcaat acactgctca ggtacaacat aaaatgggag    5940
tagttgtcca accgccgtcc ctgtggttgt tactttggag aaaaaaggca gtcttaaact    6000
atgtccgtgg ctataaacac cagtatctat aaacgaaaag tcccgtaaat acggaccaat    6060
atattcaaca aattcccgtt ccagcaacac cgcttgctgt aatatttgtg caaacccctt    6120
taaagtggaa gaccccacta acgcataggg atttgggatt ggtacgcata ccctgaaacc    6180
tattttctct ttacagttac agggtagagt ttcatgcaag ttttcattgt ttgatacatc    6240
ggcgtgtgta tggacttcag acgttgtctg tgtatcaaaa aaccatacat cctctgtata    6300
attctcttct acacacgtgt ataattcgcc attttctatg taaaaatcga tgtcagaatg    6360
gctggttata tccaataaat tatcatcatc caacacctca acggtaggtt caggacatgc    6420
agttttataa aaataacatg ggtctttgtt agggtttacc acggcctttg gaaaaagtaa    6480
ttgcatggcc gttaaaatac catgacgaaa tgctcgcatg ccggcatgta aaatacccaa    6540
tgggatgggt tttcttatat gaaagtctac atcaagtatg aggtttgtga ttataagatt    6600
tgtattaaat agctcattcc tgtttatata agctgatct ttgggtatgt ttgatgaaat    6660
tttagaaacg tttttaacag acgtagataa tagtaaagtc aactgcatat ctcgtagtga    6720
agcggcaaca aaattacatg gattaatttg tttaaggtcc tccgcaatta atcgagcctc    6780
gtgcggtaaa gtgtaacggt ttgttattga tgaccacgta tcattagcaa taacagcaaa    6840
tgcttgggcg ccgtgaggca aggctacccg atatacaggc attggtccag ttacctcaga    6900
atggccgatg agggcttcta atggagtttt ataactcagg atggatacat catgtgtggc    6960
tatcccagtg gcagcagaga aaaacagtaa tagttttgta atccccgggc tcgtatcaaa    7020
accagtacga ccactttggt taggtgtatc gtttgcaaag ttggctgctc gtaacgcctc    7080
cgcggaaaca cccgaatcct caaaattaga caattcgtca aaaccgggtg gatttgaggg    7140
aatagtggag gaccatccat atggactaaa ttgtttttca atgttttcca cacgacgagt    7200
tagcgttgta gctaggtcac atacgcctat aaacttgcta ggttttgcgg catacgtaag    7260
acttaaagta tatgttttag taattgtata tttatgtcca atctcaggtc caagttcagt    7320
gacatcacaa attacgttct tttttatata gtcacgcatg ttgagacgag aacgtacatg    7380
attaaaaaaa ttagcagtag ctcttttttcc caggttggat gattttaaga ggaccggttt    7440
attcacaaaa tctgagtatg taaccgcttg taggtggtct gcgatctgtt tccgattgaa    7500
acattcaaaa tgtgccagat aaatataatc aacaaattca cggtctggaa ctttaaggcc    7560
ttttctatcg ttggtaatat actccgatac tgcgtgtatt ccgttgtgt ctgtatgtat    7620 tcgctgtaaa atgtacgata gagcattttt ggctgtcaaa cctcgtgtat atgttgagga    7680
acaacaaaac atgaaagtt tatcaaaaga caacaagtcc gaaatattgt acccactaca    7740
attaggtaat gccgggactt ggtaagttaa aaacaaatct ttaattgcct gtaagtcata    7800
taagggggtt tccaacgtat tgtaacttgt gtccgtttgt aacaagtaat agcgtgtagc    7860
caacactagc gttttttcag agggtccaaa tcgaacaata taccaaaacg gcgagcatcc    7920
atacccccag tagagtcgtc gatatgcagc caatacttga cgttcgtaat gggcatataa    7980
tgatgttagc tcctgacgac caacggattt tttaactaac ttgcagagtg ttgcctctgt    8040
gatgcatagg ccgttgtccg ataatccctt tcggtttaaa tggtgtgttg ttaccatcag    8100
```

-continued

```
agtttgtata acttccgagt gaatgtcaaa cgtctccgat atacataggg tatcagatat    8160
tatatgcgga tttaggggtg ctccatacca taacgcctta tataaagctt taaaatcagt    8220
ttgggtttta aaacaacaaa aaaatatagg ccagacccgg gatcgtacat ctccagttga    8280
aaatccacca attaaataaa aaataacgtt gacgtcccta ctacaaaata aatgcattat    8340
ttggttttct tcatcgtttt cagttacttc acgtgggcgt ttagttggga ttacttgcgt    8400
gatctcttcc ctcccatttt tgacaaagac gtcatctaag tcgggagtcc aagtataact    8460
caccacatac agaggttctg tgcttatctg cccggtaagc aacaacagcg agtgggagat    8520
tgcacatccc tttgtggcaa ataataaccg aatcgtcggt ttggaggatt tatccatagt    8580
tcaatacgtt ggaaagccag tcaatcatgc agacggtgtg tgccagctta tgtggatatg    8640
ctcgaatacc aactgaagag ccatcttatg aagaggtgcg tgtaaacacg cacccccaag    8700
gagccgccct gctccgcctc caagaggctt taaccgctgt gaatggatta ttgcctgcac    8760
ctctaacgtt agaagacgta gtcgcttctg cagataatac ccgtcgtttg gtccgcgccc    8820
aggctttggc gcgaacttac gctgcatgtt ctcgtaacat tgaatgttta aaacagcacc    8880
attttactga agataacccc ggtcttaacg ccgtggtccg ttcacacatg gaaaactcaa    8940
aacggcttgc tgatatgtgt ttagctgcaa ttacccatttt gtatttatcg gttggcgcgg    9000
tggatgttac tacggatgat attgtcgatc aaaccctgag aatgaccgct gaaagtgaag    9060
tggtcatgtc tgatgttgtt cttttggaga aaactcttgg ggtcgttgct aaacctcagg    9120
catcgtttga tgtttcccac aaccatgaat tatctataqc taaagqqqaa aatqtqqqtt    9180
taaaaacatc acctattaaa tcggaggcga cacaattatc tgaaattaaa cccccactta    9240
tagaagtatc ggataataac acatctaacc taacaaaaaa aacgtatccg acagaaactc    9300
ttcagcccgt gttgaccccca aaacagacgc aagatgtaca acgcacaacc cccgcgatca    9360
agaaatccca tgttatgctt gtataaatat tgaataaaa actaaaaacg tttctggtgt    9420
atgttttat tttgtatata aaattaaaac attgctggct ggcgtggtta ttacatttaa    9480
tgttttagta gaaaatcgac atcgtttgtt tctttatcag ttgaaccaaa tccacgcgtt    9540
ccccgttcgc tgggtgtggc tattagatct aacgttttag taaaatacca ttgtacaccc    9600
ggtatgccac atttaccgcg gatagcataa ggaaatgcaa tattacttaa aacgttgtgt    9660
tttaagtgta tttgggtgtt gtgatctatt aacaggacct gtgcaagacg atctcccgtt    9720
tttatacgta tgtcatcacc cgtgagatta tatacgtaga atttacagtg ttctcctgca    9780
ggccatgccg ttggacacac gataatgcct gatcggcttt tcgatgatct tccaaaaata    9840
taagcgttta tactcggatg ttgtaagtcc cagtctctta taatcggtaa gacaattttt    9900
ataaattcat tccttttaa atataggtta tatggtacac aaatatcata tcccgcgtct    9960
tcttggcgtt ttgattgat gatatgtttg taggttaagg gaacatcgat atggtattct   10020
gcagaatccc tatgtaaagg ttgcccctgc tgtaccgtgg aaatatcagc aaattcaggt   10080
ataacggttc tttcataatt tgacggcgag tttgataagg gttgaacttg tatcgattta   10140
aaaattggat ccagatgttt aagaacgttt tttgggagaa ggcgactttg tcttaatttt   10200
accgggaaca agtagattgt taaatgtccg ggtaaaataa cggttactcc tggccggtaa   10260
tacaaaaggg ctgaaattac tcctctgtaa cccgcatcaa taactccgtt ggcgacaaaa   10320
aaattgtctt catcagcaag ggcagtatct ttgcattgaa ttaacaacag tgcgtattca   10380
tgggaggcg ccgacttaac caaacagctcc aactgctgca tataaaaacc gccccgtgtt   10440
acagattttt cagatggcag ttcgagtttc ttgtggttcc ggagtaacaa cggttgatgt   10500
```

```
cgacttactt tatcgtctaa cacgcattgc agcgtatctg cacattcagg ttgaacttct   10560
attaaaattg tatcttttaa acaccgattc ggaatagttt ggctacaaaa catatcacct   10620
gtatttactg ccgtttccaa gatgggatca attaccgctt cgttcatatt aataacgatg   10680
caaattttat ttttttgtga agacagcagt ggggagccaa actttgcaga acggaatttt   10740
tggcatgcca gctgttcggc tcgtggagtt tatatcgacg gatcaatgat caccaccctt   10800
ttcttctacg catccctttt gggggtgtgt gtagcccttα tttcgttagc ttatcatgcg   10860
tgtttccggt tatttactcg ttctgtatta cgcagcacgt ggtaaacccg tttgcctata   10920 aaagggggcag gcgtgtataa gagggcccct gtttaatacg cggtctgccg tgtttggata   10980
tttcacgacc ctatcgttta tttacgtaat ggcatcttcc gacggtgaca gactttgtcg   11040
ctctaatgca gtgcgtcgta aaacaacgcc tagttattcc ggacaatatc gaaccgcgcg   11100
gcgaagtgtg gtcgtaggac cccccgatga ttcagacgac tcgttgggtt acattaccac   11160
agttggggcc gattctcctt ctccagtgta cgcggatctt tattttgaac ataaaaatac   11220
gacccctcgc gtacatcaac caaacgactc cagcggatcg aagatgact ttgaagacat   11280 cgatgaagta gtggccgcct tcgggaggc ccgtttgaga catgaactgg ttgaagatgc   11340
tgtatatgaa aacccgctaa gtgtagaaaa accatctaga tcttttacta aaatgcggc   11400 ggttaaacct aaattagagg attcaccgaa gcgagctccc ccgggagcag gcgcaattgc   11460
cagcgggaga ccaatttcct tcagcactgc accaaaaacc gcaacaagct cgtggtgcgg   11520
tcctacgcca tcatataaca aacgcgtctt ttgtgaagcg gtccggcgcg tagccgccat   11580
gcaggcacaa aaggctgccg aagcggcttg gaatagtaat cccccaagga ataacgccga   11640
attagaccgt ttgttaaccg gagccgttat tcgtattacg gtgcatgagg gtttaaattt   11700
aatacaagcc gctaatgaag cagacctagg tgaaggagca tcggtatcca aacgtggaca   11760
taatcgaaaa actggagatt tacagggggg catgggtaat gaacctatgt acgcacaagt   11820
tcgtaagcca aaaagtcgaa cggatacaca aacgactggg cgtataacta atcgaagtag   11880
ggcccgttct gcatcaagaa ctgatacgcg aaaatagggα tataattacg cagtaacggt   11940
ttacccggta ttatgtataa taaataaacg tataaaagac agtcgtggtt tgtgtttatt   12000
ataaatgtgt attatatgtc acatattata aactgtttaa atagtaccac gtggtattat   12060 gaacagtttα taatcagttg ctaccaaaca aaccccatta gacggcgggt tttgataaag   12120
ggaatcgctt atttaaacta aagatttttac tctataagta tggagtgtaa tttaggaacc   12180
gaacatccta gtacagatac gtggaatcgt agtaaaacgg aacaagcggt tgtggacgca   12240
tttgatgaat cgttgtttgg tgatgtagca tcggatattg gatttgaaac gtcgttatat   12300
tcacatgcag ttaaaactgc tccgtctccg ccttgggtag ctagccctaa aattttatat   12360
caacagttaa tacgggatct tgattttttca gaagggccgc gtttactatc atgtcttgaa   12420
acctggaacg aggatttatt ctcatgtttt cctattaatg aggacctata ttccgatatg   12480
atggttttat ccccggatcc agatgacgtt atctcaaccg tttcaaccaa agaccatgtt   12540
gaaatgttta atttaacaac ccggggttcc gttcgattgc ctagtccacc aaagcaaccg   12600
acggggcttc cagcttacgt tcaggagtc caggattcgt ttaccgtaga actacgcgcc   12660
cgggaagaag catacacaaa actactagtt acttattgta aatcgattat acgttatctc   12720
caaggaacgc cgaaaaggac gacaataggt cttaatatac aaaaccctga ccagaaagct   12780
tacacgcaac tcaggcaaag tattctactt agatattatc gtgaggtggc aagtttggcg   12840
```

```
cgtcttctgt acctacattt atatttaacc gtaacgcgtg aatttcctg gcgtttgtac      12900 gccagtcaat ctgcacaccc ggacgtgttt gcggctttaa aattcacctg gaccgaacgt      12960
cgacagttca cgtgtgcgtt tcatcctgta ttatgcaacc acggcattgt gttattagaa      13020
gggaaaccac taacagcgtc tgccttgagg gaaataaatt accgccgccg agaactggga      13080
ctgcctctag ttagatgtgg tcttgttgaa gaaaacaaat ctccgttggt tcaacaaccc      13140
tcattttcgg ttcatttacc acggtcggtg ggttttctta cccaccacat taagcgtaag      13200
ttagacgcat atgcggtcaa acatcctcaa gaaccgagac atgtacgagc ggatcatcct      13260
tacgcaaaag ttgttgaaaa tagaaactac ggtagtagca tcgaagctat gatttagca       13320 cctccgtccc catccgagat cctgccgggg acccaccac gcccaccac gtgtgggttt        13380 ttaacgcgtt aaacgtcatt ggggtagagg gtgtaaataa attacgaaaa cgtgcatgcg      13440
ttttttattt ttacaatgcg ccgtatatgg tatgtctgtc atgtgctcta aagtcccata      13500 tataaagaa gccccaacga gtgtatgcgt attgcgtacc gcgaccctgg gatgttttac       13560
aggcgcgttt gtttgtctcg gttataagta tgcagtcggg tcattataac cggaggcaat      13620
cccgccgaca gcggatatcg tctaatacca cagactcccc ccgtcacaca cacggaacac      13680
gttatcggtc aaccaattgg tatacacacc caccccagat attgtccaat tcagaaacat      13740
tagttgcggt tcaagaacta ctgaactccg agatggatca ggacagcagt tctgacgcat      13800
cggatgattt tccgggatac gccttacatc attctacata taatggatcc gaacaaaata      13860
catcaacttc cagacatgaa aatcgcatat ttaaattaac ggagagggaa gctaatgagg      13920
aaatcaacat caatacggac gcgatcgacg acgagggaga ggcggaggag ggagaggcgg      13980
aggaggacgc gatcgacgac gagggagagg cggaggaggg agaggcggag gaggacgcga      14040
ttgacgacga gggagaggcg gaggaggag aggcggagga ggacgcgatt gacgacgagg       14100
gagaggcgga ggagggagag gcggaggagg gagaggcgga ggagggagag gcggaggagg      14160
acgcgatcga cgacgaggga gaggcggagg aggacgcggc ggaggaggac gcgatcgacg      14220
acgagggaga ggcggaggag gattattttt ctgtaagtca agtttgcagt cgagacgcgg      14280
atgaggttta ttttacgtta gacccggaaa taagttacag taccgatctt cgcattgcaa      14340
aggttatgga gcctgcggta tcaaaggaac ttaatgtatc aaaacgttgt gttgaacctg      14400
ttaccctaac aggctctatg ttagcgcata atgggtttga tgagtcctgg tttgctatgc      14460
gcgaatgtac ccgtcgcgaa tatattacgg tccaaggatt atacgaccca attcatttac      14520
ggtatcagtt tgatacttcc cggatgacac ccccacagat tttgagaact ataccagccc      14580
ttcctaacat gacacttggt gaacttttat tgattttcc tattgaattt atggcccagc       14640
caatttctat agaacgtatt ttagttgaag atgtattttt agataggcgg gcttccagta      14700
aaacacataa atacggcccg cgttggaatt ccgtctacgc acttccatat aatgcgggta      14760
aaatgtatgt acaacacatt cctgggtttt atgacgtgtc cttacgtgct gtgggccaag      14820
gaacggccat ttggcatcac atgatattat ccacagcagc atgcgctatt tctaatcgca      14880
tttcacatgg agatggatta ggattttgt tagacgcggc aattcgtatt agcgcaaact       14940 gtatttttt gggacgtaac gataattttg gcgtgggga tccatgttgg ttagaagacc        15000
atcttgccgg attaccacga gaagccgtac ccgacgtact ccaagtgaca cagttggttt      15060
tgccaaatcg gggtccaacg gttgccatta tgcgtggttt ttttggggcg ttggcatatt     15120
ggcccgaact aagaattgct ataagtgaac catctacatc tttggtgcga tatgctaccg      15180
gtcacatgga acttgccgaa tggttttat tttcacgtac acatagttta aagccacaat       15240
```

-continued

```
ttaccccaac ggaacgggaa atgttagcgt cattttttac gttgtatgtt actcttggtg    15300
gaggaatgtt gaactggatc tgtagagcaa ctgcaatgta tttagctgct ccttaccatt    15360
cccgttcggc ttacatcgcg gtctgtgaat ctctgcccta ttactatatc ccggttaata    15420
gtgacctgtt atgtgattta gaggtattac tgttaggcga ggtcgacctc ccaactgttt    15480
gtgaatccta cgcaactatt gcacacgaat taaccggata tgaggctgtt cgcacagcag    15540
ccacaaattt tatgatagag tttgccgatt gttataagga aagtgagacc gatttaatgg    15600
taagcgcgta cctgggggcc gttttattgt tacaacgggt gttgggtcat gcaaatcttc    15660 tttttgttgct tctctccggt gctgcgttgt acggaggatg ttcaatttac atccccgag    15720 gtatttttaga tgcatataat actttaatgt tggcagcaag tcctcttta gctcaccaaa    15780 cttta acatc cttttggaaa gaccgcgatg atgcaatgca aactttgggg attcgaccga    15840
caacggacgt tttacccaaa gagcaagaca ggatagttca ggcatcacct atagagatga    15900
acttccgttt tgtgggattg gagaccatct atccccgaga acagcccatt ccctccgtgg    15960
acctagccga aaatcttatg caatacagga atgaaattct gggtttggat tggaaaagcg    16020
tagccatgca tttactacga aaatattaag ggttgtgatt tttttcatta ggatgaaaag    16080
aacgtttcct agccacaccc acaaaggagt ttgtaaaata aaatctctgt ttagaccta    16140 aaatttgttg tgtgtgttgt gtgggggtc cgtgaggatc gacctttaca agatataatt    16200
tgtccatatc gcaatgtttt ctcggtttgc gcgttccttt tccagcgatg atagaacgcg    16260
taaatcttat gatggtagtt accaaagttt taatgccggc gaacgtgatt tgcccacacc    16320
tacccgggac tggtgttcta tttcccaacg cataaccagc gagcgcgtga gggatggatg    16380
tcttattcca acgcccggcg aggctttgga gacggcggta aaggctttat ctgaaaagac    16440
cgacagccta acatcgccgg ttttacaaag taccgaaaga cacagtgttc tgcttggatt    16500
acaccataat aatgttcctg aatcgttggt ggtctcgtgt atgtctaacg atgttcatga    16560
cgggtttatg cagcgttata tggaaacaat tcaaagatgt ttggatgacc tgaaactttc    16620
tggggatgga ctttggtggg tttatgaaaa tacatattgg cagtatctca aatacaccac    16680
aggagccgag gtaccggtga cttcagagaa ggtaaataaa aagtctaaat ccacggtttt    16740
gttgttttca tccgtagttg ccaataaacc aatatccaga catccttta aatctaaagt    16800 tataaattcg gattaccggg gaatatgtca ggagctacgt gaggcgttag gagctgtgca    16860
aaagtatatg tattttatgc gtccagatga tcctacaaac cccagcccgg atacaagaat    16920
acgtgtacaa gaaattgcgg cttacacggc tactggctac gggtggatgt tatggttctt    16980
ggacgttgtg gacgccaggg tatgtcgcca tctcaaactt caatttcgac ggattcgagg    17040
gccgcgcgcg tctgttattc cagatgattt gcttagacga catttaaaaa cgggtcctgc    17100
ggtctcagcg gcacaggag ttgcgtttat tttagcagca acaactgcca gcgctcttac    17160
tgcgcttttg cgtattagtg tattatggcg aaaggaagag tggcgggatg gtttaaatgg    17220
aaccgcagct gcaattgttg cggcggttga acttattacg cttttgcacc accatttca    17280 atacttaatt aatatgatgc ttattggata tgcatgttgg ggggatgggg gattaaacga    17340
tccttatata ttaaaggcgc tacgtgccca gggacggttt ttatattttg cgggtcagtt    17400
ggtcagaaca atgtcaacac acagttgggt tgtgttagag accagcaccc atatgtggtt    17460 ttcccggggcc gtggcgcaga gtattttagc acatgggggt aaaccacaa agtattatgc    17520 tcaggttctt gccgccagta aacggtatac tccgttacat ttaagacgta tatccgaacc    17580
```

```
atcgagtgtg tctgatcagc cgtatattcg ttttaatcga ctgggatctc caatagggac   17640
aggtataggg aatttggaat gtgtctgttt aacgggaaat tatttatctg acgacgtaaa   17700
tgcaagttcg catgtaatta atacagaagc accgttaaac agtatagcac ccgatacaaa   17760
tagacagcgg acttctcgcg ttttagttcg tccagacacg ggtttggatg taactgtccg   17820
aaaaaaccac tgtctggaca taggccatac ggacggtagt ccagttgacc caacgtatcc   17880
tgatcattac acccggataa aggcggaata tgaaggtccg gttcgggatg aatcaaacac   17940
aatgtttgac caaagatcgg atttacgtca catagaaacc caagcatctt taaatgatca   18000
cgtatatgaa aatataccac ccaaggaagt gggttttaac tcatcttcag acctggatgt   18060
ggatagcctt aacgggtaca cctccggaga catgcataca gacgatgact tatcaccaga   18120
ttttataccc aacgacgttc ccgttagatg taaaaccacg gttacgttta ggaaaaatac   18180
gcctaagagt catcattaag tacagcggtt aatagatagt tatggactag cactttggc    18240 ggtcatttcc acaaccaggt taaaattggg ggatttggga gaaaatagtc tattgcgtat   18300
tttctgttca ataattggac tgcgttattt aaaggtctga ttggttgatt gggttataaa   18360
aggaattact cctttaaatt ttacttaatg tacccacaat atcaagtggt cgtttgtatt   18420
taacgattat taccggtacc atgggagact tgtcatgttg acaaaggtg ccgggtttta    18480 cgttaaccgg cgaacttcag tacttaaaac aagtggatga tattttaagg tatggagttc   18540
ggaaacgcga tcgaacagga atcggaacgt tatctttatt tggaatgcaa gctcgataca   18600
atttgcgaaa tgaatttcct cttttaacta caaagcgtgt tttttggagg gccgtcgtgg   18660
aagagttgtt atggtttatc cgcgggtcaa ccgattccaa agaactcgcc gctaaagata   18720
tacacatatg ggatatatac ggatcgagca aatttctaaa taggaatggc ttccataaaa   18780
gacacacggg ggaccttggc cccatttacg gcttccagtg gagacatttt ggagcggaat   18840 ataagactg tcaatcaaac tatttacagc aaggaatcga tcagctgcaa actgttatag    18900
atacaattaa aacaaaccca gaaagccgac gaatgattat atcgtcttgg aatccaaagg   18960 atatccccctt aatggtacta cctccatgtc acacgttatg tcagttttac gttgcaaacg   19020
gtgaattatc ctgccaagta taccagagat cgggggatat gggccttggg gtaccgttca   19080
acattgctgg atatgcactt cttacctaca tagtagcgca tgttacagga cttaaaaccg   19140
gagatttaat tcatacaatg ggggatgcac atatttactt gaatcatata gatgctttaa   19200
aagtgcagct agctcgatcc ccaaaacctt tccttgcct taaaattatt cgaaatgtaa    19260
cagatataaa cgactttaaa tgggacgatt ttcagcttga tggatataat ccacaccccc   19320
ccctaaaaat ggaaatggct ctttaatgga tttttaaatg ttgtcaagac agtagatgtg   19380
ttgcgaatgt aataaaatga tatacacaga cgcgtttggt tggtttctgt ttatgaacag   19440
caacggatgc ataggggttgc gataactgcg ataagaccca atgtcccaag gatagatatc   19500
acaccaatta taactgctac aacggaaaat gtagtggcgt aggtagatgc atcgtaggta   19560
taaacggccg aaaacggagg gaatttttta gggtaaccat ctagatgaca cgaataggtg   19620
ataggtccgt cgagttccga tgttggacaa gaactttgca tgtttacaaa ccgtttgttt   19680
tgatcacaca ccccagtaat ctcactgttt tcgtggttaa tgggagaatc gttaacccac   19740
catacgaaat gtacaacgcc acgtggcaca cattttgccg tacatactat gtgtccatca   19800
ataataccta tagacacgtt gggaaatgga tagacgtcag gggtaacgac agcagaaatt   19860
ttcatattag agacgccatc ccgaatccat aaaacattac attggatggc tgggggtggg   19920
taatccattt gttttgctg tggaattcgt accgccgaaa cataactaaa taatccattg    19980
```

```
gcatattctt gtattgcatc ggttataaaa ttttttccga tgttaccaaa ccttgaagtc    20040
caccgaacac gtaccgagtg cggtggataa tactttgata cgttacagta ggctgcgtat    20100
gtctgtccgg ttaagactgg atcgccgaca acggtaatat ttggacgata atacgttgta    20160
actgtaatac tgtgttccga tatgacgttc ttagttttg tattaacgac tcgccaaata     20220
tacgttccct ccgtggtagc atccatagat aaaattgtta cagaaaaatc agacgttgtt    20280
ttaacatctg gtattacata attttcctta gcgtgtgtaa atatctcagg gttgtttatt    20340
aagtttaaat cggcactgtt gctatataac ataaccggta aatctggcat gcgtattaac    20400
gcattgccca gttgacggtg cggatctata aggtgacgcg taaaccaaac ttcaatatga    20460
agatcggggc gtataagcga cttccacctt gttatatttg aaccttccgg atctaaagaa    20520
tattgttcat atgttttttg ttgctgctta aaggccgcct gttgtccggt cgttagacgc    20580
atgtaacaag gcatgataaa tgtgtgaaaa tagggtatgg attgtattcc gccgtgaacg    20640
cattgtatat tttcatatag aaaaggtggt tgtgaatgtt gggtgttggc tgcgggatcg    20700
ggctttcggg aagcggccga ggtgggcgcg acggcgggat cgggctttcg ggtagcggcc    20760
gaggtgggcg cgacggcggg atcgggcttt cgggaagcgg ccgaggtggg cgcgacggcg    20820
ggatcgggct tcgggtagc ggccgaggtg ggcgcgacgg cgggatcggg ctttcgggaa     20880
gcggccgagg tgggcgcgac ggcgggatcg ggctttcggg aagcggccga ggtgggcgcg    20940
acggcgggat cgggctttcg ggaagcggcc gaggtgggcg cgacggcggg atcgggcttt    21000
cgggtagcgg ccgaggtata taattcagtt atacttacgg gtgtgggttg agattcagtc    21060
gataattgta tacacgcgat cgttaaaatt aaatttattt gtatccgctt catcctggtt    21120
tttattgaca catccacgct ccccttaaat aaaagattaa acacccacc gcggaattta     21180 aatgatggaa acgtttttt cgacattggg aataataaaa acggcttttg caactttaaa     21240
aactttattt atctcgatta cgatacatat gtaccacata gatagcatag atttattata    21300
atataaacac acacgtgata tactttagtg atatgagatg ccataaaaca gtcaataggt    21360
ttaacgctta gtctcatcat ctgaatacac gtcaaacccg ccgcaactgt tgatgttaga    21420
attataatag ctccccatga aatgccggca aatgttacag ctataccegt caccgaggtc    21480 gttgtatata atacaattac ccataggttt ttttttcttt gatataaaac ggcaaaaccc    21540
tgtaacccaa atgctataat atgacctcct attgaaactg ctaacgttac ttgtgtaagt    21600
ttgataaaat gatttaattt aattatatgt gagattgccc acattaatgg ggtaactata    21660
tataacaccg ggggtataac agacattata cgaattcctt taaacacgcg tttaagggtc    21720
cgggaacttt ctcgatggtc acatactctc ccgcggtcat tttgtgtata tacaacggca    21780
aaacctaaat ctgtataagt gtttaattgc ttatggcgat ttttacgata tatacacgta    21840
tcttgcaaat cggtggcggc atcgacaatt gaaactagtg tgacaataga tatacacaat    21900
ccaataagaa cctcatattt actgacatac atatataaaa taacggttag taaacctccc    21960
aacccagttc ccaacatcat aacataaaaa taaatatgcg gtccattgaa tgtcgtaaca    22020
aagttgtagt aatggatatg cacagcagcc actgttccgg taatcgcgga tatggaaatt    22080
cccagtaatt ctacaaatgg aagatcccgg gatattgggc aaccaaccgc cataacaca    22140 gcaaaaccca acacgaccac cgtctgcaaa catcgtccca attttgctaa tgtgcgtaga    22200
aatttcacgg atgttggcca taaccccgaa acgacgatca accccataat agttgcattg    22260
acggcagctt cgcagacgtg atattgtaaa attaacccgg acgtgataac gcttgcttgt    22320
```

```
agtcccacga gaaacaaccg cgatgctgag gttattgcac acgaattaca ttcttgaggg    22380
tttccgacac atccttggat tgattgagcg cggattaatt ctctgtctaa cacacccagg    22440
ttttcatcat ggacagctct ttcaccattc acggccatgt cttaagttta ataattcaaa    22500
acaaataaaa atgtgttcat ctatggtaca cacaagtttg tatgtaaaat ataagcaaaa    22560
gttgcactta tttaactgta catattacgt cagattcacg tgataattca gaataatcca    22620
gggttcctgc agggtccact ggaggagcca cacaatattc gcgaattccg attccctcct    22680
gccatgtggt ttcggggagt ttcccccca tttttattcc ggtatttttt tcgtttcttt    22740
ttgttaataa attgcgtctt tttttttaatg gtggttcatc cttcacagat tccatgttcg    22800
caaataattg catcgaggtt aattttcctt taaggtcttt gggacttaag aacgttgcat    22860
aaaaaaaaga atgcacgggt gcggaacgtt ggatatacaa tccaaccatg ggggagttag    22920
ttaaggcgag ataaaaatta atataacacg tctcatcccg tgttaactta agattttgta    22980
cggcagaacg gaatccactg tgtgtttcca ataatactcc aaattcacgc atactcccgc    23040
tgccataaac aacattatta aggatccttt ttgaatttgt gattgagcgt attaaattat    23100
atggtgtagg cttgcttccg tttatatcca aggaaacatt aaatgagata aaaccacccc    23160
cggcggtctg gatgtacata tccgtggctg ttagaatgaa gcatgttgta aacccaaaag    23220
ttttaagtag tcgctgtaaa cgggtgaatt gatcgcgttt taagcaaatg cttatatctg    23280
gagttagatt tggaaacatc attgtataac aagcgagttc acgttttaca acttgttttgt    23340 aacattgtac ttgatcatct ggaccacaat cacccgggcg ttgccatacc atcgtttgga    23400
taatactccg ctcgggggt tgtccggtaa atttaaaata taaccgtgtt ggggtcgacg    23460
gatcttttgt atggcgaaac gcgtcaataa gcgaggaccg tccctccgtt gccgcgagta    23520
caaccattct cggcccagtc caattatact ggtcaaacat atttgccggt ataggaatat    23580
acagttgttc tgtttccaaa ctacagtgaa taattaatcc ttcgtcgctg aatattaaaa    23640
tagaatccct tagtctatta accagaggtg atatagacga aattaaacca gtaagcgttt    23700
tttccgttaa aacagctctg gcgatttctg gggcgtcaaa acccgcatgc aattccatgt    23760
ccaaagcatc gtctgtacgc gacctcaaat ccataattta ctacttaaaa tgtttactat    23820
agaaaaagta atcatatgta aacacacgag tttcgttaat atgtttgttt aacccgatcc    23880
ggtgacttaa gtacataaac aggcatgata tttgaatagt acggcccatg ggagggaaca    23940
tttccacgtg ttccaataca gggggtgttc cttaataggg actgtgcaat aaaatacgta    24000
agaagttacc agatttgatg taatgtttgt cataaaaaat atgtacatca ttatatacgt    24060
ctgtaattaa cacaagatca catcgaagaa ttactgaagc cgctgtgaaa cctttcacaa    24120
gacgatataa acttggttaa gtgtattgat ggggctcttt ggactgacac gctttatcca    24180
tgaacataaa ctggttaaac ccagcatcat ttcaacgcca cccggagttt taaccccgt    24240 ggcggtagac gtatggaacg tcatgtacac attgttggaa cgtttatacc ctgtgggtaa    24300
acgcgagaat ttcacggac catctgtaac gatacattgt cttggagtct tattgcggct    24360
attaacacaa cggtcatact atccgatatt tgtattggaa cgttgtacag acggcccatt    24420
atcacgtgga gccaaggcaa ttatgtcacg ggccatgaac cacgatgaaa ggggaacctc    24480
ggacttaacc cgtgttctac tatcatccaa cacatcatgt tctatcaagt ataacaaaac    24540
atcggaaaca tatgacagtg tgtttcgaaa ctcttccacg agttgtattc ctagcgaaga    24600
aaacaaatcc caggatatgt ttttggacgg ttgtccacga caaactgaca agacgatctg    24660
cctgcgcgac caaaacgtat gcagtcttac ctctacaatg ccatcccgag gacatcctaa    24720
```

```
ccatcgatta tatcacaaat tgtgtgcaag tcttattaga tggatggggt atgcatacgt    24780
cgaggcggtt gacattgagg cggacgaggc atgtgcaaac ttatttcata cgcgtacagt    24840
ggctttggtt tatacgacag atactgattt actcttcatg ggctgtgata ttttgttaga    24900
tgcaattcct atgtttgctc cagtagtacg atgtcgcgat ttgcttcaat atttaggaat    24960 tacatacccct gaattttggt tgcctttgt tcgctgtcag accgatttgc atacaagtga    25020
caacctaaaa tctgttcagc aagttattca ggataccggc ctgaaagttc cacatcaaat    25080
ggacacttca acgcgctccc ccacttacga ctcgtggaga catggcgagg ttttcaaaag    25140
tcttaccgta gccacgtcgg gtaaaacaga aaacggagtg tccgtttcca aatatgcatc    25200
taaccgatcg gaggtgacag tagacgccag ttgggcttta aaccttctgc caccctcatc    25260
ctccccattg gataaatttg aacgcgcatt tgttgaacat ataatcgccg tggtaactcc    25320
attgacccgc ggtcgcctaa agttaatgaa acgtgtaaat attatgcaaa atacggcaga    25380
cccatatatg gttattaaca ccttatatca taacttaaag ggggaaaaaa tggctcgcca    25440
atacgcacgt attttttaaac agtttattcc tactccactc ccactaaaca ctgtattaac    25500
aaaatattgg aattaaaaca cacataagag cgacttaatg gttcattgtt ttattttgct    25560
cgtatataca tgttataaat cgtttatcac tgtgcccgca taagatgtac tgtgtctctc    25620
aaaaaaattt gtgttttttat ctgcaatcat aaatgcaagt ggaaagtccg aatcgggagg    25680
tggggtgtta aatagttttg gtacattaat cgctgataaa agcctgtccg cgctgaattt    25740
cacgtattgt gtaattgcat cgacgttcac caaacgggtt ttgggtgcat gggattttaa    25800
aaacgcacac tcgatttcaa cggcttccga aaacagttga tgtattctgg tgatagcggg    25860
tttttcgggt acatagttat tgtatataca acacgatgcg ctggtatgta tggcttcatc    25920
tcggcttata aggtcgttaa attgacaagt tacaacaaat agtccgttat tgcgtaaata    25980
tgcaatagcc gcgaacgatg atacaaaaaa aatgccctct ataagaatca ttagtatata    26040
tttttctgca acgatgggt tgtcccgtac cttttcttcc aaccattgta cttttttgttg    26100 gatcgacgga ttattaatag tgcacatttac gtattgtacc cgcaacgatt catcccctct    26160
gaacaacatt agttgaattt gactatagac acgcgcgtgg acaacctcga tgcactcttg    26220
ttcaatgtag taatggtgaa tatccttttg ggaaaagagt tgggttagag agcccaaatt    26280
aacatttacc agatcatctg ccgccgataa aaatgtaaaa ataaatcgt agaatattag    26340 ttcatcttcc gttaaacagt ccaagtattg ataatcatct tcaatgataa aatcgctttc    26400
taaccaacga ttcgaaatgc tcagggcacg taaattgttt atatctggac actccggcct    26460
gtaaaaaaaa tgactgcaat cttttctgatc cattttggaa tagtttcccg tgtaaattta    26520
taaagcacaa ctggtacagg ttaattcgcc tcccgcaaac agtccgctgt tcgtagcttt    26580 acgaattta cagtagtaca tacccgtttt aaggccggct ttataggcac gtataagcaa    26640
attcattatt ttggaggcgg gaattgtccc gtctgggcgt tcctcaataa ataaagtcat    26700
tgattgactt tggtcaataa atggcgccct ttctgcacac atatcaacga gatcctcttg    26760
ctcatattca aacgctgttt tattttttaa gagtgggtga ctattagata aacagccaaa    26820
cgaacgtatt actgaccatt ggttttctc aagtatgttt ataacttcca gtcgttttttc    26880 ttcacatgaa tacatatctc ttagttcgtc cataaggtct aagttgggtc taagtaactc    26940
accgagggtg gtgaccttac taaacatatt attataaatt ggagagaaac cctcactgca    27000
ctccgttacc tgtgcagatg aaactgtggg cattaacgct aagaactgcg agttgtataa    27060
```

```
cccataagcg caaatatcat ctcgcagggt acaccatggt aaatctaaat aacttatcgt   27120
agaaaaccca tcttggtgta accatccctt agcatattta ctttcggtaa aacccttaaa   27180
cggggctaag ccgccaatct tacacatttc catgcttgtt ttcattgtct catacaacat   27240
taactccgct atttgtacat ttaaccgtct agctggttgg gaagttaaat caaatcctaa   27300
gcggagacaa gttgtatgta acccttgtat gccaatgcca agtgatcggt tgttttttac   27360
acctttacat gatttttttac atggaaagtt cccagccgcc aggacccccgt ttaaaaaaat   27420
aacagtcgtt cttgctgtca attgaaggtc gtttaaatta aatgacactg gcctttgga   27480
taagcacgtt gtaagattta tgctggcaag attacatacg ccatgttgat gagcgtctgc   27540
cttttgaaca atttccgtac acaaatttga ccccgtgata gcatttcctt gggtattcat   27600
atgataatta cgattacagg catctttgaa cattaaaaag gggcttcctg ttacagcagc   27660
actgcgtatg attgtgaatg cgatatcttg aatgggaaca gaagaaacgc ctaatccttc   27720
tctctctaaa cgtaaatagg ttgaagtgaa tgcctccccg tgtaatgttc gaaggatatc   27780
ggctctgtta tcaaaagag tccactgaac attactagcc ccttttagat agcttaggta   27840
tctttcaaaa aataaatctg gggtccataa acaacaaaat atgttatcac atcgaaatat   27900
ttcatcacga accaacattc cacgtgtggc caaaacagtt tgtagatcga cgtgccatgg   27960
ttctatgtaa acacaaactc cagttggtcg ttcacaatca ctgttaattg ccataaccat   28020
gcaatctaaa agttttaaaa ctgcaagaag cctttcgtt tgattttccg taggtattaa   28080
attcagactc tgtagagaaa ttcccactcc acctcgactt tgtaataccg ttcccacatc   28140
gcctgtgata gctcgaacag ctctcccaac agtgatggat tccgggtcca ttaaataaca   28200
actggccgtt gccccggtct ctcgacctaa aaacatcata accggtgtag ccgggacaat   28260
tttctgacat gccaacgctg tgaaaaatac ccgacagaca tcagtccatg tataaccatc   28320
atttattccg ggaataagag ttgcgatttt aggcaggttt acgatttctg ttgtcacggt   28380
ggccgccagt cttaaaaaga attggcaaag cgactctaat ttaccttcct ctaacttagt   28440
taaataaaag tcttcgtact ttaaagcaga ctgtagtcca agggtagcta aagcggggta   28500
ttgatctttc aaaaacggtt ctaatatagc ccgacgaatt tcgtccctcc gcccttcaat   28560
tgcttggcgg actcggggag ttaaacagag aattggggaa gtcaaccacg tttccatgga   28620
aacggatcgt aggttaatac ggcaatggat aagttctcca caacatcggt acactcgctc   28680
atcttgtcgc gtcaccgcct taagttttga gacgatagtg ctaatatact ccattaattc   28740
caccggtgtg gttgattcgg gcggaatgat gtattccttg tagccatgtt gacataatcg   28800
gtttataatg tcatgaaccg tattaaaaat tcttttgaac tccataacgg ataacgtatt   28860
taggctccgg aataaacctt taaccctaa actcacagct gagttagttc tacaatattg   28920
tagactccct tatatatggt tacgtacagc ctgccccctcc ccagtatata atatcacgca   28980
aaacccacgc tatgttaaat tcagtttatt ttacatacat gctttaataa taacattcgt   29040
tccatgtatt tgtacccccc cacacaaccc cctctaacca aatagttggc acgttataac   29100
ctccgaaccg ttccatgcgt cttgtataac gcacagactc tgatggaatt gttccaatta   29160
acgtatatgc cgcatacatg caggataatt gtgtgggaag tccccgaaaa tcgccggtcc   29220
attgatacaa tcgctgtcta gccaagttcc aatttactcc tgtaatttcg ccaatactac   29280
atcgagggct tgtcgggtca ttggataact gcacaagcgg caacgccctt gtgttatatg   29340
gctggtgggt atttgcaacc ccttcagtcc cccaggcggc attttcagct cgtatgcgtc   29400
ctaacaggaa gccaatacca cgaccaaaac attgttcgtt tagttggctt aatgcaagat   29460
```

```
gcagtcttac accttctcgt tggcgtcgct gtgtatatac aaaaaccaag aacacatgct    29520
tcagtccgtc cgcggaaaga tgtaaatctt tgtcaacgtc ccaaaatacg caggccggga    29580
tgttggctgt gaccctgcga gttgaagttt tgtctgtacg tgcagcttct tggggacctt    29640
tggccacggc ggttatattg cataaattat cctgaatggt atattccagc agggacccaa    29700
aaaaacttat aaatcgatgt ggaaatacat gacattgtac catcgcacgt aaacactccg    29760
aaaaccttat gagccgcgtt tccatacgac tgcatccata gcagaaaaca attgctgttc    29820
tgttggcatc cgctgcctgt ttatccgtat attcttctgc ccggcatgcg gcgatgaaac    29880
ttaatgacgt tacatatgct ctaagccccc caccttctcc aacggtccaa ggagccgtgc    29940
aggcattgaa taggtttcgt aaaccctcta gtagtacatc ggggtcacgt ccagcctgtg    30000
taagtgtatt agcttctcca atcatgtcag atggatgacg aaggattaag acgattgacc    30060
cagcatgctc aatgtccgga cgaaaaaaat cggttaatga cacttgttgg attagctgtg    30120
tcgttgattt aaaattattt aacgggagtc taatggtaac ttgcgggtta ccaattgaag    30180
ttggatttat ttgaatgttg ttcatacgat taataacaat tgaacggggg gttacttgaa    30240
tagacgcggt ttctgtacgt tttggtggta catgtatcgg ttgtttgttc agacctccaa    30300
agcgagggcc aattgttaaa tcgcgactcc aatttccgaa gaagcccgga gcataagtca    30360
tatgaagccc gttccctatt tgaataaaac ggttatttcc taaaagactg atattagttc    30420
cacatagcgt ttgttcgttt aaagtaaaat gcgagttggt tggttgactc cccatagctg    30480
aggggttaaa ttcacacaat gcaatcgtga cgtggtacta tctgaaatgt tgcctggggt    30540
atgtgtacac attatacagt cgtagtaccg tttatataat gttaggtagg aggagcctat    30600
aaaaatattt tgattggcgt taaaaggttc ttcaacttac cgtgacgtcc tttttattaa    30660
catgcgtttt tattgatgtt acatttatgt cttttcattc cggacggatg tagcttttc    30720 atatcacgtt ataaagttaa gtcagcgtag aatataccat ggaagaacca atttgttatg    30780
atacacaaaa acttttggat gatttaagta acttgaaagt acaagaagcg gacaacgaaa    30840
gaccatggtc accagagaaa acagaaatcg ccagagttaa ggtagttaag ttttttacgat    30900 ctacccagaa aattccagct aaacatttta ttcagatatg gaaccccctg cattctaata    30960
tctgttttgt atattccaat acattttggg cggaggctgc tttcacggcc gaaaatttac    31020
ccggactgtt gttttggaga ctagatctag actggacgat agaggagcca ggtaatagct    31080
taaaaatttt aacccagcta tcaagtgtag tacaagattc cgagacgtta catcgtttat    31140
cggccaataa attacgaacc tcgtctaaat ttggacccgt ttcgatacac ttcattataa    31200
cggactggat aaatatgtac gaggtcgcct taaaggatgc aacaacagcc attgaatcac    31260
cattcactca cgctcgtatt ggaatgttgg aaagcgccat tgcagcttta acacaacata    31320
aatttgcgat catttacgat atgccatttg ttcaagaggg gattcgtgtt ttaacacaat    31380
atgcaggatg gcttcttccg tttaatgtta tgtggaatca gattcaaaat agctcactca    31440
ctcctctaac acgagccctt tttataatct gtatgattga tgaatatctc acggaaacgc    31500
cagtacatag catatcagaa ttatttgcag atactgtaaa tttaattaaa gatgaggcgt    31560
tcgtatccat cgaagaagcg gtaacgaatc cacgaacggt gcacgagtca cgaatttcct    31620
cagctctggc ttatcgagac ccttatgttt ttgagacatc cccgggaatg cttgctagga    31680
gacttagatt agacaatggt atatgggaaa gcaacctctt atcgttgtcc accccggaa    31740 ttcatattga ggcgctgtta catttactaa actccgaccc ggaagcggaa accacatctg    31800
```

-continued

```
gaagtaatgt agcagaacac acccgtggca tttgggaaaa ggttcaggct agtcatcgc    31860 ctagtatgtt aataagcacc cttgccgaat ccgggtttac aagattttca tgcaaattgc   31920
tacgtcggtt tattgctcac cacacactcg ccggttttat tcacggaagc gttgtagcag   31980
acgagcatat tacagatttc aacaaacac taggatgtct cgctttagtg ggtggactgg    32040
cataccaatt agtggaaacg tacgctccta ctaccgagta tgtgttaaca tatacacgga   32100
cagtaaacga gaccgaaaaa cggtatgaaa cgctattacc cgccttagga ttaccaccgg   32160
gaggcctggg acaaattatg cggcgctgtt ttgctccacg accccttatt gaaagtatac   32220
aagcgacacg cgtaatacta cttaatgaaa tttcacatgc agaagctaga gagacaacat   32280
attttaagca aacacataat caatcctcag gtgcgttatt accacaagca ggacaaagtg   32340
ccgtacgcga agccgtacta acctggtttg acctacgtat ggattcaaga tggggtatta   32400
ctcccccggt ggatgtgggt atgacacctc ctatttgtgt tgatccaccg gctacagggt   32460
tggaagctgt catgataaca gaagcactaa agattgcata tcctaccgaa tataatcgct   32520
ctagcgtgtt tgtggaaccg tcgtttgtgc cttatattat tgcaacaagc acgcttgatg   32580 cccttcggc aacaatagct ttgtctttg atacacgggg aatacagcaa gccttgtcta    32640
ttcttcagtg ggctcgcgat tatggatccg gaaccgtgcc caatgcagat ggatatcgca   32700
caaaactatc tgctcttata acaatattag aacctttac ccgtacacac cccccagtac    32760
ttttaccatc tcacgtttct actatagatt cccttatatg cgaacttcat cggactgttg   32820
gcattgccgt tgacctgctt ccccagcacg tccgtccttt ggttcctgac cgtccttcta   32880
ttacaaatag cgttttttta gcaactctct attatgatga actttacggt cgttggaccc   32940
gactggataa aacatcgcag gcgttggttg aaaattttac atccaacgcg ttagtggttt   33000
ctcggtacat gttaatgtta caaaattttt ttgcgtgtcg ttttatcca acgccagatc    33060 ttcaggctgt tggtatctgt aacccaaagg ttgaacgcga tgaacaattt ggggtatggc   33120
gtttaaacga tcttgctgat gcggttggtc atattgttgg acaatacaa ggaatccgaa    33180 cgcaaatgag agtgggaata tccagcctgc gcacaattat ggccgatgct tcctcagccc   33240
ttagggaatg tgaaaattta atgactaaaa cctccacttc tgctattggg cctctttttt   33300
caacgatggc ttcccggtat gcacggttta cacaggatca aatggacatt ttaatgcgtg   33360
ttgacaaact aacaacagga gaaaatatac ccggtcttgc aaatgtagag atttttttaa   33420
ataggtggga acgaatagca acagcttgta ggcatgccac ggcagtcccg tcggccgaat   33480
ctattgcaac cgtgtgtaat gaattgaggc gcggtttaaa aaatatacaa gaggatcgtg   33540
taaatgcccc aacctcatat atgagtcacg cccgaaatct ggaagatcac aaggcagcag   33600
tttcattcgt tatggactcc aggcaacagt ttattgtgga ttctggacct cagatgggcg   33660
cggttttaac ttcacaatgt aatataggaa catgggagaa tgtaaatgca acgttttac    33720 atgataatgt taaaataacg acaacggtca gagacgtaat ttcagaggct ccgacgctga   33780
taataggaca aagatggctt cgtccagatg agatttatc taatgtagat ttgcgtcttg    33840
gcgtacccgg gaatacaagt gggagtgacc cttaatataa aacaggcgtg tttatgtaca   33900
ttaaagtatt tgtggttttt attgactggg cgtttcgttt gtataacgct gttgttgcta   33960
gtattttcat aacctcctag gtttttggag ctacacgtgc ttattcaacg ctctttggga   34020
tttgaatcat cgtaaacgta gcgtccctac cagttgagcg cgtaatttc gtaagcaata    34080 aaatggatat aattccgcct atagctgtca ctgttgcggg agtgggaagc cgtaatcaat   34140
ttgacggtgc cctgggaccg gcgtcaggtc tgtcatgttt aagaacatct ttatcgtttt   34200
```

```
tgcatatgac atatgcgcat ggaattaatg caaccctgtc atcagacatg attgatggat    34260
gtttacaaga gggtgcagca tggactacgg atctgtctaa tatggggagg ggtgtcccag    34320
atatgtgtgc tcttgttgat ctccccaatc gaatttcata tattaaactg ggggacacta    34380
ccagtacgtg ctgcgttttg tctagaatat acggcgatag ccattttttt accgttccag    34440
acgagggttt tatgtgcaca caaattcccg ctagagcgtt tttcgatgat gtgtggatgg    34500
gacgtgaaga gtcgtataca attataactg tagactcaac gggaatggcc atctatcgtc    34560
agggaaacat atcttttatt tttgatccac atggccatgg gactatagga caggctgtag    34620
ttgttcgggt gaataccacg gatgtgtact cttatatcgc atcggagtat acccaccgcc    34680
ccgataacgt agaatcccaa tgggccgctg cattagtttt ttttgtcacc gcaaacgacg    34740
gtcccgtaag cgaagaagcg ctatcttcgg cagtaacgct tatatacgga agctgtgata    34800
catattttac agatgaacaa tattgcgaaa aactggttac agctcaacat ccgttgcttc    34860
tttcacctcc taattccacg acaattgtgc ttaataaatc gtctatagta cctcttcacc    34920
aaaacgttgg tgaaagtgta tccttggaag caaccctaca ttcaacgtta accaacacgg    34980
ttgcactgga ccctagatgt agttacagcg aggttgatcc ttggcatgcg gttctagaaa    35040
caacctcgac tgggtctggc gttttggatt gtcgtcgtag acgccgtcct tcatggactc    35100
ctccttcaag cgaggaaaat ttagcttgta tcgacgatgg cttggtaaat aatacacatt    35160
ccacggataa tttacataaa cccgctaaaa aggttctcaa atttaaacca actgtagacg    35220
tgccggataa aacacaagtg gcacatgtat taccccgcct acgagaagtt gctaacaccc    35280
cagacgttgt gttaaatgta tccaatgtag atacgcctga atccagtccc acttttcac    35340 ggaacatgaa tgtaggaagc agtttgaaag atcggaagcc atttctattt gaacagagtg    35400
gtgatgtcaa catggttgtc gaaaaactac tacaacatgg gcatgaaatt agcaatggat    35460
acgtacaaaa tgcggtgggt acgttggata ctgttattac cggtcataca aatgttccca    35520
tttgggtaac aaggcccttg gttatgccag acgaaaagga tccattggag cttttattta    35580
acctcaccat tttgcgttta acgggatttg tggtggaaaa tggaacacgt acacatcatg    35640
gtgctacaag cgttgtatca gactttatag gtcccccttgg ggaaatttta acaggatttc    35700
cctccgccgc ggaacttata cgcgttacaa gtttgatatt aacaaacatg ccggggggcgg    35760 aatatgctat taaaactgtt ctccggaaaa aatgtacaat tggcatgctc attatcgcta    35820
agtttggtct agttgccatg cgggttcagg atacaaccgg cgctttacat gccgaactag    35880
atgtgttaga agcggatcta ggaggttcgt cgcccataga cctctattct agactgtcga    35940
caggtcttat aagtatacta aattcgccta ttatttctca tcccggactt tttgccgagc    36000
ttattccaac ccgtacaggg tccctgtctg aacgaatacg tcttctttgt gaattagtct    36060
cggcccggga gacacgctat atgcgtgaac acaccgcgct tgtttctagt gtaaaggctt    36120
tagagaatgc attacggtct acccgcaata aaattgatgc cattcaaata ccagaagttc    36180
cccaggaacc cccggaagaa accgacattc cacccgaaga gttaattcgg cgtgtatatg    36240
agatacgatc cgaagttaca atgctattga cctcggctgt tacagaatac ttcacccgcg    36300
gagtgttata tagcacacgg gccttgatcg ctgaacaatc ccctaggcgt tttcgggtcg    36360
cgaccgcaag tacggcaccc attcaacggc ttttagattc tcttccggaa ttcgacgcta    36420
aattaacggc aatcatatcg tccctgtcta tacaccctcc tcctgagact atacaaaatc    36480
tccccgtcgt atctctgtta aaagagctta ttaaagaagg ggaagattta aacacagaca    36540
```

```
cggctctcgt atcgtggtta tctgtagtcg gggaagctca aaccgcaggt tacttatcca    36600
gacgagagtt cgatgaatta tcacgtacaa ttaaaaccat taatacacgc gcaacgcaac    36660
gggcttccgc ggaagcagag ttgtcttgct ttaatacgct aagcgcggcc gtagaccaag    36720
ccgtaaagga ctatgaaaca tataacaatg gtgaggtcaa gtatcctgaa ataacacggg    36780
atgatttatt agcaacaatt gtacgtgcta cagacgattt ggtgcgacag ataaaaattt    36840
taagtgatcc aatgatccaa tccggtttac aaccttcgat taaaagacga ttggaaacaa    36900
ggcttaaaga ggttcagacg tatgcaaacg aggcccgaac cacacaggac acaataaaga    36960
gtcgaaaaca ggcggcatat aataaactcg ggggttact  tcgcccggta accggttttg    37020
tgggacttag ggctgcagta gatttattac cggaacttgc ttctgagtta gatgtccaag    37080
gagccctggt aaatctcagg accaaagtct tagaggcgcc ggtagagatc cgttctcaac    37140 ttacggtga tttctgggcg ttatttaacc aatatcgaga cattttagaa catcccggaa    37200
acgcacgcac atctgtctta ggaggactgg gagcttgttt tacagctatt atcgaaattg    37260
tgccgatacc tacggagtat agaccatcat tgcttgcgtt ttttggtgac gtggcagatg    37320
tgcttgcatc cgacatcgcg accgtatcta ctaacccgga aagtgagtcc gccataaacg    37380
ctgttgttgc aactcttagt aaagcgacgt tagtttcatc tacagtgcca gccttatcct    37440
ttgtgttgtc gttatataaa aaatatcagg ctttacaaca agaaattacg aatacccata    37500
agttgactga attacaaaaa caacttggag atgacttctc caccctagct gtctcatctg    37560
gacacttgaa gtttatatca tcttcaaatg tagatgatta tgaaataaac gatgcgatat    37620
tatcaataca aacaaatgtg cacgccctaa tggatacggt taaacttgtt gaagttgaac    37680
tgcaaaagct accccccccat tgtattgctg ggacatctac cttatctcga gtagtaaagg    37740
atcttcataa actcgtcaca atggcacatg agaagaagga acaggcaaaa gtgttaatta    37800
ccgattgtga acgtgcacat aaacaacaaa cgactcgggt tttgtatgag cgttggacac    37860
gtgatattat agcatgtctg gaggcaatgg aaacgcgcca tatatttaac gggacagaac    37920
tggcacggtt gcgagatatg gccgctgcgg gagggtttga tatacacgca gtttacccac    37980
aagcacgtca ggttgtagcg gcatgtgaaa ctacagccgt tacggcatta gatactgtgt    38040
ttcgccacaa tccatatacc cccgaaaata caaatattcc accacctttg gctttgttaa    38100
gagggttaac atggtttgat gattttcga ttacggctcc cgtattcacc gttatgtttc    38160
caggtgttag tattgaggga ctccttctgc ttatgcgtat tcgcgcggtt gtgttattat    38220
ccgccgatac gtctattaat ggaataccta actaccgaga tatgatatta cgaacctcgg    38280
gggatctatt acaaataccc gcattggctg ggtatgttga tttttacaca cggtcttatg    38340
atcagtttat aaccgaaagt gtaacgttaa gtgaacttag agcagacatc agacaggctg    38400
ccggggctaa acttacagaa gcaaataagg ctttggagga agtaactcat gttcgggcac    38460
acgaaacggc taaacttgca cttaaagaag gtgtcttcat tacattacca agcgaaggtt    38520
tattgattcg ggctatagag tattttacaa ctttcgatca taaacgattt ataggaacgg    38580
catatgaaag agttttacaa acaatggtag accgcgatct aaaggaggcc aacgcagagc    38640
ttgcacagtt tcgtatggtg tgtcaggcaa caaagaaccg tgcaatacaa attttacaaa    38700
acattgttga tacggccaat gccactgagc aacaagaaga cgtggatttc actaacctga    38760
agacgttatt aaaactaacc cccccctccca aacaattgc attggccatt gatagatcta    38820
cttccgttca ggacattgtc acgcagtttg cattgctgtt agggcgtctg gaagaagaaa    38880
ctggtacgtt ggacattcag gcggttgact ggatgtacca agctcgcaat attattgact    38940
```

```
cccatccact aagtgtgcgt atagacggta ccggcccct gcatacttat aaagataggg   39000
tggataaact ttatgcgtta cgaactaaat tagatctcct acgacgacga atagaaaccg   39060
gtgaggttac gtgggacgat gcatggacaa catttaaaag agaaacgggg gatatgttgg   39120
catcggggga cacgtacgct acttccgtag atagtataaa ggcactccag gcatcggcgt   39180
ctgtggttga catgctttgt tccgaacccg aattttttt attgcctgtg gaaacgaaaa   39240
accgtctcca aaaaagcaa caggaacgta aaacggcgtt ggatgttgtg ttgcaaaaac   39300
aaagacagtt tgaagagacc gcgtctcgct tacgagcttt aattgaacgt attccaacgg   39360
agagtgacca tgacgttctt cgtatgttat tacgtgattt cgatcaattt acacatttgc   39420
ctatatggat aaaaacacag tatatgacat ttcgaaattt actcatggta cggttaggct   39480
tgtatgcaag ttatgctgag attttccac ccgcgtctcc aaacggagta tttgctccta   39540
ttcccgccat gtcgggtgta tgtctagaag accaatcccg atgcattcgc gcgcgggtgg   39600
ccgcgtttat gggggaggcg tctgtggtgc aaacgtttag ggaagccaga tcttctatag   39660
acgctttgtt tggaaaaaat ttaaccttt acttggatac tgatgggtt ccacttcgat   39720 atagagtgtg ttataaatca gttggggtta aacttggaac catgctatgc agtcagggtg   39780
gattatcttt cgaccggca cttcccgatg aaggtattgt ggaagaaact acactatcgg   39840
cattacgcgt ggccaatgag gtcaatgagc tacgcattga atacgaatcc gctataaaat   39900
ccgggttttc tgccttttcc acctttgtta ggcatcgcca cgccgaatgg ggtaaaacca   39960
acgcacgcag agccattgca gagatatacg ccggccttat aacaacaaca ttgacacgac   40020
aatacggggt tcattgggac aagcttattt attcttttga aaaacaccac ctaacttctg   40080
taatgggcaa tggactaact aaaccaatcc agagaagggg tgatgtacgc gtattagagt   40140
taaccctatc tgatattgta actattttgg ttgccacaac cccggtacat cttctcaatt   40200
ttgctagatt ggatttaatt aaacagcatg agtatatggc ccgtaccctc agaccgtaa   40260 tcgaggccgc atttagaggt cgtttactcg ttcgctcatt ggatggagac ccgaaaggca   40320
atgcccgggc cttttttaat gccgccccat ccaaacataa actcccgtta gctcttggat   40380
caaaccaaga tcctaccggc gggagaatat ttgcatttcg gatggcagat tggaaacttg   40440
ttaaaatgcc acagaaaata acggatcctt ttgcgccatg gcaactttcc cccccccg   40500 gggtaaaggc caatgtcgat gcagttaccc gtataatggc aacagatcgt cttgcgacca   40560
ttactgtact tgggcgcatg tgtctcccgc caatttcctt agtgtcaatg tggaatacgc   40620
tgcaaccgga ggaattcgca tacagaacac aagatgatgt ggacattata gttgatgcga   40680
gactggattt gtcatccacg cttaatgcaa gatttgatac cgctcccagc aataccacgt   40740
tagagtggaa tacagaccgt aaagtaatta cagatgctta tattcaaacc ggggcaacga   40800 cagttttttac agtaacgggg gcggcaccaa ctcacgtttc taatgtaaca gcgtttgaca   40860
tagcaactac ggctatttta tttggggctc ctttggttat tgccatggaa cttacatccg   40920 tttttttcaca aaattccgga cttactttgg ggttaaaatt attcgattcc cggcatatgg   40980
ctacagattc gggtatatcc tcagccgtat ctcccgatat tgtttcttgg gggttacgtt   41040
tactgcatat ggatcctcac ccaattgaaa atgcatgttt aattgtccaa ctagaaaaac   41100
tgtccgcgct cattgcaaac aaacctctta caaacaatcc cccgtgttta ctgctattgg   41160
acgaacatat gaatccctct tatgttttat gggaacgaaa agactcgatt ccagctccgg   41220
attatgtggt cttttggggg ccagaatctc ttattgattt gccgtacatc gactccgatg   41280
```

-continued

```
aggactcttt cccctcgtgt cccgatgatc catttactc gcaaattatt gccggttatg    41340
cgccccaagg ccccccaaac ctcgacacaa ctgatttta cccaacggag ccactattta    41400
agtctcccgt tcaagttgtt agaagttcca aatgtaaaaa aatgcccgtc cggcccgcgc    41460
agcccgcgca gcccgcgcag cccgcgcagc ccgcgcagac cgtccagccc gcgcagccca    41520
tagaaccggg cacacaaata gtggtacaaa attttaagaa accccaaagc gtaaaaacaa    41580
cccttagcca aaagatatt cccttgtatg tggaaaccga atcagaaacg gctgtgctta    41640
tacctaagca attaaccacc tccattaaaa caaccgtttg taaagtatt accccaccaa    41700 ataaccaatt gtcggattgg aaaataatc cacagcaaaa ccaaacgtta aaccaagcgt    41760
tcagtaaacc aatacttgag attacctcca ttccgacaga tgactcgata tcttaccgga    41820
cttggattga aaaatcaaat caaacacaaa aacggcatca aaatgaccct cgaatgtata    41880
actccaaaac agtattccac cctgtaaata accaattacc ttcttgggtt gacacggcag    41940
ccgatgcccc ccaaacggac ctattgacaa actataaaac aagacagccg tcgccaaact    42000
ttccgcggga cgtacacaca tggggcgtat cttctaaccc gtttaactca ccgaacagag    42060
acctatatca aagtgatttt agtgaacctt ctgacggcta tagcagtgag agtgaaaatt    42120
ctatcgtact aagtctcgac gaacatcggt catgtcgcgt tcctaggcac gtacgcgttg    42180
ttaatgccga tgtagtcacc ggtcgacgtt atgtccgagg gaccgccttg ggagcactgg    42240
cactgttaag ccaggcatgt cggcgtatga tcgacaacgt tagatataca cgtaaactt    42300 taatggacca cacggaagat atatttcaag gcctggggta tgttaaattg ttattagatg    42360
gaacatatat ataagtagc gcctattaaa gaaaaaaaa aaacaacgat tattttctgt    42420 gtattttat ttacaccta cgacttcttg aagcgtttcc agattgtccc gtgtgtgaca    42480
aggtctgtcc cttaccccc tgggggtat tttgggttgg gggcgggta gactgtggca    42540 cgccttgggc cgcgggcgt gatccggttg ttggctggac agtgcttgac tgtgctccct    42600
gttgcggttg ttgtccagaa gaccccgaca ccacgtgttg ctgttgtcca acggatgccg    42660 acgtcgttg aggtgggggg tgttgcgggg atgatcccga aaacgccaac gcggcgggct    42720
gttgtaaagc agactgatcg gcgctctgtg tttttttgcgg caatatagta ggccccgaga    42780
ttcccaaact catggatgga tttgggggtt gtggtcgtat aatacgcggg ttaaacgtac    42840
gttttaagcc aaccgttggt cttaaccatg tcatagggtc agtctcggca acatggccg    42900 ttcggcgtat cgtatttgca ttatggttag cgcgtgcacg cgcggcactg gccgcgggctc    42960 ccacggtgta aatgcttctg gcatcagcga tgtccacacg gtgaccaggt tgcaaaggtc    43020
cactggcgtt taaagtcgt attaaagcaa cgggggtgta agccgcaatt gcttccaccg    43080
aaaatgtggt ggggttgctg ggatcaaaga ctacacgaga cgatgcgggt tgtgtcatcg    43140
tttattagtt tacgggacaa tcgataacag catacacgta catctgcgca ggatatgtac    43200
ggaaaggcaa tttatttcca gaaaagcacc gccctaata caactaccag tacaattaca    43260
atgaacaggg catatgtcac gttagctacg ggtagagcaa gttccagac acgcgtagtt    43320 tgggtatcgg gtaacgcagg tttaatgtca ctttgcattt gaacagacgt gtttggactt    43380
ccgttctcgg gtgggatct gaatgaaggc cgccagcgta tatattcatc caaattattg    43440 ccagttttcct tatacatgta tgcatccgtg gcgcgggcca taagtttaat ggtgcgagat    43500
ggatcttccg gtcccataaa acgaaaggat aactgaacat atggcattcg cacaaagcag    43560
ttcacccaca ttaaagcctg gagaggtcgg cggtcaatac ccccacctcg tttaattgat    43620
tccaaagcag ataggttgat accggtactt aacgttgaac taagaatcac gttattactg    43680
```

```
tcaatggaca cttcagccac tggtgcgtta gtcggacgaa aaaaaaaacc ttgaaatagc    43740
acagacaccc ccgtattttg aattttttatg taagggtcac aatctacttg cgcccaattc   43800
gccattaaac gcataatata ctctaccgga aaggcttcgg atacgttgtc ttcgccgtta    43860
aactgaaaaa cacaacgggc gggggggcgt tgtggatcaa atattggaag atccccatcg   43920
caacattgaa gagcgcttgg taccaccaac cgaatacgtt gtaaaagatt atctccgcaa    43980
cccctcctgc gttcactccg tacatacgtt ctccgtgaca tattgatcta aggttgcaaa   44040
ccaaggcaca cgcgtgaagt atttagacca tttatcgtgg gatataggag gagtttggag   44100
tgatccaccc cctgacgact tattaatgcg tttattttcc ccatgtatta agcatccttc    44160
aatatttcat gcaaatctag aaatttggcc atgactcccg caaagcgttc acggcgacgg   44220
gtcacgctgg cactatgttc acatggaaca acataagcag attttctga atcgttactt     44280 tctttatgtt ttaaaacgga cgccaggcga ctggtaaatg atatataatt taattgagcg   44340
tcagttgtag gtagaattgc ttctatttcc ggggaatta aattttcaaa ccaaacggaa    44400
agagtaaagg tgctatcagc aggaaaatac tttgactcca gtgcatcgat atttaataga   44460
ttaacatcgg tgtctgtaat taaatcgcgg gccctcatcc cagagatgga tcgggtagaa   44520
tcagaagaac ccatggatgg attcgaatcg cccgtattct ccgaaaatac atcttctaat   44580
tccggatggt gttccgacgc attttccgat tcgtacatcg cttataatcc agcccttctg   44640
ctaaaaaacg atttgttatt ttcagaattg ttatttgcct cccacttaat aaatgttccc   44700
cgtgcaatag aaaacaacgt cacttatgag gcctcttcgg cggtaggtgt ggataatgaa   44760
atgacctcaa gtaccactga atttatagaa gaaattggag acgttttggc gttagacaga   44820
gcctgtttgg tctgcagaac gcttgatttg tataaacgta aatttggact gacaccggaa   44880 tggggttgcgg actacgccat gttatgtatg aaaagtctgg catccccgcc ctgtgcagtt   44940
gtcactttta gcgctgcctt tgaatttgtg tatcttatgg atcgttacta cctgtgccgt    45000
tataacgtta ctttggttgg gtcctttgcc aggcgcacgc tttccctgtt agatatacaa    45060
agacattttt ttttgcatgt atgttttcgt accgatggag ggttaccagg tatacgaccg   45120
ccccccggta aggaaatggc caacaaagta agatattcca attactcctt ttttgtacag    45180
gcggtagtta gggctgcatt actatcgatc agcacgtctc gtttagacga aaccgaaacg   45240
cgtaagtcat tttactttaa tcaggacgga ctgactggag gccctcaacc tttagcggcc   45300
gccttggcta attggaaaga ttgcgcgcgg atggttgact gttcatcatc ggaacatcgc   45360
acaagtggga tgattacctg cgcggaacgt gcattaaaag aggatataga gtttgaagat   45420
atattaatag acaaacttaa aaaatcgtct tacgtagaag cagcttgggg ttacgcagac   45480
ttggctttat tattactgag tggggttgct acttggaatg tagacgagcg tacaaattgt   45540
gctatagaaa ctcgcgttgg atgtgttaaa tcatactggc aggcgaaccg gattgaaaac   45600
tccagggacg ttccaaaaca attttccaaa tttacgagcg aggatgcctg tcccgaagta   45660
gcatttgggc ctattttgtt aactaccta aaaaacgcaa agtgccgtgg tcgcacgaat    45720
accgaatgca tgttatgttg tttattaacc ataggcact attggatcgc tttgcggcag    45780
tttaaaaggg atatattagc atactcagca aataacacaa gttatttga ctgtatcgaa     45840 cctgtaatca atgcatggag cctagataac cccattaaac ttaaatttcc atttaatgat   45900
gagggtcgat tcataaccat tgtaaaagca gcaggttccg aggccgtata taaacattta    45960
ttttgcgatc tcctatgcgc tctctcggaa ttacagacaa accctaaaat tttatttgcc    46020
```

```
catcctacaa ccgcggataa ggaagtgttg gagttatata aagcccaact ggctgcacaa    46080
aacagatttg aaggtcgtgt atgtgctggc ctgtggacat tggcgtatgc atttaaagcc    46140
taccagattt ttccacgcaa accaaccgcc aatgccgcat tcatacgaga tggaggactt    46200
atgcttcgac gacatgcaat atcgctggtc tccctcgaac acaccctatc gaagtatgtc    46260
taggcgatat aaatccgtat ctcggagcgg gccttcgatg cgtgtacgct ccagaacgcc    46320
atgccgccgt caaaccattc gaggaaaact tatgtcaaag gagcggtctg tgtaccgcca    46380
ttattttaat tacatcgcaa ggtccccccc agaagaacta gctaccgtta gaggcttaat    46440
cgtgccaatt attaagacga cccctgtcac ccttccgttt aacttgggtc agacagtggc    46500
ggataactgc ctgtcgttat ccggaatggg ttatcattta ggtctcggag gttattgtcc    46560
gacatgcact gcatctggag aaccgcgtct atgtcgaacc gatcgggcgg ctctgatact    46620
agcatatgtt cagcagctta acaacatata cgaatatcgt gtgtttcttg catccatttt    46680
ggcgctatca gaccgagcca acatgcaagc agcgtccgct gaaccccctat tgtcgagcgt    46740 attggcacaa ccggaattat ttttttatgta tcatattatg agggaggggg gcatgcgaga    46800
tatacgcgta ctttttttatc gtgatggaga tgccggaggg tttatgatgt atgttatatt    46860
tccggggaaa tctgttcacc tccattacag actaatcgat catatacagg ccgcgtgtcg    46920
ggggtataaa atagtcgcac acgtttggca gacaacattt ttactgtcgg tatgtcgcaa    46980
cccagaacaa caaacagaga ctgtggtgcc atccattgga acatcggacg tttactgtaa    47040
aatgtgtgac cttaactttg atggagaatt gcttttggaa tacaaaagac tctacgcatt    47100
atttgatgac tttgttcctc ctcggtgatt tcagcttcag tgttcatttt attatcccag    47160
cacggggcgt gtatacaaac aaagcctgcc gcctgcaagc ggtttagcat tttaacgtta    47220
acaactcgtg tctctggaat aaaacgtttt aaagccgtt ctgtgagttt agtgtcgttt    47280
ccaaataacg ccttaaaagt tacactcgcc gtcccaatga gatgagaaaa ataatagtca    47340
atgtttaaag acagcccgtg tgatgttacg tgaatgggat cttccgctaa gtcagatatt    47400
attaacttac gctttgcttc cccacaccgt ttacctgcgg tattctgtaa aggatctcca    47460
cgtagcaaag ctacactttt tgcatcagcc tccacttcgt ctgtgggggc acaataaca    47520 taagggatgc gttctcgaac gtttgggatt tgaccctgtc tcattactaa tttataatat    47580
actgttaagt gagccaagcg acggtttatg taggcggatg gtggacgact aagctcggcc    47640
gtcataacaa acttattaat atccaatttg ggtgatgtaa tctggcgatg tgcatctgca    47700
attatgcgtc caaacccggc catcccagac ggcatggccc gtctattcca ttcagcaatg    47760
gaaacacacg acgcctccgc cgcagcacgc gagacggtgt cgtcatataa caacagttct    47820
acaagtttgc gggcataatc gttaataaat tgacagttgt ttttttctaac caagtcgact    47880 cccttcatta aaacctttcc gccgtaaatt accccaatgt actttttctt tgttataagc    47940
aaaagtttta taaagttttt ttcacactcc aactttatag gaggacaaaa cagagccgtt    48000
gaaattatat gtgccatttt ctcgccgatt ttagctatcc cctcaacact aacacccttg    48060
aatcggataa acacagaatc cgtatctcca tatataacct ttacctcgta cgcttttttgg    48120 gagagaacgc tactttcaat gtctggaaac gctgtaataa aacgttcaaa tgcggcccag    48180
ttattatgaa tataatctct ggtacttaat aacatttgac ggccaattgt agtgacagtg    48240
gccgctacgt ataaacatgg cagaaatccc tgcgcaactc cagtaaaacc gtacacggaa    48300
ttacaaacta ctttttatcgc ggcttgttgt ttgtctaata acactgcttc atctgaagaa    48360
cttccgggta tgcgcgctct aatagccttg cgcatagcca accagtcttt taaaagaaca    48420
```

-continued

```
cccagcagac tttctcgaac gttagagcgc acaaaaaaaa gacgttttcc tccaactgta    48480
aaggtggcat aatcggatgg attcaaacgt ttaaccgtct caaaatttaa cgttagcgtg    48540
gtaaaacata agttatgggc ctgaattata cttggatata aacttgcaaa atccaatacg    48600
accaccggat cgatataaaa tcccgtatca gggtcaaaaa ccctggctcc tttatatcct    48660
acatttcgcc cacttgacgt accagtggga gaaacgctct cgtcttcatc catctcttcc    48720
tcaacatccc cgacatcggg aataacatcc ttatattcaa aagtagctgg gtatccccca    48780
tcgggtaaaa taaatcctcg agacgaagcc agtcctaata aacaggtgta aatcctaacc    48840
tgctgtccgt cgtaaatagc cttggttaaa gtaattctag ctagccttgc aaccgcggat    48900
aactcaaggt gtggtaaata tttaaaaaac agtttcccca caagagccga gtcttgtata    48960
caatattcac caataattcc tcgtgtattc ggtccactag cgtaatatcc cggaatgtct    49020
ttgtagggca aatctctctt ggactcattt agagcttcac gtgcaaccga atctaattta    49080
taactcgaga gttttaattt ttcagttgca attgcataca tatccagaga tatgagaccg    49140
ttgatcttta ccttgcttcg tcgctgaaat ccggatttgc caacatccca tatcttaaac    49200
agacccccac ggtttatact gccataacca tcaagcttga gactgtatat agaattaagt    49260
ttctccataa taaacgccca atcaaaatta acaatgttat aacctgtggc aaactcggga    49320
gcgtactgtt ttacgagggt cataaatgca attaatagct cgaattcact atcaaactcc    49380
agcacagtcg gctccggtaa ccccgcgtcc ttcatttctt gtacatacct ttgtggtaag    49440
tcacaagagc caagggaaaa cagtaaaatg tgttctaaag actgtcgagg gattgaatat    49500
aatagacaag aaatttggat tacaagatcc tccagatgtg ttgcatcggg aaacgccagc    49560
tcattagatc ctcctgattt acattcaata tcgaaacata acaacttgta gtcaggccat    49620
gagtcatcgt ttggtatagc ctgcagatta tccgacatgc agtcaatttc aacgtcgctt    49680
aacgttaatt ggcgacttgc cggtcgaact cgaacacgtt ccccatcaac tccaggtttt    49740
agttgatacc aaccaaaact aacaaagccg ggattatcca ttagaaaacg agtggtagcg    49800
tctacccgac cttcatactt tttcaactcc gggtgaaagt tatcacaaag ataatttgta    49860
aatttagatg agggagaata caccctgtaa aacgcacatg gctgtgtatc gtagtaataa    49920
acatctgtgc gctcaataac ctcaacgcga aagctttctg gagatgcgct tttaaacgag    49980
gtaccatgaa aagcgttctt gtctccattt aacgttgcat cattttgtgt tatcatagaa    50040
ctgcgtaaac actcggcaag taatacagat aactcgctac cggaacgtat gccacaagcg    50100
gtatccacct cggctttgtt tatataaaaa tattgacaga tgccgtatac atgaactgcc    50160
accctttttc cacatcggga catgccaagt aaagtaataa cggtaccaag cggtcgtgtt    50220
gcagttgcaa accgggatac atctccatta gacgcggctt ctgttgtttc gacaatatca    50280
tatacatgga atgtgttaaa gcgggggtca aacttatccc cacgaaagtc gatttccccc    50340
caaatattca cgcgtctagg ccaggggctg gaacaacgaa atccagaat cggaacttct     50400
tttccattac agtaaacttt aggcggtcga ctaagtgtac cgacgtgaac ccccttttcgt   50460
tcttccatgg gcacatcttc atctaaacat ttaggggcca aaaattgaaa cgatgacatg    50520
gtagttttgt aactatgaag aaattctctg ttactaccgc gcccggttct tgggttatat    50580
ttaatccctg atgcttgggt taaaaggga ttacaaaacc ccgttctgat cgccatttta     50640
tgttaacgat tgataatctt gtaaaagcc agtgttactg agtaacacaa ccccacgccc      50700
ttctaataca taaagtgtaa tcacgtgatt tgttgtggtt tccgcatatg taatacccgt    50760
```

```
ttaaaagcct ctcttcttaa tgtatcgaca gactgggttt tgggtggtca tttgaccctg   50820
ccaacaaccc cccattatta cgagtacttc accaaaatgg aaaatactca gaagactgtg   50880
acagtgccca cggggcccct gggttacgtt tatgcgtgcc gggttgaaga tttggatctg   50940
gaggaaattt cattttttggc cgctcgtagc acggactctg atttggcttt attacctttg   51000
atgcgtaatt tgaccgtgga aaaacttttt acatccagcc tggcggtggt ttctggagca   51060
cgcactacgg gtcttgccgg agctggtatt accttaaaac tcactaccag tcatttctat   51120
ccatctgtct ttgtctttca cggaggcaaa cacgttttac ccagctccgc ggccccaaat   51180
ctcacacgcg cgtgtaacgc ggctcgagaa cggtttgggt tttcacgctg ccaagggcct   51240
cctgttgacg tgctgttga gacgaccggc gctgagatat gcacccgcct tggattagag   51300
ccagaaaata caatattata cttggtggtc acggcattgt ttaaggaagc cgtatttatg   51360
tgcaacgtgt ttctgcatta tggaggactc gatattgttc atattaacca tggggatgtt   51420
atacgtatac cgttatttcc ggtacaactt ttcatgcccg atgttaaccg tctggtaccc   51480
gacccattca acactcatca caggtctatc ggagagggtt ttgtataccc aacccctttt   51540
tataacaccg ggttgtgcca tttaatacat gactgtgtta ttgctcccat ggccgttgcc   51600
ttgcgcgtca gaaatgtaac tgccgtcgcc cgaggagcgg cccaccttgc ttttgatgaa   51660
aatcacgagg gggcagtact cccccctgac attacgtaca cgtatttttca gtcctcttca   51720 agtggaacca ctaccgcccg tggagcgcgt cgaaacgatg tcaactccac gtctaagcct   51780
agcccatcgg gggggtttga aagacggttg gcgtctatta tggccgctga cacagccttg   51840
cacgcagaag ttatattcaa cactggaatt tacgaagaaa ctccaacaga tatcaaagaa   51900
tggccaatgt ttataggcat ggagggcact ttgccaaggc taaacgctct ggggtcatat   51960
accgctcgtg tggccggggt cattggtgcg atggttttca gcccaaattc tgcgttgtat   52020
ctaactgagg tggaggatag cgggatgacc gaagccaagg atgggggacc gggtccatca   52080
tttaatcgat tttaccagtt tgccggacct catttagctg cgaatcccca aacagatcga   52140
gatggccacg ttctatccag tcagtctacg ggttcatcaa acacagagtt tagcgtggat   52200
tatttggcac tcatttgtgg atttggagca cccctgttgg cgcgactgct ttttatcta   52260 gaacgctgtg acgctggtgc gtttacaggg ggtcacgggg atgcgttaaa atatgttacg   52320
gggacctttg actctgaaat tccatgtagt ttatgtgaaa aacacacgcg gccggtatgc   52380
gctcacacaa cagtacaccg acttagacaa cgcatgccgc gatttggaca agccaccccgt   52440 caacctattg gggtgtttgg aacaatgaac agccaatata gcgactgcga tcctctagga   52500
aactatgctc catatttaat ccttcgaaaa cccggggatc aaacggaagc agcaaaggca   52560
accatgcagg acacttatag ggctacacta gaacgcttgt ttatcgatct agaacaagag   52620
cgactactgg atcgcggtgc cccatgttct tccgagggac tatcgtctgt cattgtggat   52680
catccaacgt ttcgtcgcat attagacaca ctgcgtgcgc gtatagaaca gacaacaaca   52740
caatttatga aagtgttggt tgagacccgc gattataaga tccgtgaagg attatccgaa   52800
gccacccatt caatggcgtt aacgtttgat ccatactcag gagcattttg tcccattacc   52860 aatttttttag ttaaacgaac acacctagcc gtggtacaag acttagcatt aagccaatgt   52920
cattgtgtat tttacggaca gcaagttgag gggcggaact ttcgtaacca attccaacct   52980
gttttgcggc ggcgttttgt tgacctgttt aatgggggt ttatatcaac acgctctata   53040
accgtaacat tatctgaagg tcctgtatcc gccccaaatc cgacattggg acaagacgcg   53100
cccgcggggc gtacctttga tggggattta gcgcgcgtaa gcgtggaagt tattcgggat   53160
```

```
atacgagtta aaaataggqt cqttttttca qgtaactqta caaatctctc tgaqqcaqcc  53220
cgggcaaggc ttgtaggcct tgcaagtgcg taccaacgcc aagaaaaaag agtggatatg  53280
ttacacgggg ccctagggtt tttgcttaaa cagtttcacg gcctgttatt tcctcggggt  53340
atgccaccaa acagtaaatc ccccaacccg cagtggtttt ggaccctgtt acaacgcaac  53400
cagatgccgg cagataaact tacacacgaa gagattacca ctattgcagc tgttaaacgg  53460
tttaccgagg aatatgcagc aataaacttt attaatctac ccccaacctg cataggagaa  53520
ttagcccagt tttatatggc aaatcttatt cttaaatact gcgatcattc acagtacctt  53580
ataaatacct taacttctat aattacgggt gccaggcgcc cgcgtgaccc atcatccgtt  53640
ttgcattgga ttcgtaaaga tgtcacgtcc gccgcggaca tagaaaccca agcaaaggcg  53700
cttcttgaaa aaacggaaaa cttaccggaa ttatggacta cggcttttac ttcaactcat  53760
ttagtccgcg cggccatgaa tcaacgtccc atggtcgttt taggaataag cattagtaaa  53820
tatcacggag cggcaggaaa caaccgcgtc tttcaggcag ggaattggag cggtttaaac  53880
gggggtaaaa atgtatgccc gctatttaca tttgatcgca ctcgccgttt tataatagca  53940
tgtcctagag gaggttttat ctgccccgta acaggtccct cgtcgggaaa tcgagaaacc  54000
accctatccg accaagttcg cggtataatt gtcagtggcg gggccatggt tcaattagcc  54060
atatacgcca cggttgtgcg tgcagtgggc gctcgagcac aacatatggc atttgacgac  54120
tggttaagtc ttacagacga tgagttttta gccagagact tggaggagtt acacgaccag  54180
attatccaaa ccctggaaac gccctggacc gtagaaggcg ctctagaagc agtaaagatt  54240
ctagatgaaa aaacgacagc gggagatggg gaaaccccca caaacctagc atttaatttt  54300
gattcttgtg aaccaagcca tgacaccaca tctaacgtat taaacatttc agggtcaaac  54360
atttcagggt caactgtccc tggtcttaaa cgaccccccg aagatgacga actctttgat  54420
cttagtggta ttcccataaa acatgggaac attacaatgg aaatgattta acctccctct  54480
ttatccaatt aaagcccaca cgcgggtgag tgtacgtaat aaacaagtca atattacata  54540
ttctgttgtg ttttcttttt ttgtgtgtag tccttaccca tatgacctgt aatatagtgt  54600
gtctccaacc attcagctta cagtccagtg gacagtaaca gcccgataac atggaattgg  54660
atattaatcg aacattgttg gttctactgg gtcaagttta tacgtacatc tttcaggttg  54720
aactgctacg tcgatgtgat ccaagggtgg cgtgtcgctt tttatatcgg ttagcggcta  54780
actgtttgac agttcgttat ttattaaagc tgtttctccg gggatttaat acccagctaa  54840
aatttgaaaa cactcccacg gtttgtgcac tgcattgggc attatgttat gtaaagggag  54900
aaggtgagcg tttgtttgag ttgctacaac atttttaaaac gcgttttgtt tatggtgaga  54960
ctaaagactc aaactgtatc aaagattact ttgtctcagc gtttaactta aaaacctgcc  55020
aatatcacca tgagctgtcg ttaacaacat acggaggtta cgtatcgagt gaaattcagt  55080
ttttacacga cattgagaat ttttttaaaac agcttaatta ctgctatatt atcacgtctt  55140
ctcgtgaggc gctaaacaca ttggaaaccg tgacgcggtt tatgacagat actataggaa  55200
gcggtctaat accaccgtg gagttgtttg atccggcgca tccatgtgct atatgttttg  55260
aagaattatg tataacagct aaccaaggtg agaccttaca tcgtagatta ttaggatgta  55320
tctgcgatca cgttactaag caagttcggg ttaacgtgga tgttgacgat attattcggt  55380
gtttaccata tatccctgat gtaccggata tcaaacgtca atccgccgtt gaagcgttac  55440
gaacacttca aaccaagacg gtagtcaatc ccatgggagc aaagaacgat acgtttgacc  55500
```

```
aaacatacga aattgcgagc accatgcttg attcttatat tgttttaaa cctgcccctc    55560 ggtgtatgta cgccatcagc gagcttaaat tctggttaac gtctaattcc actgaaggac    55620
cccaacgtac tttagacgtg tttgttgata atttggatgt attaaacgaa catgaaaaac    55680
acgcagaact tacagccgta acggttgagt tggcgttatt tggaaaaact cccatacact    55740
ttgataaggc gttttctgaa gaactcggat ctctggatgc aattgatagt attttggttg    55800
gcaatcgctc atcctcacca gacagtcaga tagaagcatt aattaaagcc tgttatgccc    55860
atcatctatc gtcgcctctc atgcgtcaca tttctaaccc gagtcatgat aacgaagccg    55920
ccttacgcca acttttagaa agagttgggt gtgaggatga tttaaccaaa gaggcgagtg    55980
acagcgctac agcatccgaa tgtgatctga acgatgatag tagcataact tttgctgttc    56040
atggatggga aaacctgtta tccaaagcaa aaattgacgc tgcggaaaga aaacgagtat    56100
atcttgaaca tctgtctaag cgctctctaa ccagcctcgg tagatgtatc cgcgaacagc    56160
gccaagagct agaaaaaaca ctcagggtaa acgtttatgg agaggcctta ttgcagacat    56220
ttgtttcgat gcaaaatggg tttgggggcac gaaacgtgtt tttagctaag gtttcccagg    56280
cagggtgtat tatcgacaat cgcattcagg aagcggcctt tgatgcacat agatttataa    56340
ggaataccct agttcgacat acagtagatg cggctatgtt acctgcactt acacataaat    56400
tttttgagtt ggtcaacggc ccattgttta atcacgatga acaccgtttt gcacaacccc    56460
ctaacaccgc cttatttttt accgtggaaa acgttggcct atttccgcac ttaaaagagg    56520
aattggcaaa gtttatgggc ggtgtcgttg gttccaactg gcttctcagt ccatttaggg    56580
gcttttattg cttttctggg gtagaaggcg ttacttttgc acagagactt gcctggaaat    56640
atattaggga gcttgtgttt gcaaccacac tattcacctc tgttttccat tgtggggagg    56700
tgcggttatg tcgcgttgac cgtctaggta aggatccacg cgggtgcacg tctcaaccta    56760
aaggtatagg cagttcccac ggacccttag acggcattta tttaacgtac gaagaaacat    56820
gtccccttgt ggctattatt caaagtggag aaacagggat cgaccagaat accgtcgtaa    56880
tctacgattc agacgttttt tctcttctat acaccctaat gcagcggctg gctccggatt    56940
caacggaccc ggcgttttca taacctccgt tacgggggtg tggttatgct ttttatgcat    57000
attttctatg tttgttacgg cggttgtgtc ggtctctcca agctcgtttt atgagagttt    57060
acaagtagag cccacacaat cagaagatat aacccggtct gctcatctgg gcgatggtga    57120
tgaaatcaga gaagctatac acaagtccca ggacgccgaa acaaaaccca cgttttacgt    57180
ctgcccaccg ccaacaggct ccacaatcgt acgattagaa ccaactcgga catgtccgga    57240
ttatcacctt ggtaaaaact ttacagaggg tattgctgtt gtttataaag aaaacattgc    57300
agcgtacaag tttaaggcga cggtatatta caaagatgtt atcgttagca cggcgtgggc    57360
cggaagttct tatacgcaaa ttactaatag atatgcggat agggtaccaa ttcccgtttc    57420
agagatcacg gacaccattg ataagtttgg caagtgttct tctaaagcaa cgtacgtacg    57480
aaataaccac aaagttgaag cctttaatga ggataaaaat ccacaggata tgcctctaat    57540
cgcatcaaaa tataattctg tgggatccaa agcatggcat actaccaatg acacgtacat    57600
ggttgccgga accccggaa catataggac gggcacgtcg gtgaattgca tcattgagga    57660
agttgaagcc agatcaatat tcccttatga tagttttgga ctttccacgg gagatataat    57720
atacatgtcc ccgttttttg gcctacggga tggtgcatac agagaacatt ccaattatgc    57780
aatggatcgt tttcaccagt ttgagggtta tagacaaagg gatcttgaca ctagagcatt    57840
actggaacct gcagcgcgga acttttttagt cacgcctcat ttaacggttg gttggaactg    57900
```

```
gaagccaaaa cgaacggaag tttgttcgct tgtcaagtgg cgtgaggttg aagacgtagt    57960
tcgcgatgag tatgcacaca attttcgctt tacaatgaaa acactttcta ccacgtttat    58020
aagtgaaaca aacgagttta atcttaacca aatccatctc agtcaatgtg taaaggagga    58080
agcccgggct attattaacc ggatctatac aaccagatac aactcatctc atgttagaac    58140
cggggatatc cagacctacc ttgccagagg ggggtttgtt gtggtgtttc aacccctgct    58200
gagcaattcc ctcgcccgtc tctatctcca agaattggtc cgtgaaaaca ctaatcattc    58260
accacaaaaa cacccgactc gaaataccag atcccgacga agcgtgccag ttgagttgcg    58320
tgccaataga acaataacaa ccacctcatc ggtggaattt gctatgctcc agtttacata    58380
tgaccacatt caagagcatg ttaatgaaat gttggcacgt atctcctcgt cgtggtgcca    58440
gctacaaaat cgcgaacgcg cccttt ggag cggactattt ccaattaacc caagtgcttt    58500
agcgagcacc attttggatc aacgtgttaa agctcgtatt ctcggcgacg ttatctccgt    58560
ttctaattgt ccagaactgg gatcagatac acgcattata cttcaaaact ctatgagggt    58620
atctggtagt actacgcgtt gttatagccg tcctttaatt tcaatagtta gtttaaatgg    58680
gtccgggacg gtggagggcc agcttggaac agataacgag ttaattatgt ccagagatct    58740
gttagaacca tgcgtggcta atcacaagcg atattttcta tttgggcatc actacgtata    58800
ttatgaggat tatcgttacg tccgtgaaat cgcagtccat gatgtgggaa tgattagcac    58860
ttacgtagat ttaaacttaa cacttcttaa agatagagag tttatgccgc tgcaagtata    58920
tacaagagac gagctgcggg atacaggatt actagactac agtgaaattc aacgccgaaa    58980
tcaaatgcat tcgctgcgtt tttatgacat agacaaggtt gtgcaatatg atagcggaac    59040
ggccattatg cagggcatgg ctcagttttt ccagggactt gggaccgcgg gccaggccgt    59100
tggacatgtg gttcttgggg ccacgggagc gctgctttcc accgtacacg gatttaccac    59160 gttttatct aacccatttg ggcattggc cgtgggatta ttggttttgg cgggactggt    59220
agcggccttt tttgcgtacc ggtacgtgct taaacttaaa acaagcccga tgaaggcatt    59280
atatccactc acaaccaagg ggttaaaaca gttaccggaa ggaatggatc cctttgccga    59340
gaaacccaac gctactgata ccccaataga agaaattggc gactcacaaa acactgaacc    59400
gtcggtaaat agcgggtttg atcccgataa atttcgagaa gcccaggaaa tgattaaata    59460
tatgacgtta gtatctgcgg ctgagcgcca agaatctaaa gcccgcaaaa aaaataagac    59520
tagcgccctt ttaacttcac gtcttaccgg ccttgcttta cgaaatcgcc gaggatactc    59580
ccgtgttcgc accgagaatg taacgggggt gtaaatagcc aggggg tttg ttttaattta    59640 ttaataaaaa tgtgtattac gttactcatg tgtctccatt acgcatcaca gggggtattt    59700 atcccgata atatacaaaa cgcgttttgt acctctaccg cacccgatat cttaacgggg    59760
ttattatgga atcgtctaac attaacgcgc tacaacaacc gtcgtctatc gcacatcatc    59820
cgtccaaaca gtgcgcttca gtctcaatg aaacagtaaa agattctccc cccgcgattt    59880
atgaagatag gttagaacac acgccggtac aattaccccg cgacgtaca ccccgagacg    59940 tatgttctgt gggacagcta acctgtcgag catgtgcaac gaaaccttt tcgccttaacc    60000 gcgacagcca atacgactac ttaaacacat gtccaggggg ccgtcatatt tcactggcac    60060
tggagattat aacgggtcga tgggtttgca tcccgcgtgt gtttccggat accccagagg    60120
aaaaatggat ggcgccatat attattccag accgagaaca accatcatca ggggatgaag    60180
attctgacac cgattaaatt taacttaaat aaaaccttac cacccataaa aacgcct tct    60240
```

```
gtttgtttaa cacgacaccg cttaacaaaa aaaaaaaaac caaacacgcc ttttatgaat    60300
gtaatacttt tatttgttgg ttaacaccgc cccaccatca tctgatttgc aaacatatcg    60360
gcgtcgtctg ccgtggaccc ctgtattaaa ggggccttgg aactcgcctc cactgcattt    60420
acatcttgtc caactgtatc tgtatgtggg gtgcttgttg tattttggga tgagcataga    60480
cccgaaacgc tttgaagctg ttttaataaa atcgatattc gaggatcccg tgtcccctct    60540
ggtatatttg tatggtgcga caaaggcatt tgtgtcccat tttgtgattt tagctctgta    60600
acctcctgtt gcagttttgc cacaacccca gcaagctctt cgtgctgacc attagaaact    60660
ctgtgtctcc tctgccaata tgatggagaa actcgacgtc tccgatgcgt tatatacgtt    60720
ggttcaccgg gaaatatat atttgaggga aactctccgt ccatttgaga ctccccacta    60780
taaaaagaat ccaattccct ttgatccatg ctcttgaaat cccgttttcc tggacgacgg    60840
acatcggttt tgtctggaaa atttacacac ggggtctgca agtcaatacc ccgttcggcg    60900
gccaatgcgt tcataaatgc ggacatttgc atttccaaac gattgggtgg tggatatccc    60960
ggaaacccgt acgtccccc gaagtgtccc ggagggcaac cataacccc tgtattaggt    61020
gggaaggcag gcgggtgtgg agatccatat ggcccgacga tatactgtcc gttatttgga    61080
gctccaattg atacctgcgg atttttagtc tgcccggtta acagctgtga ataatacgcg    61140
gtaggtatca gtacaaattc ccctccggtt ggaacgcccg acggggctg tggtgagata    61200
ttactagcgt tacctgctac agaagccata tcgctgtcgt tcctacacaa ctgcgtaacc    61260
tttaaatgcg gaacagtctt ttcacaatct tcatttgatt ccccaacacc caacgcgaga    61320
tcgtatatgg gcccgccggg gtggaatgtg gcgtttataa cacccgcgtt gggtaattta    61380
gactccaccc cattaacgtt ggttatccga gcaagtccat atccggtgct agcctgaaga    61440
taaacgtgac ccataattcc ggcttcgcgt ctacgttttg caaccacgtc ccatctatct    61500
cttaaaagca tattgttcac ggctgtggat aataacacct tggcgagttt atcttcgcta    61560
accttccata ctttatttaa acccgcgtag tctttaacca gcgacaataa ccgcgcttta    61620
cttttccatcg ataaaacccg gaatggttca attgaagatt ccggggtaca gtcataattg    61680
accactgttc caacgcgtct tccaacaaca cataacgcaa catgggtaaa aaaattaccg    61740
tctggtatct cattcgggga caatcgtttt gaagacaggg atacggaggg taagtaattt    61800
gtgaccaagt ataacgcacg ttctagcgga gataatacag aatctctatt tccaaaaaaa    61860
ttcgaatggg ccgcttcaaa cagcaccgca tgtagttgag ggcatctaac gatacccaaa    61920
aaaaaggtc cgcgtatgtc ctcaatgatt gcgattactt cacccacgac acagtctttt    61980
cgatgatcga tgtttattgg tattttacta gtaggcggca aagcggaccg cacaatctct    62040
ggggtaatat ttaattcccc ttcgtccttt gaatataagg ctaaataccc agccacgtat    62100
aacgcttcac agttctcttc gtcagcttca gcagccatta taaacacccc acggaccgga    62160
tagtgaatac tcacggtgtg gaggcaaact gaggaatgac acccaaacag acaaaatata    62220
gaagatcata gtcactgtta acgttgaact gcgcaaggcg gcgactttct tccaatgccg    62280
cccttacacg cggttggtgc attaacattc caagtccccg ttcatattgc aacataacac    62340
tgtcatgtat tgataccacg gcggctatgg gtagggatgt aacattttgt cggcggtgtt    62400
ctaattccaa tgcaattaag cttatgagcc gatcttggta ctgtccagaa gaaatatcta    62460
ttacggttct tcctaaactt ccacgactaa gctgggtatg cgcgtctaaa caaagagcaa    62520
ctaatccagg aaacatttca gtcagctctg tggtccgatt taacgtatac agtggtgcta    62580
tatatcgttc acataaaaat tgaaagttat tattaccgct tttaaacttc ccatcaaacc    62640
```

```
ccgtcgctcc gcgcaagatt acattgttgg tagggttcc tgttgcttct gacacaatca    62700
aacccagttg aaaattattt tttagtttat ctccgtatac gttcccgttc cataataagc    62760
gccttaataa taataacgcc gtaatcgtgt caattgttaa ccttaataga gtttggtctt    62820
ccataagaaa cacgttttgg gcccgttcta aatacgccgc ggccgcctgt tgaatcttgt    62880
ccacatatgc ggtatgattg cgatcaataa tgtcattaac cccaggatta aactgtccag    62940
gtgcaggcgg taggacctgc aaccgtataa gcgcatccat aacagaatgt gacgttaagg    63000
cgccttgatc ataccgcccc ccacgagcat gaaactggtc gcgtggtaga cgatcatagc    63060
aaaattgata actgttttta ttttcgtgtg ttgtcatata attcacaaat gtctcagtat    63120
attccggtag gtgctctata aggttcccga aggacgaaac ttgaggttcg tggacactat    63180
tagatgtcct atacattaaa tataaacata ataccgcaca ctcgaacgcg gagtacgctc    63240
tatctccaac atacattctc ccggcggact gtagacatgt taccgttgtg ttcataaacg    63300
tacgggaaat gcgcccgtct ttacaatcaa ctccgcgtgc agctacgggc ctatctaaca    63360
caagccgttc ctgcagagta cgataccatg gcccgaaaac aatccctgga gagttattgc    63420
cccttgccct tcccaagtac accagggtga taaaatccac ttgaaagttt gtatcgtact    63480
gcaacggtgc atcattttttg gcaatctgta cctcggggtg tatagactca ttgcgtatta    63540
tttctgtacg tgtacattcc tcagattgtg catctgcttc ttccgcctcg gcagcagccg    63600
tctccaggga atccaaaacc ttggccatgc gcgttagttg ttcttcgagg ggctttaaac    63660
gacgatctat ttccgttggt aacgtaatcg tttccccgcg aaggttgtct aatgcggcaa    63720
cggccgccgc attttttaac gttaacgtat ttttttccaa atcgggattc atacgccctc    63780
ttaactcaaa cgcgggagcc gtccagtagt gtatgggaa gttgggggct ataaagttct    63840
tagtggtaga caaaaatatc ccacatttat tcggaaacga gatagatccg aacccatatc    63900
tcgccgtcat ggtgtctgca gcaaacaaag tcaactggcg tgaatataaa ccggtactgc    63960
tttaaaagct gttttcttac ccatgggaaa acatcccggt tatactttgt aaaattccac    64020
cacaagcacc taaagaaggc cttctaaggg gtaaatccac cccacaagct gcattttctt    64080
caaactttgt taaagcggaa cgatggcatg atttcgcacg ctttttcgca agagaacata    64140
cgtgaatttt cttttttgcat agacgtcttc gctctctaac ggaccttatc gggggggtat    64200
attccgctac attctccaaa tgcgacgcta gcataacaag gtttccatga atcacctttg    64260
ggggtaaccg agttacctgt aacaggttca gaccccgttg agatacaaac acaaggaggg    64320
gggtcaccat tatttcatca gatcccgtgg gtgtggtttc ctttattaaa gccatggtat    64380
ccctcagctg gcgcataccc tcgcaaaact ggtgatactt agtagggta tgtatattag    64440 cgctaaaacg gcaagatttt aattccacta taaaacaaac ggtctttccg gcaccactgg    64500
attccgtttg tataatacaa acacaatcgg ggcgtcggcg tcccaaattt acttcaaacg    64560
acattgatat gcgtacagcc ctttgaacat ccacgtggga taacgcgac aggagttttg    64620 ccagcctcgg gttgaacgcg tccgcgaaac ctcgacgtac gttatcaata tccttttga    64680 gtacatcgta aaaacgagtg tggcaacgtt gtcccaaacg aaaacacttg gcccgaattc    64740
gactagcgga catatttgaa gttccgtccc agaagataac ctaagacgcg tttgtctaca    64800
ataaacatgt caacggataa aaccgatgta aaatgggcg ttttgcgtat ttatttggac    64860
ggggcgtatg gaattggaaa acaaccgccg gccgaagaat ttttacacca ctttgcaata    64920
acaccaaacc ggatcttact cattggggag ccctgtcgt attggcgtaa ccttgcaggg    64980
```

```
gaggacgcca tttgcggaat ttacggaaca caaactcgcc gtcttaatgg agacgtttcg    65040
cctgaagacg cacaacgcct cacggctcat tttcagagcc tgttctgttc tccgcatgca    65100
attatgcatg cgaaaatctc ggcattgatg gacacaagta catcggatct cgtacaagta    65160
aataaggagc cgtataaaat tatgttatcc gaccgacacc caatcgcctc aactatatgt    65220
tttcccttgt ccagatactt agtgggagat atgtccccag cggcgcttcc tgggttattg    65280
tttacgcttc ccgctgaacc ccccgggacc aacttggtag tttgtaccgt ttcactcccc    65340
agtcatttat ccagagtaag caaacgggcc agaccgggag aaacggttaa tctgccgttt    65400
gttatggttc tgagaaatgt atatataatg cttattaata caattatatt tcttaaaact    65460
aacaactggc acgcgggctg gaacacactg tcattttgta atgatgtatt taaacagaaa    65520
ttacaaaaat ccgagtgtat aaaactacgc gaagtacctg ggattgaaga cacgttattc    65580
gccgtgctta aacttccgga gctttgcgga gagtttggaa atattctgcc gttatgggca    65640
tggggaatgg agacccttc aaactgctca cgaagcatgt ctccgttcgt attatcgtta    65700
gaacagacac cccagcatgc ggcacaagaa ctaaaaactc tgctaccca gatgaccccg    65760
gcaaacatgt cctccggtgc atggaatata ttgaaagagc ttgttaatgc cgttcaggac    65820
aacacttcct aaatatacct agtatttacg tatgtaccag taaaaagatg atacacattg    65880
tcatactcgc gtgtacgtgt ttttcttttt tatatatgcg tcatttatta ccacatcctt    65940
taatcccgcc tttatctccc taaaacggag tggtaatatt aaaagccgcc aagcctgttg    66000
gtgggtgagg agggtaaag gcacgctgtg tgcataacgt tgcggtgata ttgtagcgca    66060
agtaacagcg actatgtttg cgctagtttt agcggtggta attcttcctc tttggaccac    66120
ggctaataaa tcttacgtaa caccaacccc tgcgactcgc tctatcggac atatgtctgc    66180
tcttctacga gaatattccg accgtaatat gtctctgaaa ttagaagcct tttatcctac    66240
tggtttcgat gaagaactca ttaaatcact tcactgggaa aatgatagaa aacacgtttt    66300
cttggttatt gttaaggtta accctacaac acacgaagga gacgtcgggc tggttatatt    66360
tccaaaatac ttgttatcgc ataccatttt caaagcagaa catcgagcac cgtttcctgc    66420
tggacgtttt ggatttctta gtcaccctgt gacacccgac gtgagcttct ttgacagttc    66480
gtttgcgccg tatttaacta cgcaaatctct tgttgcgttt actacgttcc caccaaaccc    66540
ccttgtatgg catttggaaa gagctgagac cgcagcaact gcagaaaggc cgtttggggt    66600
aagtctttta cccgctcgcc caacagtccc aagaatact attctggaac ataaagcgca    66660
ttttgctaca tgggatgccc ttgcccgaca tactttttt tctgccgaag caattatcac    66720
caactcaacg ttgagaatac acgttcccct ttttgggtcg gtatggccaa ttcgatactg    66780
ggccaccggt tcggtgcttc tcacaagcga ctcgggtcgt gtggaagtaa atattggtgt    66840
aggatttatg agctcgctca tttctttatc ctctggacca ccgatagaat taattgttgt    66900
accacataca gtaaaactga acgcggttac aagcgacacc acatggttcc agctaaatcc    66960
accgggtccg gatccggggc catcttatcg agtttattta cttggacgtg ggttggatat    67020
gaattttca aagcatgcta cggtcgatat atgcgcatat cccgaagaga gtttggatta    67080
ccgctatcat ttatccatgg cccacacgga ggctctgcgg atgacaacga aggcggatca    67140
acatgacata aacgaggaaa gctattacca tatcgccgca agaatagcca catcaatttt    67200
tgcgttgtcg gaaatgggcc gtaccacaga atattttctg ttagatgaga tcgtagatgt    67260
tcagtatcaa ttaaaattcc ttaattacat tttaatgcgg ataggagcag gagctcatcc    67320
caacactata tccggaacct cggatctgat ctttgccgat ccatcgcagc ttcatgacga    67380
```

```
actttcactt cttttggtc aggtaaaacc cgcaaatgtc gattatttta tttcatatga   67440
tgaagcccgt gatcaactaa agaccgcata cgcgctttcc cgtggtcaag accatgtgaa   67500
tgcactttct ctcgccaggc gtgttataat gagcatatac aaggggctgc ttgtgaagca   67560
aaatttaaat gctacagaga ggcaggcttt attttttgcc tcaatgattt tattaaattt   67620
ccgcgaagga ctagaaaatt catctcgggt attagacggt cgcacaactt tgcttttaat   67680
gacatccatg tgtacggcag ctcacgccac gcaagcagca cttaacatac aagaaggcct   67740
ggcatactta aatccttcaa aacacatgtt tacaatacca aacgtataca gtccttgtat   67800
gggttccctt cgtacagacc tcacggaaga gattcatgtt atgaatctcc tgtcggcaat   67860
accaacacgc ccaggactta acgaggtatt gcatacccaa ctagacgaat ctgaaatatt   67920
cgacgcggca tttaaaacca tgatgatttt taccacatgg actgccaaag atttgcatat   67980
actccacacc catgtaccag aagtatttac gtgtcaagat gcagccgcgc gtaacggaga   68040
atatgtgctc attcttccag ctgtccaggg acacagttat gtgattacac gaaacaaacc   68100
tcaaaggggt ttggtatatt ccctggcaga tgtggatgta tataacccca tatccgttgt   68160
ttatttaagc agggatactt gcgtgtctga acatggtgtc atagagacgg tcgcactgcc   68220
ccatccggac aatttaaaag aatgtttgta ttgcggaagt gtttttctta ggtatctaac   68280
cacgggggcg attatggata taattattat tgacagcaaa gatacagaac gacaactagc   68340
cgctatggga aactccacaa ttccacccct caatccagac atgcacgggg atgactctaa   68400
ggctgtgttg ttgtttccaa acggaactgt ggtaacgctt ctaggattcg aacgacgaca   68460
agccatacga atgtcgggac aataccttgg ggcctcttta ggaggggcgt ttctggcggt   68520
agtggggttt ggtattatcg gatggatgtt atgtggaaat tcccgccttc gagaatataa   68580
taaaatacct ctgacataaa aaacatgtat aataaaaagt cactataaac gtattctcta   68640
caatacttta ttcgcgaata atacacacta cctttgggtt tttttcccgt ccccaaatgg   68700
tgtttggtgc actctaccaa aaaatagagc gcctaaatat gctatataac gcctcccagc   68760
aaaatacggt tcaaaggcat tacccgatat tgtattgtag tacagggcaa tgggaattga   68820
tgatcccaat aaacggcata gacgcacagc gccgttatag cagggtctc cagagtacag   68880 ggtatctaag taccgggata tctcatactc atgcctttcc gtgacagaaa catcaaccgg   68940
aacagtatcc gataaaccaa ctcctgtttt tgcaaggcgt aaaattcgca caccttcctt   69000
ttttgcaaga tgtgacgttt ccttgtaaca gggaagctgg gggagtggta agaacaacaa   69060
agtttcagcc aacgtgccaa taaagcccac ttccctcaag aggctgtttg ctgtatccac   69120
aatggtccgt attaaatctt gagcaacttg atccgtgtca tcatcactgg gtaacgcgtt   69180
aacataacta cgcgttaaat cttcaataac ggcataacaa ttaaacgctt cccaccgaga   69240
cagtatatat tgaacaatca cgaaccgttg acaggacgtc agatcacgtc cgtaagcatg   69300
cccgaaaaat ggaagttccc cccgttcgcc atataccgca acaactgcag tatatatcgt   69360
ctcacgggct tcattaagtt catcttcaag tccaggccat tttctggctt taaatataac   69420
ctcgtccgca aaaaaaaccg cacatgataa cgcgcggata caatgagtag tggctttatg   69480
gcgaggatcc caaatgtcca ttacccgggg atggtccta atctgtacaa agttacttag   69540
tgtaatatga tcggacttct tacgccgtct aggctgtttc tcagaatacg gttcacccga   69600
aatcggcaca tcatctgctt ttacgtcttc cgtaaccaca tcagcagcgc gccgactaac   69660
aattatactt gttttttcat cgtcgttact tccgttaagc gcgtctcgta tctcgggcgt   69720
```

```
cccgtcgaat aatccactca ctagctcctg caaactttct ggtaactcca acatacgcat   69780
atacaccaat gaaaaactgg cttcgtttgg tacgtacata aagccatttg tggtattaat   69840
ggcggtgggt gttggaaaca attttagctt attctcgcgc gtaacatcta cccccgccac   69900
caatgttaaa tgcgtcacgg ggagggacac gagataatct gcgagcgtag ggtcctccac   69960
ttcaacatca aatgttccgc aaaggtcgcg atccaccgcc cccgatcccg ctgcaagtaa   70020
ggccactcga tccaaaaaca cgcagttatt attggatgat accgcccatg tcttcccggt   70080
gcgattgagc tcacttcgaa cgtaactggc aacagatctg tcaccgggtc cgaccccgcg   70140
aacaacatgt ccaaattttg cgatctcgcc tccatgtttg cggggtatgg aaattaagca   70200
tcccccgcat ataaaatacg ccctggtagc acgtcgtta aaataaaacg ttacgccgtt   70260
ataagatacg gttgaatgat atggaaattc catattaaag cgtttatcgg aacattaacc   70320
tcgaacttgc cgtcccgtga tcgtgtgatc gccaacctta ggtccacacc gaatatgaga   70380
aatatataac tacacgcaaa cattcaaaac accgtggtat cattaacgtc atatgaaaag   70440
atccaatcaa tccaatcaac cacacctcct accgtttagc acgtcagcta tgtgacatgc   70500
tccaaacata cgtaaacatt tagagagggt gttataacag tctgtcaggc ggggtatatt   70560
ctacataata caaggatcgg ctttaacttt gtcaacattt ttactttgga ctataaactg   70620
cgactgaacg ttatgaaccc accccaagcc cgcgtctcgg aacagacaaa ggacttgctt   70680
agcgttatgg ttaaccagca ccccgaagag gacgcaaaag tgtgtaaatc cagtgataat   70740
tcaccgcttt ataacaccat ggttatgtta tcgtatgggg gtgatacgga cttactatta   70800
agctctgcat gtacccgcac atctaccgta aacaggtcgg cgtttacgca acactccgtg   70860
ttttatatta tatccacggt gttgattcaa ccaatatgtt gtatcttctt tttttttac   70920
tataaagcga cacgctgtat gctcttattc acagccgggt tacttctgac gattctacat   70980
cactttcgac ttattattat gttattgtgt gtctacagaa atatacgatc agacctgcta   71040
cccttatcta catcccagca actgctgctt ggaattattg ttgtgactcg aacaatgcta   71100
ttttgtatta cggcgtatta tactcttttt atagacaccc gggtgttctt tttgattacc   71160
ggacacttgc aaagtgaggt tattttttcca gatagcgttt caaaaatact tcctgtgtcg   71220
tggggtccaa gtccagccgt gttactggta atggcggcag ttatttacgc tatggactgt   71280
ttggtggaca cggtatcctt tattgggcca agggtgtggg tccgtgttat gttaaaaaca   71340
tctatttcgt tttagtccat ttcaataaat gtactataat tgttcagtct aaaaataatg   71400
ttgggtattt ataattaccg ccccgtgtt acttggaaac acccatacat atgttccact   71460
ctacatcaaa cttctcgcag ttttcttgtt cccgcacacg tttacacgtc cggattcaag   71520
tcgcaacgct gctgacaaaa tgacaacggt ttcatgtccc gctaacgtga ttactacaac   71580
ggaatctgat cgtattgctg ggttatttaa catcccagcg gggatcattc caactggaaa   71640
tgtgctgtca accatagagg tgtgtgcaca ccgttgcatt tttgattttt ttaaacaaat   71700
acgatcagat gataacagcc tttactcggc tcaattcgat attcttttgg ggacatactg   71760
caatacatta aactttgtgc gttttctaga acttggactg tctgtcgctt gcatctgtac   71820
taaatttccg gagctggctt acgtgcgaga tggcgttatt caatttgagg tacaacaacc   71880
catgatagca cgtgatggcc cacatcccgt cgatcagcct gttcataatt atatggttaa   71940
gcggatacac aagcgttcgt taagcgctgc gtttgcaatt gcatcggaag cgttgagttt   72000
gttaagtaac acatatgtcg atgggacaga gattgactca tcgttacgta taagagctat   72060
ccaacagatg gctcgtaatt tacgcaccgt tttggactca tttgaacgag gcactgccga   72120
```

-continued

```
tcaacttctt ggtgttctat tggagaaagc cccaccgcta tcgctgcttt caccaattaa    72180
taaattccaa cccgagggac atctaaatcg tgttgcacgc gcggccctac tttcggacct    72240
caaacgtaga gtctgtgcgg atatgttttt tatgacccga cacgccaggg aacctaggct    72300
gatctctgcg tatctgtcgg atatggtttc gtgcacccaa ccatcggtga tggtatcacg    72360
aataactcat acaaacactc gcggacggca ggttgacggt gtgttggtaa caacagcaac    72420
cttaaaacgg caactattac agggaatttt acaaattgac gacaccgccg ctgacgtacc    72480
agtaacatat ggcgaaatgg ttctacaggg acaaacttg gtaaccgccc ttgtgatggg    72540
aaaggccgtc cgcggaatgg atgatgtagc ccgccatctc cttgatataa ccgaccctaa    72600
cacgttaaac ataccgtcta tacccccaca atccaactcc gattcaacga cagctgggct    72660
tccggttaac gcccgtgttc ctgcggattt agtgattgtt ggggataaac ttgtattctt    72720
agaagcatta gaacggcggg tctaccaagc tacgcgcgtt gcctaccctc ttattggaaa    72780
tatagatatt acgtttatca tgccaatggg agtgtttcag gcaaactcca tggacagata    72840
tacacgacac gccggcgatt tttcaactgt atccgaacag gatccacgtc aatttccacc    72900
ccaagggatt tttttttata ataaagatgg gatattaaca cagttgactc ttcgtgatgc    72960
aatgggtacc atctgccaca gttcattgct tgatgtcgag gccacacttg ttgccctccg    73020
ccaacaacat ttagatcgtc agtgttattt tggtgtatac gtggccgagg gtacagagga    73080
cacattggat gttcaaatgg ggaggtttat ggaaacgtgg gcagatatga tgcctcatca    73140
ccctcattgg gtaaacgaac atttaacaat tctacagttt atagctccga gcaacccgcg    73200
tctaaggttt gaattaaacc ccgccttga ttttttttgtt gcaccggggg acgtagacct    73260
tcccggaccg cagcgtcccc cggaagccat gccaaccgtt aacgcaacat tacggattat    73320
caacggaaac attcccgtgc ctctatgtcc catttcattt cgagactgtc gcggaaccca    73380
actcggtttg ggaagacata caatgacccc ggcaaccatt aaagccgtaa aggatacatt    73440
tgaagaccgc gcatacccaa ctattttcta catgctagag gctgttattc atggaaacga    73500
aagaaacttc tgtgcgttac tgcgactgtt aacacagtgt attcgcgggt attgggagca    73560
atcccacagg gtggcatttg taaataactt tcacatgtta atgtacataa ctacatatct    73620
cggaaacggt gagcttcccg aagtctgtat taatatatat cgggatttac tgcagcatgt    73680
aagagcatta cgccaaacta taccgattt tacaatacaa ggagagggcc ataacggcga    73740
gacctcggaa gcgctaaata acatccttac ggatgacacg tttattgcac ctattctatg    73800
ggattgtgat gcgttaatat accgtgatga agccgcccga gaccgactcc ccgcaattcg    73860
tgtaagcggg cgaaacggat accaagccct tcactttgtg gatatggccg gcataacctt    73920
ccaacgacgc gataatgtgt taatccacgg gagacccgtt cggggagaca cgggtcaggg    73980
tattcccatt actccacacc atgaccgtga atggggtatt ctctccaaga tttactacta    74040
tattgtcatt cctgcatttt cccgcggttc ctgttgtaca atgggcgtgc gttatgatcg    74100
cctataccct gcgttacagg cagttatcgt tccggaaatt cccgctgatg aagaagcccc    74160
aactacccca gaagatccaa gacaccctct tcacgcacac caactcgttc gaactctct    74220 taacgtttac ttccataatg cacacctaac cgttgatggt gatgcattgc tcacactaca    74280
agagttaatg ggagatatgg ctgaacgaac gacggccatt ttagtatcaa gcgcccccga    74340
tgcgggagcc gccacggcaa caaccagaaa tatgagaata tatgacggag cgctttacca    74400
tggccttatt atgatggcat atcaggcgta cgatgaaacc attgcaacgg gtactttttt    74460
```

-continued

```
ttatcccgtt ccggtcaacc ctctgtttgc atgtccggaa catttggcat cattgcgtgg    74520
aatgacaaat gctaggcggg ttttggcaaa aatggtacca ccaatccctc ctttttctggg   74580 agccaaccac cacgcaacta tacgccaacc cgttgcctac catgtaacgc atagtaagtc    74640
ggattttaat actcttacat attctcttct tggagggtat tttaagttta caccaatatc    74700
tcttacacat caactacgaa cgggatttca ccccgggatt gcctttaccg tagtgcgcca    74760
ggatcgcttt gccacagagc aacttttata tgccgagcgt gcttctgaat cgtactttgt    74820
cggacaaatc caagtacacc atcatgatgc tattgggggg gtaaacttta ccctaaccca    74880
acccagagct cacgtggacc tgggagtcgg gtatacagct gtatgtgcca cagcagccct    74940
gcgatgccct ctcacggata tgggcaatac tgcccaaaat cttttttttt cacgaggagg    75000
agtgccaatg ttacatgata acgttaccga atcgttgcgt cgtataacag catcgggggg    75060
tcgcttaaat cccaccgaac ccctacccat cttcggcgga ctacgtcctg ctacatcggc    75120
aggaattgca cgagggcaag cctctgtgtg tgagtttgtg gccatgccgg tgtccactga    75180
cctacaatat tttagaactg catgcaatcc tagaggtcga gcatctggaa tgttatatat    75240
gggtgaccgt gacgccgaca tagaggctat aatgtttgat cacacacaat cggatgttgc    75300
ttatacagat cgagcaactc ttaacccatg ggcatcacaa aaacattcat acggtgacag    75360
gctatacaac ggaacataca accttacagg cgcttctcct atctacagcc catgctttaa    75420
gttttttaca ccagcggagg ttaacactaa ttgtaataca ctggatcggc ttctaatgga    75480
ggcaaaggct gtggcgtcgc aaagctccac cgacactgaa tatcaattta aacgccctcc    75540
cggttctacc gaaatgacac aggatccgtg tggcctttttt caagaagcat atccaccact    75600
atgctcaagc gatgcggcca tgttacgaac ggctcacgcg ggagaaaccg gggcagatga    75660
agttcactta gcccaatatc tgattcgaga cgcgtcgccc cttagggggat gtcttcctct    75720 tccgcgataa tttcaccacg cccacatacc cactcccaat aaaagccctg tagagcgcat    75780
tggcatctta cttgagattt ggatacgctc ggccgacttg gtctgtttca cgcttcctta    75840
aacaacatgg ctatgccatt tgagatagag gtattgttac caggagaact atccccggcg    75900
gaaacatctg cattacagaa atgtgaggga aaaattatta ccttctcaac cctgcgtcat    75960
cgagcttcac tggtggatat agcgctgtcg tcatattaca ttaacggtgc tccaccagac    76020
acgctctcgc tgttagaggc ataccgaatg cgattcgcgg cagttataac acgggtcatc    76080
ccgggaaagt tgttggcgca tgccattggc gtgggtactc ctacacccgg gttgtttatt    76140
caaaatacat ccccgttga tctttgtaat ggcgattaca tctgcttact tcctccggtt     76200
ttcgggtccg cagactcaat tcgcttggac tctgtaggac tggaaattgt tttcccttta    76260
accatccccc agaccttaat gcgagaaatc atcgccaaag tggttgcacg ggccgttgag    76320
cgcacggccg cgggtgctca aattttaccc cacgaagttc tacgaggcgc ggatgtcatt    76380
tgttacaatg gaaggcgtta tgaactcgaa acaaatttac aacatcggga cggatcggat    76440
gcggctattc gcacattggt tttaaatcta atgttttcca taaacgaggg atgtctgctt    76500
ttattggcgc tgattccaac tttgttagtc caaggagcac acgacggtta tgtaaattta    76560
ttgatacaaa cggccaattg cgttagagaa accggccagt taattaatat accgccaatg    76620
ccgcggattc aagacggcca tcgccgattt cccatatatg aaactatttc atcttggata    76680
tcaacatcat ctagactggg ggataccttg ggaactcgcg caattttacg cgtctgtgtg    76740
tttgatggac cctctactgt tcatccggga gaccgcacgg ccgtgattca agtgtaaaca    76800
ggtgttaata aaaacacaac cagtctagtt acatttcacg cgtcttgttt ttatttaata    76860
```

```
ggcataaaca cggaatccgg tatacatgaa ctgccaatat acacggacat aattaatgca   76920
accatcagat catctgacat tgttcccgtg gtaccttttac ccgtgtaagt ttttgtgtct   76980
agattaccca taccgccttt aattacctct gtcaggttat ccaactgttt acatagatac   77040 tccacgggt ctacacctaa ctttactgtt agggatacaa gctcctgtga ggctattata   77100
tttccggagt taaatcgttt aacaaaatag tctacggccg cgttttttg ttttgtaat    77160 aaaaaaaaag gtacgccac gctacatccg ggaggtatgg aatgataaaa cagtaacact   77220
ggagcggaag atagcacgtt tcccttttcg aggacagcaa actgttgtgc tatagccaac   77280
gatatggcaa ctgcagaatc ctggctgctg tttccctcta tagaaacgtg tacgtttgta   77340
aatgtattgg ggtgtaaagc gagtatgtgg cctaagcatt gagtaacgca acgccctatc   77400
tcactggaag acgtgccagt taaagctcta agaaaaaagt gctccaatcc aaatataatc   77460
caatccgact tataacgacc aacaatcgct acaccagtac cagacgctcg tgtatttgag   77520
gtaaatgcag ggtctacgta aacgtacaac actgacgata atatagcaca attcgcaacg   77580
gttgacggcc gatataaaat aaacctctca cgggcagttt ttgtaaataa tggccggtca   77640
aaccccacac ccccagaatt ctgtttacgc ccacctacaa tttcctgcac gaaggagtcg   77700
gccataaata aatctgcagt gcgccgcatg gctccatcca ttgtgatgaa aaccggctta   77760
tttaatacat aacacgaaca agctgtgaca tcgctatgtg ctaaaacacg cggcatgtga   77820
tcgtcgcata catatgtaac aacgtttaac aactgatccg acgatccacg taagttatac   77880
aaaaaacttg tacttgcttt tccggtattt gttgatgaaa caaaaataat tttacaattg   77940
gtttgattta aaaatccgac tatagtttgt acagcatcag gtcgaataaa attagcttca   78000
tccacaaaca gaagattaaa atcttgacct cggatacct ggaacgatag aaagatatat    78060
agttacccca ccaaagttta aatgtatcct taaataccac gtacgtaaaa aatgtttgaa   78120
tacgtacata tttctttttt ttttccagta caaccatatc cggtgtataa tggaagccca   78180
tttggcaaat gaaccaaac atgcactttg gcataatgat cacacaaaag gattactaca   78240
cgttgtgata cctaacgcgg ggcttattgc ggccggaata gatcccgcat tactgatttt   78300
aaagaaaccc ggacaacgct tcaaggttga agtacaaaca agatatcatg ctacaggtca   78360
atgcgaaccg tggtgtcaag ttttcgccgc gtacattccc gataacgcct taacaaatct   78420
cttaatacca aaaacggaac catttgtttc acacgttttt tcggccacgc ataattcagg   78480
gggattgatt ttatcattgc ctgtttatct tagccccggt ttattctttg atgcatttaa   78540
cgttgtagcg atacgaataa atactggaaa ccgcaagcac cgtgatattt gtattatgta   78600
tgcagaacta atcccaaacg gaacgcgtta ttttgctgat ggacaacggg tacttttatt   78660
atgcaaacag ctgattgcgt atatccgatg caccectcgt cttgcatcgt ctataaaaat   78720
atacgcagag catatggtgg cagccatggg tgaatcacac acgtcaaatg gggacaatat   78780
tggacccgtt tcatccataa tcgatcttga tcgacagtta acttctggag gtattgatga   78840
ctcccctgct gaaacacgca tacaggaaaa taatcgggac gtccttgagc taataaaacg   78900
ggccgtaaac attgttaact ccaggcaccc cgtccgacct tctagttccc gcgttgcatc   78960
tgggttgctt caaagtgcaa agggccacgg agcgcaaact tccaacacag atccgatcaa   79020
taacggttcc tttgatggcg tccttgagcc gcctggacaa gggcgattta cgggaaagaa   79080
aaacaattcg tccgccagca tcccacccttt acaagacgtt ctattgttta ccccagcttc   79140
gacagaaccc caaagtctta tggaatggtt cgacatctgt tatgcccaat tagttagcgg   79200
```

```
ggacactcca gcagatttct ggaaacggcg tccoctatca attgtaccgc gacattacgc   79260
agaatccccc agtccgttga ttgtagtatc ttacaacgga tcctctgcct ggggaggacg   79320
tattaccgga agtccaattt tatatcactc tgcacaggct attattgatg ctgcgtgtat   79380
aaatgcccgg gttgacaatc cccaaagcct acatgtgaca gctcgccaag agctagtcgc   79440
gcgtttaccg ttttggcta acgtcctaaa taatcaaacc cccttacccg cctttaaacc    79500
aggcgccgaa atgttttaa accaggtatt taaacaagcg tgtgtgacat cgctaaccca    79560
aggtcttata acggagttac aaacgaaccc gactctacaa caactcatgg aatatgatat   79620
tgcagattct tcccaaacgg ttattgatga aattgtagcc cgcacaccag acctgattca   79680
gactatagtt tcggtgttaa cggaaatgtc aatggatgcg tttataaca gctccttgat    79740
gtatgcggtt ttggcgtatc tgtcatctgt atatacacga ccacaaggtg gggggtatat   79800
accctacctt cacgcttcct tcccatgctg gttaggtaat cgttctatat atttatttga   79860
ctattataat tcaggagggg aaatacttaa gctttccaag gtccccgttc ccgtagcctt   79920
agaaaaggtt ggtattggta attccacaca actgagggt aaatttatac gcagcgcgga    79980
tattgttgat attggaattt gttctaagta tttacccggt caatgttacg cgtacatttg   80040
tctaggattt aaccagcaat tacaatccat tttagtttta ccgggggat ttgcggcatg    80100
ttttgtatt accgataccc tacaggcagc actacctgca tcgttaatcg gacctattct    80160
agacagattc tgcttctcta ttcccaaccc ccataaataa attagtgtca ctataaaac    80220
ataacaccag aatctcttca tatgtaattt tacgtcattt ctcccgtttc cacccctct    80280
taaaatataa aataaccggg tgggtggcat taaacccaca agtacccggg cggcaatccg   80340
ctagactgtt tttctgctca tggaattaca acgcatattt ccgctgtaca ccgctacggg   80400
tgcagcgcgc aaattaaccc ccgaggcagt tcagagactc tgcgatgcat taacgctgga   80460
tatgggatta tggaagtcca tcctgaccga tccccgggtg aaaataatgc gatcaactgc   80520
ttttataact ttaaggatcg ctccgtttat ccccttcaa acggatacta ctaatattgc    80580
cgttgttgta gccacaattt acatcacgcg cccacgtcag atgaacttac ctccgaagac   80640
ttttcatgta attgtaaatt ttaattacga ggtctcgtac gcaatgacgg cgactttaag   80700
aatttatccg gttgaaaaca tagaccatgt ttttggagca acgtttaaga acccgatcgc   80760
gtacccccctt ccaacatcta ttccggatcc tcgagcagat cccaccccg cagatcttac    80820
accaacgcca aacttaagca actacttaca accccgcgg cttccgaaaa atccatacgc    80880
atgtaaagtt atttctccgg gagtgtggtg gtcagacgaa cgaaggcgtt tatatgtact   80940
ggctatggaa cctaatttaa tagggctatg tcccgccgga tggcatgctc ggatacttgg   81000
ctctgtatta aatcgactcc tcagccatgc ggacggatgt gatgaatgta atcatagagt   81060
tcacgtgggg gcactgtatg cgttacccca tgtcacaaat catgcggaag gttgtgtgtg   81120
ttgggctccg tgtatgtgga gaaaggccgg tcagcgggaa ttaaaagtgg aggtagacat   81180
tggcgccacg caggttcttt ttgtagatgt caccacctgc attcgaatta cgagtactaa   81240
aaatcctcgc attaccgcaa atcttggcga cgttatagcg ggaaccaacg ccagtggtct   81300
ctctgtacca gtaaattcat ctgggtggca gctttatatg tttggagaaa cattaagccg   81360
ggctattatt aacggctgtg gtctgcttca gcgaatttgc ttccccgaga cacaaagatt   81420
atcgggtgaa ccggaaccta caaccaccta gtatacctta actcaaccgc cgttgtggaa   81480
aggtatatgt caacatttac agtaatatat taaaggttaa atttataaaa cactcacgtt   81540
tgtgttgtga cttgacgcga acaccgctgt gctgtaagac ccgtcggtaa atgaaaacgt   81600
```

```
aatagattcg ccttttacat gatccacgta atttgcccca aaccactgtt ccaggcgaga    81660
cttgataccc tcaaacacgg gttccgttgc tttgcgtata tgagccgtat aacccacttt    81720
aattcctcta aacgtggcca ttactaaagc tattaatggt acaagaaacc atgttttccc    81780
atgtctacgt ggtaccaaaa acacagttga tttttgtttg aagtgttcta aaacactgtc    81840
agaaacactt ggcgtgttaa acactgtacg cagaaagcag tcaactctgt cggcatgatc    81900
gcccaatagc accgatgaaa taaaatgcgt ggtgtgcatg aggatcattt tttgaaacag    81960
ttccaacgtc cccttatatc tgccatagat tggaacgtca acctttgcgc gtttgccatg    82020
acttccacac tcttcaatac tctcaaaaga tgtttccaca aggtacgaaa accgttgtgt    82080
aaaggtagac aactgacaga aactatccga cagagaaaac gcgcgaaatg tgttcataac    82140
accgctatac gcatttcgat gaggtgctgc ttcttccggt gaatattcat aaaactgtac    82200
actactgaca gccttttta attcagggct tacgtttgca tttaccgaat atcgccatgg    82260
tttcaaaact acattggggg tacagttgta ccctgttgac gatagaaacg cgccaaacat    82320
tgcccgtcga gcagtagccg agaacagtgg aatatattca caacagttgt gaagcgttcc    82380
aattccggga ataacggcct gatgacgtcg ggttacatct atagcaaaat tcagaaacgg    82440 gatttggggtt gcgtttccca gagacccttg ccgcgtggaa cacggggtag gggactccaa    82500
cgtcccaaag cgttcatccc tacgacgctt tagacgttca aaatatctta cagattcttc    82560
accaagcgta cgaccaaaca ttatcaatga catttaacat caattcacgg aatccgcctc    82620
atctcttgta agcagtaaaa caggaagccg cgtcatctta cgtactcgtt acgtatatat    82680
cataaacatt tcagggccg cattcattca ctttggtcat gtcaggccac actccaacct    82740
acgcttctca taggcgtaac cgtgtcaaac tagttgaggc gcataaccgc gcggggttat    82800
ttaaagaacg gaccctcgat ctaatccgtg ggggtgcgag tgtacaagat ccagcatttg    82860
tgtatgcctt tactgctgca aaagaggcct gcgccgattt aaataaccag ctccgctctg    82920
cagctcgcat agcttcagtt gaacagaaga ttcgtgatat acaatccaag gttgaggaac    82980
aaacaagtat tcaacagatt ttaaatacaa acagacgcta tatagcaccc gattttattc    83040
gcggtttgga taaaacagaa gacgataata ccgataatat agacagactg gaagacgcgg    83100
taggaccgaa catcgaacac gaaaatcata cttggtttgg agaagacgac gaagcgttac    83160
ttacacaatg gatgctgacg acacaccccc caacctccaa atatctccaa ctgcaggacc    83220
tttgcgttcc caccacaata ccgacggaca tgaaccaaat gcaaccgcag ccgatcagca    83280
agaacgagaa tccaccaacc ccacacacgg atgtgtaaat catccatggg ccaatccgtc    83340
aactgcaaca tgcatggaat caccagaacg atcacaacag acaagcttat ttttattaaa    83400
gcacggctta acgagagatc caatacatca acgcgaaagg gtggacgttt ttccacaatt    83460
taacaaaccc ccatgggttt ttagaatttc caaattatcc cgtttaattg tacccatctt    83520
cacgctcaat gaacagttat gttttctaa attacagatt cgagatagac ccaggtttgc    83580
gggacgggga acgtatgggc gtgttcatat atacccatcg tcaaaaatag ctgtaaaaac    83640
catggacagt cgtgttttta atagagagtt aattaacgcg attttagcga gtgagggttc    83700
tatacgagca ggggaaaggc taggtatttc tagcatagtt tgccttttag gttttcgtt    83760 acaaaccaaa cagctactgt ttccggcata cgacatggat atggatgaat acattgttcg    83820
cctgtccaga cggttgacaa tacctgatca catagacaga aaaattgccc atgtattttt    83880
agatttggct caagcgttga cgttttaaa tcgaacgtgc ggcctgaccc acctagatgt    83940
```

```
gaaatgtggc aatattttc ttaacgtcga caactttgcc tcgttggaaa taaccacagc   84000
agtaatcgga gactatagcc tagtaacatt aaatacgtat tcccttttgta ctcgagcgat   84060 atttgaagtt ggaaatccat cccacccgga gcacgtacta cgcgtacccc gggatgcatc   84120
gcagatgtca tttcgtttgg tgttgagtca tggaacaaac caacccctg aaatcttgct    84180 tgattatatt aatggaacgg ccttactaa atatactgga accttgcccc aaagagttgg    84240
acttgcgatt gatctttatg cattgggcca agcactctta gaagttatcc tgctaggacg   84300
tcttcccgga caactgccca tttcagtaca tcggaccccg cattatcact actacggtca   84360
taagttatca ccagatttgg cgcttgatac gctggcatat cgatgtgtcc tggcgccata   84420
tatactccca tctgacatcc ccggggactt aaattataat ccctttatac acgccggaga   84480
gctgaacacc cgtatttccc ggaattcttt acgccggata ttccagtgtc acgcagtgcg   84540
ttacggcgta acgcactcaa agcttttcga aggcatacgc attccggcct cattatacc c  84600 agccactgtt gttacatcgt tgttgtgtca cgataattca gaaatacgct cggatcaccc   84660
tttattatgg cacgatcggg attggatagg atcgacataa gccccagcc agccaaaaaa    84720 attgcccgtg tgggaggtct acagcaccct tttgtaaaaa cggatattaa cacgattaac   84780
gttgaacacc attttataga cacgctacag aagacatcac cgaacatgga ctgtcgcggg   84840
atgacagcgg gtattttat tcgtttatcc cacatgtata aaattctaac aactctggag    84900
tctccaaatg atgtaaccta cacaacaccc ggttctacca acgcactgtt ctttaagacg   84960
tccacacagc ctcaggagcc gcgtccggaa gagttagcat ccaaattaac ccaagacgac   85020
attaaacgta ttctattaac aatagaatcg gagactcgtg gtcagggcga caatgccatt   85080
tggacactac tcagacgaaa tttaatcacc gcatcaactc ttaaatggag tgtatctgga   85140
cccgtcattc cacctcagtg gttttaccac cataacacta cagacacata cggtgatgcg   85200
gcggcaatgg cgtttggaaa aaccaacgaa ccggcggcac gagcgatagt tgaagcattg   85260
tttatagatc cggctgatat ccgtactcct gatcatttaa cgccagaagc tacaactaag   85320
ttttttaatt ttgacatgct caataccaaa tctccaagtc tccttgtggg tacaccaaga   85380
atcggaacgt atgaatgtgg acttttaatc gacgttcgaa cgggacttat aggcgcgtcg   85440
ttggacgttc ttgtatgtga cagggaccct ttaactggca ccctaaatcc ccaccctgca   85500
gaaaccgaca tttcattttt tgaaattaaa tgtcgtgcta aatacctctt tgatccagat   85560
gacaaaaata acccgctcgg tcggacgtac accacgttaa taaatagacc tacaatggca   85620
aatctacggg acttttata ctctataaaa accaccatgtg taagcttctt tggaccctca   85680
gcaaacccaa gtacacgcga ggccttaata acggatcacg ttgaatggaa acgtttagga   85740
tttaaaggtg ggagggcct tacagaactc gacgcccatc atttgggcct caatcggaca   85800
atctcatccc gagtgtgggt atttaatgat ccggacatac aaaagggac aattacaacc    85860 attgcatggg ccactggaga tacggctctt caaattcctg tatttgccaa tccgcggcac   85920
gctaacttta aacaaattgc cgtacaaacc tatgtattat ccggttactt tccagcgcta   85980
aaactacggc ccttccttgt caccttata ggacgtgtgc gccgaccaca cgaggtggga    86040
gtcccattgc gcgtcgatac acaagcggct gccatttacg aatataactg gccgactatc   86100
ccaccccact gtgcggttcc ggttatagcc gttctaacgc ctatcgaagt tgatgtgcct   86160
agagtgacac aaatacttaa agacacagga acaacgcga ttcatcagc attgcggtca     86220 ttgcgatggg acaatcttca tccagcggtc gaggaggaat ctgtggattg tgcaaacggt   86280
acaacgagct tgttacgtgc aacggagaaa ccgttgcttt gaactcagag ttctttgaag   86340
```

```
actttgactt tgatgagaat gtaacagagg acgccgataa atccacacaa cgccgccac    86400 gagtgatcga tgtaacacca aaacgaaaac cttcgggaaa gagctcccat tccaaatgcg    86460
caaaatgtta aaccctgata aaccctgata aacgttctaa taaaaacatc aaatcatggt    86520
tggttactgt gaatgtttgt tttattgctt ggggtttac aagtacaacc cacgctactc     86580
ccacccactg tttgatcgct cgtataacag ctcatcctcg cggtccgttt catatgttga    86640
gtcattttca tagacgtagc cgtagccttg tgatgggtaa tttgtgcggc gagaatttct    86700
atgtgcaggt tttactttc gtatgtatcc ccgtacccgc tcgggtactc ttcttacggc     86760
accgtagaac cgactgcgtt tctgtcgatg atacacatat gcacgcatca atctgagaag    86820
caacatgaca acgaaaaaca cggccaggca agccaaggtt ccccgagttg tgggaattaa    86880
ccgtggagat tgaaccgata tagggtcata taatcggtcc atatacgagt gcgcggcggt    86940
tcccaacgta gcacaggcca cgagcgttcc cagggacggt cctattaaca cgtgtatata    87000
atgcgccaaa attaattctg atactataag atatacaact gacaatgtac taaatgtaga    87060
catggccacg acaccgatg accacagtcc cgtatgtaga tgattcgcca ccacaagttc     87120
cagcattaat gatacaaata ggatacatat cgccatcaac gcagccatca aattcacgaa    87180
cactgcgcgc gtaggccccg caaggcgata taaaagacg ctctgctgtc gtaaatttgc     87240
gaccgctttt atgttcgttt cgtccaattt tccgcgtcca caaaatacg ttgtaaatat     87300 tacacttgtc gcaaaatgtc caagatataa tgtagcagcc acgccgattt gcttgtaagc    87360
taataataac acaacggcgt ttaataacca caatgacaaa agaccccaaa aaagtgttgt    87420
gggatctaca actaaccatg caacaccgga gctttgccgg acgttgat ttttcgtttc      87480 tcggtgtata atcgcggccg tgatcagtgt atataccgcc atggccattg ccgttaaagc    87540
cgtgtagtaa gtaaatgcca caacgctatg tggttccaaa aacaaaaccg gggcgctgta    87600
tccacctcta tttccggacc ataccccccc atctagggtg gcgttaaata actcataatc    87660
aactacggca gcataaaaac aagggatccc ggtatattca gaagaggcgg caattaacgt    87720
agccaggagc attaccgcac ccaaagtgaa catcatcacc tgaattatcc aaattcgcca    87780
attaagcgta tccatttgat gatctaacgc ttccacctcg ggtgtcgtgg tgtcgtacgg    87840
cgagactttt tcagaacgcg gcccttctt ttgagttccc atgtctccca acaccgggga     87900
gagcaacgcc gccgtctatg cgtccagtac acagctcgcg cgggcgttat atggaggggga   87960 tctggttttcg tggattaaac acacccaccc gggaattagc ctggaactgc aattggatgt    88020
tccagtaaaa ctaataaaac ctggtatgtc acaaactcgc ccggtaaccg tcgtacgtgc    88080
ccctatgggc tctggtaaaa caacagcctt gcttgagtgg cttcaacacg cgttaaaggc    88140
agatattagc gtactggttg tctcatgtcg ccgtagcttt acccagacgt tgattcaacg    88200
gtttaacgat gcaggcctct ccggattcgt aacatatttg acatccgaga catatattat    88260
gggttttaaa cgtttgattg tgcaacttga aagcctacac cgcgtatcca gcgaagctat    88320
cgacagctac gacgtattaa tactggatga ggtaatgtca gtgattggac aattatactc    88380
ccccacaatg agacgtcttt ccgcggttga tagcctatta tatcgtcttt taaatcgctg    88440
ttctcaaatt atcgcgatgg atgctacagt aaactcgcag tttattgatt taatctccgg    88500
attgcgtgga gatgaaaaca tacacacaat tgtgtgtaca tacgcgggag ttgggttctc    88560
cggaagaact tgcacgatcc tgcgtgatat gggcatcgac acgcttgtgc gagtcattaa    88620
acgatctcct gaacacgagg atgtacgtac catacaccaa ctacgtggaa cattttttga    88680
```

```
cgaactagca ctacgattac aatgtgggca taacatctgt atattttcat caactttatc  88740
gttttcggag ctagttgctc agttttgtgc aatatttaca gactctattc ttattttaaa  88800
ctcaactcgg cccctatgta atgtaaacga atggaaacat tttcgcgtgt tggtgtacac  88860
taccgtcgtg accgttggat tgagttttga catggctcat tttcatagca tgtttgctta  88920
cataaagcca atgtcatatg gccggatat ggtatcggtc taccagtcat tagggcgtgt   88980
acgtttattg ctacttaatg aagttttgat gtacgtcgat ggctcaagga ccagatgcgg  89040
acccctgttc tcgccaatgt tactaaactt taccatcgca aataaatttc aatggtttcc  89100
tacacacacc caaataacta acaaactgtg ctgtgcattt aggcaacgat gtgcaaatgc  89160
atttacacgc tcgaacaccc atctcttctc aagatttaaa tacaaacacc ttttcgagag  89220
atgctctctt tggagtttag ccgatagcat taatatctta caaactcttt tggcctctaa  89280
ccaaattttg gttgtattgg atggcatggg tccataacg gacgtttccc cagttcaatt   89340
ttgtgcattt atacacgatc tcagacatag cgctaacgcc gtagcttcct gtatgcgttc  89400
tcttagacag gacaatgaca gctgcttgac cgattttggc ccttccggat ttatggccga  89460
taacattacc gcgtttatgg aaaagtatct tatggagtca attaataccg aagaacaaat  89520
taaagtattt aaagcccttg catgtccaat agaacagcct agactagtca atacggcaat  89580
attggggggcg tgtatacgaa tacctgaagc gttggaagca tttgacgtat ttcaaaaaat  89640
atacacgcac tacgcttccg gttggttttcc cgtcctggac aaaacggggg aatttagcat  89700
cgcgactata actaccgccc caaatttaac cacacattgg gagctgtttc gccgttgtgc  89760
ctatattgca aaaacactca agtggaatcc gtccaccgaa ggctgtgtaa cacaagtttt  89820
ggatacggac attaatacac ttttcaatca acacggggat tcgctggctc aactaatatt  89880
tgaggttatg cgctgtaacg ttactgacgc taagattata ttaaaccgcc cggtttggcg  89940
aacaaccgga ttcttagatg gatgccataa tcaatgcttc cgtccaatcc ctacaaaaca  90000
cgaatataac attgctctat ttcgtttaat ttgggaacaa ttatttggcg cccgcgtaac  90060
taaaagtacc cagaccttc cgggaagtac tcgtgtgaaa aacctaaaaa aaaaagatct   90120
agaaactta cttgattcaa ttaacgtgga tcgttctgca tgtcgtacct accgccagtt    90180
gtataacctg cttatgagcc agcgccattc gttctctcaa cagcgttaca aaattactgc  90240
ccccgcttgg gcacgccacg tgtatttca agcacatcaa atgcacttgg ccccgcatgc    90300
cgaagccatg ctacaattag cgctatcgga actgtccccg ggatcgtggc cgcggataaa  90360
cggggcggta aattttgaaa gtttataacc cgttaatacc atatatggac atccataggg  90420
ggggttacat aaatactaag cctctgtaca acacaaaggg cctctaacaa tgcactgaac  90480
cacaaccaag ctatggacgc aacgcagatt accttggtta gagaaagcgg acacatttgt  90540
gccgcaagca tatacacatc ctggacacag tccggacaat taacacagaa cggtctttcc  90600
gtgttatact acttattatg caaaaactca tgtgggaaat acgtccctaa gtttgccgaa  90660
attaccgtac aacaagagga tttatgtcgc tactccaggc atggggggag tgtttctgcg  90720
gcaacgtttg cgtctatctg cagggcggcg tcctcggctg cgttagacgc ctggcccctt   90780
gaaccactgg gtaacgcaga cacctggcgt tgtctccatg gcactgccct ggccacttta  90840
cggcgcgtat tagggtttaa atcgttttat tcgccagtaa cattcgagac tgatacgaat  90900
acaggtcttc tgttaaaaac aatcccgat gaacacgcgt tgaataatga caacacgcca   90960
tctaccggag tattgagggc taattttccc gtggccattg atgtttcagc agtcagcgca  91020
tgtaacgccc acacgcaagg tacgtcgcta gcctacgccc gcctgaccgc acttaaatct  91080
```

```
aacggtgaca cccagcaaca acacccttta gacgtggagg taattacacc aaaggcctac   91140
atacgtcgga aatataagtc tacgttttcc ccccctatag agcgggaagg ccaaacctcc   91200
gatttgttta accttgaaga acgccgcttg gttcttagtg gcaatcgcgc aattgtggta   91260
agggtactct taccgtgtta ttttgactgt ttaacaacgg attccaccgt tacatcttcc   91320 cttttcaatat tagcaacata tagactgtgg tacgcggcgg cgtttggaaa acccgggggtt  91380 gtccgtccaa tctttgcgta tttaggcccg gaactcaatc cgaagggtga agacagagac   91440
tacttttgta ctgtcggatt tcccggatgg accactcttc ggacacaaac tccagccgtc   91500
gaatctattc gcacggctac ggagatgtac atggaaacgg atgggttgtg ccagtaacc    91560 ggtattcagg cctttcatta tctagccccc tggggacagc atccccccctt acctccgcgg   91620 gtgcaggatc ttattgggca aatccctcaa gatactggac atgcagatgc aactgtcaat   91680
tgggacgcgg gccggatatc taccgtcttc aaacagcctg tacaactaca agatcgttgg   91740
atggcaaagt ttgatttcag cgcctttttt cccacgatat actgcgctat gttccccatg   91800
cattttagat taggcaaaat cgtcctggct agaatgcgtc gaggaatggg gtgcctaaaa   91860
cccgcgttgg tgtctttttt tgggggggtta cggcacatac tcccgagtat atacaaagct   91920
attattttta tagccaatga aattagcctt tgcgtcgaac aaacggcctt ggaacagggc    91980
tttgctatat gtacttatat aaaagatgga ttttgggaa tcttcaccga tttacatacg    92040
cgcaatgtat gttcagatca ggcacgttgt tcggccttaa atttagcggc cacctgcgaa   92100
agagcagtca cgggcttatt acgaattcaa ctaggtctta actttacacc cgccatggaa   92160
ccggtactcc gggtcgaggg tgtgtacact cacgcattta cctggtgtac cacgggaagc   92220
tggctgtgga atttacaaac aaacacgcct ccggatttag ttggcgtgcc atggcgaagt    92280
caggcggcgc gagatttaaa ggagcgtctt tcaggactcc tatgtaccgc aacaaaaatt   92340
cgagaacgga tacaggaaaa ttgcatatgg gaccatgtcc tatacgacat atgggccgga   92400
caagttgtgg aggctgccag aaaaacatac gtcgatttt ttgaacatgt ttttgatcgc    92460
cgttatactc cggtatactg gagtcttcag gagcaaaatt cggaaacaaa agcaataccg   92520
gcatcttatc tgacatacgg acacatgcaa gataaggatt ataaaccaag acagataatt   92580
atggttcgta atcccaaccc acatggacct cctactgttg tttactggga attgctacca    92640
tcgtgtgcct gtattccccc catagactgc gctgctcatc tcaagcccct tatacacacg   92700
tttgtcacta ttattaacca tcttctagat gctcataatg attttttcaag tccatcattg   92760 aaatttactg acgatcccct tgcttcatat aacttcttgt ttttatgaca aaaaacacg    92820 ccgcaacaac ccatccttaa aataaaaggt ttatttactt tacaacccgt ggtgaatttt    92880
tatacgtttc aaataactga acattttcg gtgttaccat ggtgcgattt aaccaccaaa     92940
aatatacgct cttctgatat tccgaatctc gtaaaggtcc atttaacaat cccgggggta    93000
cttgcaccac accatctgga caggggggg ttccgtgggg caggtcaaaa cgctgaccca    93060
ccccacatga atatatagcc tttataatat tgggggccgt tccaggctga gggttcagta    93120
acttaacaaa catataatgc ggcaatacgc gggtttttgt aaagggggttg ttatcaacga  93180 catacattag agtgtttaac aaccataaaa ctccctcata taaaaaccga cgcatttttt   93240
ccaaaggtcc tatttgacac tcaacgcgtc taagatatac agacaattgt acaaacagcg   93300
atggagatgc cccggagggc ccaatgcctt ccagatacat taaaataaca cataaggtaa   93360
aatctaggac attatccggg cggaatagag tcatccgata gattaacagg cgcggaggca   93420
```

```
cccccaccgt atacacccta tcttcaaccg cagttaatac ggaaaaaata aatccgcgga    93480
acgctggttg agtaacacac tccatgtagt aacgatcaca ggacacctca cttgaatcac    93540
cattcaacac tactaaaacg gtctcttggt gttccggttt tacgcgcagt gatacaacag    93600
agtttgccaa aaagcgtggc ttcaaaccgg ttacctcccg cgcctcgcat acgaatcttg    93660
gtattgcttg tattctaaga tcttcgatca cgtcgctcac atccaacccc tcttcggctc    93720
gtgttagtaa gttgtcgatc gttacgctgc aacctaaaat gctgggtata tttattccgg    93780
acatcccatc ggccatcccc cgcctccgg tttgctcgaa ttttatccag taaggtcgaa    93840
tccgctgcat ttaccttgtg tacccgtaac ctctcagggg ggtgtccttt cataaaatgg    93900
gataggtttt tatatccaac atgcatgtat tggttattta ttttattggg ttccgggatt    93960
ctttcgtcat cttctgtagg gtcaggcaaa ccccaggaag gacttggtgt tctccgtggg    94020
ccccgtttta ttacctctgc gcgaacctgc atttcatata atattcggat ttgggataaa    94080
taggactctg ttctcgcctt tttaaaaata gcctggcata actcttcctc tgacctatgt    94140
acctcgcttt gagttaccaa gaatcctaat cgggtggccc gtaatatgaa tgaaaaatac    94200
ggcgcaacta gtaatgagat tgacgcattt gaatatgata cagaaatttc ctggccttga    94260
ttattgttta cccggtgaag cttaaaacag cgaacaagtt cctgtttcca tagctcagac    94320
aaacgtttta tatcatctcc ataagggggg atataacgag attgaaaact attggcaata    94380
tatgcatcat ccctattat gccggtaaga tctataacct cgtgatttaa atcggcaata    94440
cgtgtttctt ctgccattgt aatatgtgac cctttagatg gctttatttt taccctctct    94500
tcccgtaacc gtttcagctc tccttctttg aactggagcc tttcggtcag atcgctgttc    94560
acatccttga gaccctcaat ggttttgaat aaattattca cataaccctc gagcatgccg    94620
ttgatactgt taaccaccga agttttaaac gcactttgaa cgtttgttgt tccggacatt    94680 gccccccgt taaaggattg gttggccttg ccaaaccccg gttgtgatgt gtccaccgat    94740
ccacttcctt ccagaatgtg attgcccgtt tcttctagat aggaacgtac ggtttcggta    94800
atatctccaa catgtctcat gttttttaag ttaactatta gctttacaag tctagacgcg    94860
gccgatccag cccgtgttgt atcgttctcg cccattatac gatcaaccgc acgtgtgctg    94920
tgagatctat catcttcatt ccggcgacct attaacacgc gcaagggc tgtatttaaa    94980 acttggcaga cgcgagcatg ttcacgtaat gcataacagg ccaacacctc cccagaaagc    95040
cgctgtaagg gtgagtcaaa tactacaccc tccccacata caacgggcgg ccacacgacc    95100
aaacactctc ccttcatgcc cgttacatca tcctttgcca taattaatct tcggttataa    95160
ttataataaa gacgcgtcct atcataatcc ataatagcaa cattttgcat acactcaact    95220
aggcttgtga caaccgccgc tcctctggcc aacgttgcat cggcaacttt taacatctgg    95280
gacagttctg ccgcttgacc catatacgta tttaatggtg cagggttcc attctgttct    95340 gatcgtacct ttcttacaac gggcacaata cctacacagg ctatccagtc cacgtatttg    95400
gcaaaaccga cccttccatt taaaccactg gtatagagac aaccggttat tccacgcaga    95460
aactcaagta acgatgactg taatgtttga cgccaggttt caaaaacctg atgtgcaagc    95520
cgtacggctt ctgattctcc acatagccca taacgttccg ctagagcccc ggcatgcagg    95580
ttacattgtt ggatgtggtg ttcccaatct gctgctaggt cctcataccg agttgcatcc    95640
aacgcgttca tcaaaacggt tgcctgaact tggcgaatta cagtttccgt agaccgtaca    95700
gcgctatata tgccttgtcc atcggtatat ccaaagtcac cggctaggat ttttcgaaac    95760
aacatacttt gcgtggttgg gtgtattaac atccagccat cttcctccgg aaatgtacaa    95820
```

-continued

```
aaccctatat ccggggcgta ctcattccag tatatatcga acatgttctt gtattggtca   95880
tttgggttac ttccattcaa gccctggtca atagaaacag aacttgctat ccttttttct   95940
tcactaccgg aactgttatt aaaaagagac gttatttcgg ccattgaaaa ccacgatgaa   96000
aagatcaatt tctgtagaca gttcttcacc caaaaacgtt tttaatccag agacgcccaa   96060
tggatttgat gacagtgtat atttaaactt cacctctatg catagcattc aacctatcct   96120
ctcacggatt cgagaacttg ccgcaattac gattccaaaa gaacgtgttc cgcggttgtg   96180
ttggtttaaa cagttactcg aactgcaagc gcctcctgaa atgcagagga atgagctccc   96240
cttctccgtt tatttaatta gcggaaatgc cggctccgga aaaagcacgt gtatccaaac   96300
gcttaacgaa gctatcgatt gcattattac cggatccacc agggttgctg cccaaaatgt   96360
tcatgctaag ttatcaacgg cttatgcgag tcgtccgata aacacaatct ttcatgaatt   96420
tggttttcgc ggaaatcaca ttcaggctca gctgggccgt tacgcatata actgactac    96480 gaccccccct tctattgagg acctgcaaaa aagagatatt gtatactact gggaagtttt   96540
aattgatata acaaaacgag tgtttcaaat ggggacgac ggtcgcggag gaacatcgac     96600
atttaaaacc ctgtgggcaa ttgaacgttt gcttaataaa cctacaggct caatgtccgg   96660
aaccgcgttt atcgcatgcg gttcccttcc ggcttttacc cggagcaacg ttattgttat   96720
tgatgaagca ggattgctag ggcgtcatat tctcacggcc gttgtttact gttggtggct   96780
tttgaatgct atatatcaaa gccctcagta cataaacggt cgaaaaccgg tcatagtatg   96840
cgtcggttcg cccacccaaa ctgactcgtt agaatctcat tttcaacatg acatgcagcg   96900
ttcacacgta actcctagtg aaaatatact cacgtatata atctgcaatc aaactctgcg   96960
tcaatatact aacatctcac ataactgggc aatctttatt aataacaaac gatgtcaaga   97020
ggacgatttt ggaaatcttt taaaaacgct tgagtacggg ctacctatta ccgaagcaca   97080
tgcgcgtctg gtcgatacat ttgttgtacc tgcatcctat attaacaatc ctgctaatct   97140
tcccggatgg acgcgtctgt attcgtcgca taaggaggtg agcgcgtata tgagtaagtt   97200
acacgcgcat ttaaaactat cgaaaaatga ccatttttct gtgtttgcct taccgactta   97260
tacattcatc cggctaacgg catttgatga ataccgcaaa ttaacgggac aacccggact   97320
ttctgttgaa cattggatac gggcaaactc cggtcgtttg cacaattatt cccaaagccg   97380
agatcatgac atgggaacag ttaaatacga aacacattca aatcgcgact taattgtagc   97440
ccgtacagac atcacttacg tgctaaatag tctcgtagtt gtaaccacaa gactacgtaa   97500
gttagttatt ggattcagtg gtacatttca atcgtttgca aaggttttac gtgacgactc   97560 cttttgtgaag gctcgaggag agacatccat cgaatatgct taccggtttc tgtcaaacct   97620
aatctttgga ggcttgatta acttttacaa tttttttgtta aataaaaacc tacatcccga   97680
taaggtatcg ttagcataca aacggttagc tgccttaacc ctggagttat tgtctggaac   97740
aaacaaagcc cccttacacg aagcagcggt taatgggcg ggtgccggga ttgactgtga    97800
tggtgcagct acttctgccg ataaagcctt ctgctttacc aaagcccccg agtccaaagt   97860
aacggcctcc atacccgaag acccggatga tgtaattttt acggcactta acgacgaggt   97920
tattgacttg gtatactgcc agtacgaatt ttcctatccc aaatcatcca atgaggtcca   97980
tgctcagttt ctgttaatga aagctattta cgatggtcga tatgccatat tagcagagct   98040
tttcgaaagc agctttacaa ccgcccccctt tagcgcgtat gtcgataatg ttaatttcaa   98100
cggaagcgag cttttgatcg gcaatgtgcg gggggggctg ttatctttgg cattacaaac   98160
```

```
agatacgtat acccttttgg ggtatacttt tgcacccgtg ccagtctttg tagaggaact   98220
gacccgaaaa aagctgtacc gcgaaactac cgaaatgtta tatgctctac acgtacctct   98280
tatggtctta caggatcaac atgggtttgt gtccatcgta aacgctaacg tatgtgaatt   98340
taccgagtct atagaggatg cagaattggc aatggccacc acggtggact atggccttag   98400
ttctaaacta gccatgacaa ttgcacgctc acagggtctg agtttagaga aggtagctat   98460
ctgttttacg gcggataaac tgcgcctaaa tagtgtgtat gttgccatgt cgcgtacggt   98520
ctcctctagg ttcttaaaaa tgaatctaaa ccctctacgg gaacgatatg aaaaatccgc   98580
agaaattagc gatcacattc ttgccgctct acgtgatccc aacgtacacg ttgtgtatta   98640
aagcattgta taaaaacacg catgcgggct tgctgttctc atttctaggt tttgtcttaa   98700
atacacccgc catgagcatc tctggacccc caacgacgtt tattttatat aggttacatg   98760
gggttaggcg ggttcttcac tggactttac cggatcatga acaaacactc tacgcattta   98820
cgggtgggtc aagatcaatg gcggtgaaga cggacgctcg atgtgataca atgagcggtg   98880
gtatgatcgt ccttcaacac acccatacag tgaccctgct aaccatagac tgttctactg   98940
acttttcatc atacgcattt acgcaccggg atttccactt acaggacaaa ccccacgcaa   99000
catttgcgat gccgtttatg tcctgggtcg gttctgaccc aacatctcag ctgtacagta   99060
atgtgggggg ggtactatcc gtaataacgg aagatgacct atccatgtgt atctcaattg   99120
ttatatacgg tttacgggta aacagacctg acgatcagac cacaccaaca ccaacccccgc  99180 accagtatac atcgcaaagg cggcagcctg aaaccaactg tccttcttca ccacaacgg    99240 ccttttcac atcagacgac gacgttcttt cgttaatatt acgggacgcc gcaaacgcgt    99300
aaagacagat tcaagactaa catttatccc aactgattac atttcatacg cgaataaacg   99360
acacaaaaaa tttatattta acggctttta atttgaagac acctatcctc ttaacgttga   99420
tgagccttgc aggttgggtg ccgcgcttca ccggtattat acataaccga tttaccgtgt   99480
ttacggcagt ctgaccattt accagtgtat gtctgtaata cgacgttgtt gtgtcccgac   99540
aaaattaact cgcgtacaaa tttctgatgt tcccccggcg tggcaacgct ggcatttcca   99600
aacacattac gttctcgtac gtccatgacc gctattttca gtattaattg gttggtcggt   99660
caaagtattt tccttatgta aaaggacacg atctaaagcc gtaaactcat acacaaacac   99720
tggtaccaac ggacgcgatt ttccgtccgt tgagcgggtg taatatcggc gaggtcttct   99780
tgcacgaata ctctcgtaca gtaggtttct gacacggggt gcatgggttt tttgacacaa   99840
cacaaacatt tgcaggctct tatgactgga tggattgaat ttattttag atagggtcac    99900 gtgttttgt cgtgacacgc ctcgaccaga aaaggctgcg gttttcgtac acgcgaccgt   99960
tatttcacag gcgttcataa ccaagctgcg gcggatggtg tcggttaatt gtctccgccc  100020
aagttcgtca atagatgata ccatgaacaa cgtatcaaat ggtacatagt cgtctttggt  100080
tttctcaata cagcccgcgt gcccaatcgg aaattttca tttgcatcaa cgctatttc    100140 tgtaaaatcg ttctgaacac tgtgttggct ggctacctgt ttaaaatttg ggatcgaaca  100200
cggtccacga tgcaatcccc aacccccattg aagcaatgcc gtcggtacgg aaggaggcaa  100260
ctccgaaaac attatggtac gcaagagggt cgattggagt gttatataac actccaatcg  100320
atctcgggtt cgcctttacg cgtaaaatac tcattggctt gaacgaaatg tcgacaattc  100380
cgaaatggaa cacgggacaa tggcgacgga tgcgcgtgtg ttagcaccag atgacatctt  100440
gaattcggtt ggggttgtctt ctgtgcatgc gcaccccaca gcataaaaac taaccctgta  100500
cggttctcgc ataacctctg tagcacgcgt tgcaccagcc gccccagcc taagtataca   100560
```

```
tgcgacccccg gagtcccgcg acgaaccgta agcgtggtat tcagcaataa caccccctgc 100620
cttgcccaac tctccaggca tccgtgagtg ggcggagtca tatttgggta tgattccatg 100680
agggccgcaa aaatattttt aagactagac ggtggtgtta tgccacgttt tacactaaac 100740
gctagcccat gtgcatgtcc cgcggtaggg tatggatctt gaccaataat tacaacgcga 100800
atgctctggg gtccgcaaaa tcgcgtccat gcaaaaatat cgcctgtaga tggaagtatt 100860
tcttcccctg aatttaaaag acgattgtat tctaaaaaaa tacctttcgc gtacggctct 100920
ttaagttcgt ccgacaacag gtcataccac tcagggaaa tgttaaactt gctgaaaact 100980
tcaaccgaat ccagttgcga agagacgggg gtgaacgttt ccgtgtcgta atgatgtgac 101040
atgttattta acttgaaggt tgggggtct agcttaaccc ccaaaggcag cccgcggggt 101100
cgcttgcggg ttttttttggt aaccggatgg gccaaaacat aaatgtcctt tgaatccgat 101160
agtttcattt cattggcata cgcgttggaa caaacggtcg gctccccaga cacatccatt 101220
ttccgggata tttgtggaag atggagtaga gtctacccat acaccggaaa gggcatccaa 101280
caaagcatcg cgtatgtccc cgcttttatg ttcttcacca acagattgtg ccagcccctt 101340
taaggtgacg tatggatttg tccagtacgc catttgtttg tctttaaacc aaagtataac 101400
ttccggtact ggacattttg tcttaaccac gattcccgat agcgcctcgc tgaggtttga 101460
taccgggggt gccgcatagt cccacgcctc atataccgat gacacgcacg gttccgttat 101520
aatcaaactc acatccgata gcggtttggc tccaaaaaac aacggagtgt cgtcttggag 101580
atgaagacaa tacgcgattg tgatagtttt taaaaaaact atctgcagta accatttatg 101640
tgatgccatg acgcttgtgt tttcccttca ctacgacgtt gtcgtatcct ttgaaaaact 101700
tgaccactct aatggaagca tggacaagta tgagttttat atatacagtt ggcctttagt 101760
taaactcttg gtgtcatatc tcattttcct aaaaagggcg atcttaatat gtcaaacgtc 101820
acggcgtgcc gacaaagcga atttccatgc aagatttgga tgtagtattt atacacccaa 101880
tcacatgtca cgtattaagc tttacagtcc cccgttatct gatataatca cttttcttaa 101940
cacgtcatcg ggaaaacaga tgtttatatt ataccttcg cggtcattta cggcaaatac 102000
ttagaccgtt ttcaagcgga ctgaaaacgc tcaaattgcc ttttggaggc ctgcccaacg 102060
gccattatcc cttggatcta agattgattt gcggtaacgt ttgccaatca agctttaaaa 102120 acgtaccccca aacttaaaac gctcaaattg ccttttggag gcctgcccaa cggccattat 102180
cccttggatc tgagattgat ttacggtaac gtttgccaaa cccacgcatt tcagtttaaa 102240
tatttctaag cattcttagt gcgtacttgg cagcgtgctt aaaatatcaa ccaatatcca 102300
ttatgctaca cgtttccttc tatccgtttc aatccattaa aagtccatta acaaaaatga 102360
tgcatcatac ctaattcacc taaaaacctg actcattgca gcagcgtttc ctccttgcag 102420
actatccagt tggcattta acgggtccg gctgcctaaa ccgaaaacac cgttgccttt 102480
actgtaagta caaaactaaa atttatattt gcgtgcgtat tttgtaacat atatgccttt 102540
tatccccccg caagtttgct ttaccctcgc cttcaccacc ccgcccacct tccggccatt 102600
ttaataactt taattgctat aagacatacc caaaccggat gattttttgcc gctggaaaaa 102660 cagcttctaa ttttcccgtc tcaactcggc cttggttgca tctccaagta tacctttagt 102720
ttgctcccgt agaggtgtat aaatacaaac ggtgacaagt attgagcgta atctcaaatt 102780
tttgtaattt agggcggagc gcttacgaca gcacatgcgt actgttagac tgttatgttt 102840
attgtatttg cagagcagga tgccccggtt actccgagac cggattgcgg gcattccgaa 102900
```

```
tcgtgtacgg acttaccagg gggcagtatt tacaccttgg gttccagata taccaaccct 102960
tacgaccaat agcaacactc aggtattttt aaaatgcacg tttaatgatc ataatttaca 103020
tacagttggt aataaagcag actgtggatg tttaaggcat ttccttcccc ctcccaacaa 103080
actaggactt cttcatcttg tttggaatac ctttacccgc tttaccggca gagctttttt 103140
tggtaaggtg tttcagtgaa cctgatgttg atccggaggt ggaggggta ttggactccc 103200 cctgtggaga ggcaactttg cgggttttac ttcccttaca tgccgaatca gactcagatg 103260
tcaggtctat tgttaagcat cgtttaacgt ctctgccggt atgaaataaa cggcgcttag 103320
caccccttgc gcttcccggt ttaatcccc gtaacacaga aaaaagcctg acttttggg 103380 gtgtatttac caatcgggta tccctttcat cgccacgaga ggtctcccg gttgaggtgg 103440 tttctggtct tacaattgga cctgtaatta gttggatggc tgtatctttc caggtccagg 103500
tttgcatggt taggcgggtt ggatcggtac atcgatccaa caagaataac atgtttgtta 103560
caaacggtcc tgttgaatca tgcaaaagac aacgcaggga tgttttaat cccgcctcat 103620 cacgcccgta aatacctata tagtttaata tcaacatttt tgtaggctct acaatttcgg 103680
gttgatacag ttccgcaagt tgatcatcaa gccatccgag taaaggttgc atgtaacacg 103740
ggaatctcgc gtttccctct gttcctctat ccgtggctcg aaaaggcagt ctgtccatgg 103800
ttcgtgggtc ttgattaatt cccacagata ctggacgatc acggtagtcc tgccccccgg 103860
tccggggttg ctgtgcagat tcaatcgagc catacaccac cggggtcgcc gatcgaacag 103920
caggttggtc tttaaaaaat accttccgta aaaatgatgc ggtagagcat gttttggtta 103980
caccagggct cgagtctcgg gtcggtggtt gtatagaatc ctgttgagag tcacttggtg 104040
actctgctgt gggctctcta gccgacgatt gaaggggccc agggtttggt gattgaatgg 104100
gctcccgact cgatcttgat gttggctgtt ggatggactc ccgactcggt cctgggcttg 104160
gtggcagaag atctatgaca tctcccggta ggatgtcgat ggaatcttca aatgacggct 104220
cagaaaaacc atcgtcgtcg gatgggtgca cttcatattc cttgtaactt gtatcactta 104280
cgatcttatg caggatggat tgcactggac accggcagag aggacactgg acgctggtgg 104340
aggtccatgc ccgaatacaa acaaagcaga agtcgtgcaa acacggcatg gttttttccga 104400 gatcggaaac ggtgctcatg catatggtgc aggtattatc cgaagcgtcg gaggtgccgc 104460
taccgcccgc taatatggta tccatggtaa caactggctg tattctaatg tccgggcatc 104520
caaacacgta gcagaactgc catgcgttct aaattgtgag ttgtggcgag tacattttta 104580
taattggtac caacgaagac acaccccctat atccctccac ccatttcttt taagtcccac 104640
ccactaaaac gtgggtataa aatgtgtatt ggggtaggcg gacagtccca acaaacaggg 104700
aagttgattg gtataacctt gggccgggta tacagctaag tgacatttta gattctgtct 104760
ttatttagat aaagagcgat acgaagacat ttctccaccc ccctgtaata cccgtaaata 104820
aaggtaagtc cacaaacaaa agcactgtat ataggaagtc gggtgtattg ggacagttac 104880
tccattagag gcgtacaaac aatactggga tagggtaatg caagtccccc ccgatggtcg 104940
ccccgcaaac gcgcggggag gtgggtcgc ttttttttt ctctctcgag ggggccgcga 105000
gagggctggc ctcctctccc ggggtccgcc gggcgcccag aaaccggggg ggggttattt 105060
tcgggggggg gtccgaccag cccgcccgtc gcccgcccgc acagacagac agacactttt 105120
ttcataaaaa ccgttccgct tttattaaca acaaacagtc cgcgcgccag tggcgctcac 105180
gagaaaagga ggggactccg tcaccccga ctctgcgggg ggctcctccc ccgcgccct 105240 ccccacacat cgtcctcgtc ctcggaggac gaggacgagg acaacagctc caccttgacc 105300
```

```
gccgggcgca aacccacccg gcggtctcgc agcacacccg gggccaccga cacgatgctc  105360
accccaaagg atgaccccgg tgcgtccccg tcgtccccgc cccctcctc gctgtcccac   105420
gcgtcttcac accccacctc ccaatcgtcc agctccaaag cgtgttctct gtcgtctgcg  105480
gtgcgccgct gtcgcccgc ctgggtttct gacggccgtt ccgagccccc gtggtgtccg   105540
aacacgaacc gtgttccgtc gctcccctcc aacaccgtct ccgcggcccc aaaaccgggc  105600
ggccacatta ctctgggaat cgggggagg gcattccgag cctcgtccgc cgacgcatac   105660
agcgccaccg accgaccggc cacgggtgga agcacgagtg gttctgcggc agggtcgggt   105720
tccagcaggg cgtggcggca aacacccctc gcccaggtgg gtacgtcgcc ggcctccggc   105780
ccggcggccc ccggtctccg tccctcggga aggaagacgg gtcgaagcgc ggcacccagg   105840
ccccatcggt ttgctgcgcg gtggctatgt gccgcctcgt ccacaaagtc ggctgccccg   105900
agccccagac cccgagactg tcgcgcgagg tccttgcaac cgtcaaaacc cggcagcacg   105960
tactgccggt attcacgggg cgacagggg acgcgggtct tggggcccgc gcgggtacac     106020
acggtgtatg cgacgttccc accgcggcac aaacacaggg gttgttcgcc cgggtacagg   106080
ttggcaaacg cagtctcgat acgagcaaaa ctcgctggcc caaggtgcg cgacgatgca    106140
aacacggccc gggcgagtcc ttctgtgacc gccgagtctg gccatcggac gacggcctgg   106200
gcgtccggtc gcgccggggc ccggacgtac acgtgatact gagacaaagc gggtccatcc   106260
ctgggccacc tctcgagggc caccgcgtcc aacaccagca accggcgccg ggcagaggcc   106320
aaccgcgagc ctagatactc gacggccccg gcaaaggcca ggtctcgggt cgacagtaat   106380
aaaacgcccc gggcgttcaa agcggacacg tccggcgggc cggtccagtt ccggcccag    106440
gcatgagtgc tcggcaggca caaccggtta ctcagggctg ccaggaccac agacagtccc   106500
cctcgggatg gactccatga cggtcccgga tctgtcgcga gggtgctctc gagggggccg   106560
ttgatgtcct ctccgggcaa cggatcgtag atgatcagaa gcctcacatc ctccgggtct   106620
gggatctgcc gcatccaggc gcacctccgt cgcagcgcct ccactccgct gggtggacca   106680
aaccgtcggt ctcctccgcc cggacgccga gcggcgattt ccgccaaggc gccgggatca   106740
aagcttagcg cagggcgcca ggccgtggga acaatgggt cgtcgaccag acgggcgatg    106800
gtttcggggg tacagtacgc cttgcgagcc tggtccgacg ggaccggggt atgcagggcc   106860
ccccggggaa tacgccgaaa tccccgtttt ggggccggtc cgtcaagtgg catcgttatt   106920
acggcggggg gatccaccac agggcccgag gtgatggtca cgggctcgga tacccgcctc   106980
ttggccttgg aaaccacatg atcgtctgca acccgggcgt ccgcgacggg tgtctccta    107040
atcttgtcga ggaggcttct gctctcgact ggctgggact tgcgcttgcg cggagttcgt   107100
aaacgatcat ccggtggaca cacagaaaga gagcgtgcgg cggccgacgg ctgagggtcg   107160
ggagcctgtg tggccgggt tgttggagaa gggtgaccgc gggagatccg cgccgccgga    107220
ctggagcccg ttgcctcggg gtatgccatg ctggcaaagg ctctgcggag actctgtagg   107280
ataaagtgtt tttgggcccg gtcgtatcga cggctcatag ccacgccgc ggccgcgtgg    107340
gggagagccc agagggcctc ccccgtggcc atggcttcgc ctacatgcgg aacgggagac   107400
gctacgctcc ccgtaacggc ggtacccgcc cgtcccggtg caacagctt ttggtagaac    107460
tggttcaggg ccgagttgac accggtcagc ttggggttct ggagccatgc tataggggtct 107520
ctgtctggac agtagatcag gttaatcagc gcgcggtact gtctagccgg atctcccaac  107580
tccggcacgt aaagcggcac gggttccgtt gaggcctcgt aacgagcccg cgccgctctc  107640
```

```
acagcctcat cctcccagtg accctctctg gtctccccgg acgtccaaa ccgcaccctg   107700 ttggatggga ggggtgccga tccgggccaa gggcttccgt cgggcatcat gagcggcccc   107760
gacaccgggg gaattatcgg ggttctggat cgcggcaggg aaaatgattt ctgtctctgg   107820
cgccccggtt cccccgcaag acgtttggtc ttacgaatcc tcggatcggg accgctgatg   107880
gatcgatatc ccggttggat attttgtttc gtcgacccac catcatttga gtccgaatca   107940
tccgaatttg acggggaagg ggcgtgttcg cgtccggacc tgctgcctgt agtttcactt   108000
cccaccgaaa cgcgccgggg ttcatcgtct tcatcctccg atgacgatcc ccacgacgag   108060
gaagaggatg aagacgaaac aaactcacga ctctttggct ttttctccac tgggctgtca   108120
tcctcaatcg ggtctggtgc gtgggatctt cccggcaggg ccaaaaacgc tctaggtttg   108180
ccccccgacg aacgtccagg acgcgaggt gttataccc gggcatcatg tttccttggg    108240
cgggtatcat cggtctcaaa cggcaggtcc gcctttgccc ccttagcggg aacgctgtcc   108300
gaaaggacgt ggtacaattg ctcaaccggg ccgggtacag gtccaccggg tttccgcgcc   108360
gggagtggga ccttaacctt caaagtcttt ttcttcgggc tctttccctg agcgggccgt   108420
tgagttttct ggagaactac tccgtccccc gatgcatgcg catgacccgc ttgctcatcg   108480
cccggctttt tacccgagat ggactgagtt tgtctgtctc gatggaccac cgacggcaaa   108540
cctggtgaat ttcctctcgt cgtttgtcgg ggtatagacc gctggtcttc ccgttgatcg   108600
ttcccggcgg cgtctccaac aggagacgcg ggggatacag gggagaaggc ctgcgggaac   108660
ggaggggtcg tacctctgcc cgtttcccca tcgttcatcg gtggttttgg agacctagca   108720
agcttcgttc cgagagagac tgtctcaagg gagcgatcgg ctcctgttgg ttctcgcgcg   108780
ccggcctccg agaatcgggt gtggaagacc tcggccagcg ggattacagg cgagcccatt   108840
agatcctgac cgtcctcgca tacgtagtcg tcttgtgtta gctcttcgcc aacatcttcc   108900
gttctgggtt ctggttgaag tcccgatacg gagggaattg aaacgatctc gtgttcccgt   108960
cccaccatga ccccgttctc tccaaatagt agatcgtcag gctgactcga ggtgaccacc   109020
cgggccctgt gttcggcggc cgccgcggcc gcgtccaaca ggtccattaa ctccaaagta   109080
tcaggcgacc ccgcgcgttg gggtgtagag cgctgcatcg gcggcgtatc catcgcactg   109140
gggtgaattt agacgtaccc gagttttcca acgctctcg cagccttcaa aggattgcga    109200
ttgcggttgg tgagggagtt ccaacagtac ttaaaacgtg ttgtgccccc cctcgaccg    109260 catatttcct ccccgtgtcg tcaccgtgta aatattctta atgataagac gatgtagtga   109320
ttggacgaga ctcgaggcgg gaagttcatg gaccatagta tgcgtttaag gagagaccgc   109380
tggttggcga tgtacgcccg gtgtctattt ccgcatacct tacaacatca taacaaggga   109440
taccagacat gtgaatttca tttacatatg tttaaataac aaccaatcat cgtgtgtcta   109500
cagacgatat ataatataca taaacacaat tggggttgtc tcacatgcaa aacatcttat   109560
ataacacggg ttgtttccac ccatccggca tctagttaat caaatgcacg tcgacggtgt   109620
gtttgggtcc ctctccgtcg tcattacgtt cgcgcaatca acaagcgtat acaccaccac   109680
ccctcccaac gattatgtca ggcggcacga agcccgcgat aacccataaa atacacacgg   109740
ggttgtggtg ttcacgtaac ccccgccga tggggagggg gcgcggtacc ccgccgatgg    109800 ggaggggcg cggtaccccg ccgatgggga ggggcgcgg taccccgccg atggggaggg    109860
ggcgcggtac cccgccgatg gggaggggc gcggtacccc gccgatgttt ataaccataa   109920
ttctctaaac cgttgtagaa aatcacaaaa aaatttattc aaaaacaagt cgaagaactt   109980
catatctgag gcatgtaaac ccgttcgcac ttcctggggt ggaatggggt gggtgggg    110040
```

```
ggtgaaaaag ggggggggtt aaattgggcg tccgcatgtc tgtggtgtac gccaatcgga   110100
tacactcttt tgatctgcat tcgcacttcc cgttttttca ctgtatgggt tttcatgttt   110160
tggcatgtgt ccaaccaccg ttcgcacttt cttttctatat atatatatat atatatatat   110220
atatatagag aaagagagag agtttcttgt tcgcgcgtgt tcccgcgatg tcgcggtttt   110280 atgggtgtg ggcgggcttt tcacagaata tatatattcc aaatggagcg gcaggctttt   110340
taaaatcgat ttgacgtgat aaaaaaaaac acacggggcc ccccccttttt tttggtgtta   110400 taaaggcaac ccaatcgaag gtctcccgcc ccggaatccc ccattgccat tttacccaag   110460
tagccttatt catagatgta aacgtttggg tgtgtgtttt gttgtgcagg gttcgtccga   110520
ttcataacgc gacagcgtcg agtcggtttt aagggaaaag gttactacgg ccccaaggac   110580
atgttttgca cctcaccggc tacgcggggc gactcgtccg agtcaaaacc cggggcatcg   110640
gttgatgtta acgaaagat ggaatatgga tctgcaccag gaccctgaa cggccgggat   110700 acgtcgcggg gccccggcgc gttttgtact ccgggttggg agatccaccc ggccaggctc   110760
gttgaggaca tcaaccgtgt ttttttatgt attgcacagt cgtcgggacg cgtcacgcga   110820
gattcacgaa gattgcggcg catatgcctc gactttatc taatgggtcg caccagacag   110880
cgtcccacgt tagcgtgctg ggaggaattg ttacagcttc aacccaccca gacgcagtgc   110940
ttacgcgcta ctttaatgga agtgtcccat cgaccccctc gggggggaaga cgggttcatt   111000 gaggcgccga atgttccttt gcataggagc gcactggaat gtgacgtatc tgatgatggt   111060
ggtgaagacg atagcgacga tgatgggtct acgccatcgg atgtaattga atttcgggat   111120
tccgacgcgg aatcatcgga cggggaagac tttatagtgg aagaagaatc agaggagagc   111180
accgattctt gtgaaccaga cggggtaccc ggcgattgtt atcgagacgg ggatgggtgc   111240
aacaccccgt ccccaaagag accccagcgt gccatcgagc gatacgcggg tgcagaaacc   111300
gcggaatata cagccgcgaa agcgctcacc gcgttgggcg aggggggtgt agattggaag   111360
cgacgtcgac acgaagcccc gcgccggcat gatataccgc ccccccatgg cgtgtagtct   111420
ttataaataa atacaatggt ttggctcgtg tcttttttttg atgtctgtct gtgggggagt   111480
ggggtgttgt ggatattaga gggtagaggg tgctggtttg aacgtctcca ttaacccacg   111540
gggtccccac acgggccgtg tggtatgaat ctctgcggat cccgcggtga gcacccgggc   111600
ggtgaatatg ccggacttta ctgcacacga cacgataccc ccgcgcacca ggctctcatg   111660
aacgacgccg aacggtactt cgccgccgcg ctatgcgcca tatctaccga ggcctacgag   111720
gcttttatac acagcccctc cgagagaccg tgcgcgagtt tgtggggag ggcaaaggac   111780 gccttcggac ggatgtgcgg ggagctcgca gcggatagac aacgtccacc ctcggttccg   111840
ccgatccgca gagcggtgtt atcgttatta cgcgagcaat gcatgccgga tccacaatcg   111900
catctggagc tcagcgagcg gctgatattg atggcatatt ggtgctgttt gggacacgcc   111960
ggacttccga ctattggatt gtcgcccgat aataaatgca tccgcgccga attatatgac   112020
cgccccgggg gaatttgtca caggcttttt gacgcgtacc tgggctgcgg gtcccttgga   112080
gtcccaagaa cctacgagag atcctgacac ccatcccttt tatatagaaa aaaaaataa   112140 atttaaaaca tacaccggat aaaagcgtac tgttttttat ttaaatttac acgctcggcg   112200
ttgccccggt tcggtgatca ccgggtctta tctatataca ccgtgtaact cgaaccccg   112260 tgactccctc caatcgcgtt accaaactct tcttccgtat ccgtagattc cgagtcctcg   112320
aaatcgtcca cttatccaac aaattgtgac gttatatatc ccaaggcaaa ggccgctccc   112380
```

```
gtcatagcaa atacaaagac aattattagc gtaatataac agaattttttt acgatgatat    112440 attttatgtt gatattttcc aattcgacgc aaaaattcat ctgccgtttc attttcgcta    112500
tcactataat aacacttttc agccgaacgg ctcggttgta tggctgttat cgttgtatta    112560
tttggttgcg ctcgcggggt taccaccgct tccatcagta aggccacggc ctcaccctcc    112620
atggtgtttt gtccggccat agaaatccag attgtaaggc cagcaggcta gtttaaaagt    112680
gtttaatacc acaccttttg atatttatat acatgcaaga ttctagatta ttcatcaata    112740
ggtcgtttaa agcgcgtttt cataaacgtt gtcagctata ccgacattct cacaaagagg    112800
taaagttacc ttacgttatt attaaataaa acatgtagac attattaata atcctaggaa    112860
caatcaaatc catatttgta agttatgttt aacccctccc cttttttgtca ttatctccgc    112920 cctcttataa tcggatcact ttataagtgt gtcggtgagt atattttgta cagttgttgg    112980
acaacaggtt tttggttcat taacactatc aacataagtc ggggtataca agtataatga    113040
acgacgttga tgcaacagac acctttgttg gacaaggaaa gttccgtggc gccatctcaa    113100
catcaccgtc acatattatg caaacatgtg ggtttataca acagatgttt ccagttgaaa    113160
tgtcgcccgg catagaatct gaggatgatc ccaattatga cgttaacatg gatatacagt    113220
cttttaatat atttgatggt gtacacgaaa ctgaagccga agcctctgtg gcattgtgcg    113280
cagaagcacg cgttggaatt aataaagcgg gatttgtaat attaaaaacg tttacaccag    113340
gggcggaagg ttttgcgttt gcgtgtatgg acagtaaaac atgtgaacat gtggtcatta    113400
aagcgggtca acgtcaagga acggccaccg aggcaaccgt gttaagagcg ttaacccacc    113460
catccgttgt acagcttaaa ggaacgttta cgtataacaa aatgacatgt cttatattac    113520
cacgttaccg aacagattta tactgctatc tagctgcaaa gcgcaacctc cccatatgtg    113580 acatttagc aattcagcga tctgtattac gcgcgttaca gtatcttcat aataacagta    113640
ttattcaccg tgatataaaa tctgaaaata tatttattaa ccacccaggt gatgtttgtg    113700
tgggagactt tggagcagcg tgtttccccg tggatattaa tgccaacagg tattatggct    113760
gggctggaac aatcgccaca aactctcctg agttattggc tagagatcca tatggacctg    113820
ccgtggacat atggagtgcc gggattgtat tatttgaaat ggctacagga cagaactcgt    113880
tatttgaacg agacggttta gatggcaatt gtgacagtga gcgtcaaatt aaacttatta    113940
tacgacgatc tggaactcat cccaatgaat ttcccattaa ccctacatca aatcttcgtc    114000
gacaatacat tggtttggca aaacggtctt ctcgaaaacc cggatccagg ccattgtgga    114060
caaatctata tgagttgcca attgatttgg agtatttgat atgtaagatg ttatcgtttg    114120
acgcacgtca tcgaccatca gcagaggtgt tgcttaacca ctctgttttc caaactcttc    114180
ccgatccata tccaaatcca atggaagttg gagattaaaa ttcattaagc ctgttaataa    114240
aatattgtat aaattgtgtt tataacgtat aacccgttaa ggcaaatagg gtacaaacgc    114300
gcaatgtttt gaaatactaa tataaataac ataaccaata gaaacttaat acagagtcac    114360
gccccattac aacaaggata aaacacggga tcattttctt aacattgtag tagcgctgaa    114420
aagcgtcccc tcccccggct cacagagctg ctcttcggtg tagttgggta tactggtgcg    114480
cctcatttaa tcgcgatgtt tttaatccaa tgtttgatat cggccgttat attttacata    114540
caagtgacca acgctttgat cttcaaggc gaccacgtga gcttgcaagt taacagcagt    114600
ctcacgtcta tccttattcc catgcaaaat gataattata cagagataaa aggacagctt    114660
gtctttattg gagagcaact acctaccggg acaaactata gcggaacact ggaactgtta    114720
tacgcggata cggtggcgtt ttgtttccgg tcagtacaag taataagata cgacggatgt    114780
```

```
ccccggatta gaacgagcgc ttttatttcg tgtaggtaca acattcgtg gcattatggt    114840 aactcaacgg atcggatatc aacagagccg gatgctggtg taatgttgaa aattaccaaa    114900
ccgggaataa atgatgctgg tgtgtatgta cttcttgttc ggttagacca tagcagatcc    114960
accgatggtt tcattcttgg tgtaaatgta tatacagcgg gctcgcatca caacattcac    115020
ggggttatct acacttctcc gtctctacag aatggatatt ctacaagagc ccttttcaa     115080 caagctcgtt tgtgtgattt acccgcgaca cccaaagggt ccggtaccct cctgtttcaa    115140
catatgcttg atcttcgtgc cggtaaatcg ttagaggata accttggtt acatgaggac     115200 gttgttacga cagaaactaa gtccgttgtt aaggagggga tagaaaatca cgtatatcca    115260
acggatatgt ccacgttacc cgaaaagtcc cttaatgatc ctccagaaaa tctacttata    115320
attattccta tagtagcgtc tgtcatgatc ctcaccgcca tggttattgt tattgtaata    115380
agcgttaagc gacgtagaat taaaaaacat ccaatttatc gcccaaatac aaaaacaaga    115440 agggcatac  aaaatgcgac accagaatcc gatgtgatgt tggaggccgc cattgcacaa    115500
ctagcaacga ttcgcgaaga atccccccca cattccgttg taaacccgtt tgttaaatag    115560
aactaattat cccggatttt atattaaata aactatatgc gttttattta gcgttttgat    115620
tacgcgttgt gatatgaggg gaaggattaa gaatctccta actataagtt aacacgccca    115680
catttgggcg gggatgtttt atgaagcctt aaaggccgag ctggtataca cgagagcagt    115740
ccatggtttt agacctcggg cgaattgcgt ggttttaagt gactatattc cgaggtcgc     115800 ctgtaatatg gggacagtta ataaacctgt ggtgggggta ttgatggggt tcggaattat    115860
cacgggaacg ttgcgtataa cgaatccggt cagagcatcc gtcttgcgat acgatgattt    115920
tcacaccgat gaagacaaac tggatacaaa ctccgtatat gagccttact accattcaga    115980
tcatgcggag tcttcatggg taaatcgggg agagtcttcg cgaaaagcgt acgatcataa    116040
ctcaccttat atatggccac gtaatgatta tgatggattt ttagagaacg cacacgaaca    116100
ccatggggtg tataatcagg gccgtggtat cgatagcggg gaacggttaa tgcaacccac    116160
acaaatgtct gcacaggagg atcttgggga cgatacgggc atccacgtta tccctacgtt    116220
aaacggcgat gacagacata aaattgtaaa tgtggaccaa cgtcaatacg gtgacgtgtt    116280
taaaggagat cttaatccaa accccaagg  ccaaagactc attgaggtgt cagtggaaga    116340
aaatcacccg tttactttac gcgcaccgat tcagcggatt tatggagtcc ggtacaccga    116400
gacttggagc ttttttgccgt cattaacctg tacgggagac gcagcgcccg ccatccagca    116460
tatatgttta aaacatacaa catgctttca agacgtggtg gtggatgtgg attgcgcgga    116520
aaatactaaa gaggatcagt tggccgaaat cagttaccgt tttcaaggta agaaggaagc    116580
ggaccaaccg tggattgttg taaacacgag cacactgttt gatgaactcg aattagaccc    116640
ccccgagatt gaaccgggtg tcttgaaagt acttcggaca gaaaaacaat acttgggtgt    116700
gtacatttgg aacatgcgcg gctccgatgg tacgtctacc tacgccacgt ttttggtcac    116760
ctggaaaggg gatgaaaaaa caagaaaccc tacgcccgca gtaactcctc aaccaagagg    116820
ggctgagttt catatgtgga attaccactc gcatgtattt tcagttggtg atacgtttag    116880
cttggcaatg catcttcagt ataagataca tgaagcgcca tttgatttgc tgttagagtg    116940
gttgtatgtc cccatcgatc ctacatgtca accaatgcgg ttatattcta cgtgtttgta    117000
tcatcccaac gcaccccaat gcctctctca tatgaattcc ggttgtacat ttacctcgcc    117060
acatttagcc cagcgtgttg caagcacagt gtatcaaaat tgtgaacatg cagataacta    117120
```

```
caccgcatat tgtctgggaa tatctcatat ggagcctagc tttggtctaa tcttacacga  117180 cggggcacc  acgttaaagt ttgtagatac acccgagagt tgtcgggat  tatacgtttt  117240 tgtggtgtat tttaacgggc atgttgaagc cgtagcatac actgttgtat ccacagtaga  117300
tcattttgta aacgcaattg aagagcgtgg atttccgcca acggccggtc agccaccggc  117360
gactactaaa cccaaggaaa ttaccccccgt aaaccccgga acgtcaccac ttctacgata  117420
tgccgcatgg accggagggc ttgcagcagt agtacttta  tgtctcgtaa tatttttaat   117480
ctgtacggct aaacgaatga gggttaaagc ctatagggta gacaagtccc cgtataacca  117540
aagcatgtat tacgctggcc ttccagtgga cgatttcgag gactcggaat ctacggatac  117600 ggaagaaagag tttggtaacg cgattggagg gagtcacggg ggttcgagtt acacggtgta  117660
tatagataag acccggtgat caccgaaccg gggcaacgcc gagcgtgtaa atttaaataa   117720
aaaacagtac gcttttatcc ggtgtatgtt ttaaatttat tttttttttc tatataaagg  117780
gatggggtgt caggatctct cgtaggttct tgggactcca agggacccgc agcccaggta  117840
cgcgtcaaaa agcctgtgac aaattccccc ggggcggtca tataattcgg cgcggatgca  117900
tttattatcg ggcgacaatc caatagtcgg aagtccggcg tgtcccaaac agcaccaata  117960
tgccatcaat atcagccgct cgctgagctc cagatgcgat tgtggatccg gcatgcattg  118020
ctcgcgtaat aacgataaca ccgctctgcg gatcggcgga accgagggtg gacgttgtct  118080
atccgctgcg agctccccgc acatccgtcc gaaggcgtcc tttgccctcc cccacaaact  118140
cgcgcacggt ctctcggagg ggctgtgtat aaaagcctcg taggcctcgg tagatatggc  118200
gcatagcgcg gcggcgaagt accgttcggc gtcgttcatg agagcctggt gcgcgggggt  118260
atcgtgtcgt gtgcagtaaa gtccggcata ttcaccgccc gggtgctcac cgcgggatcc  118320
gcagagattc ataccacacg gcccgtgtgg ggaccccgtg ggttaatgga gacgttcaaa  118380
ccagcaccct ctaccctcta atatccacaa caccccactc cccacagac  agacatcaaa   118440 aaaagacacg agccaaacca ttgtatttat ttataaagac tacacgccat ggggggggcgg  118500 tatatcatgc cggcgcgggg cttcgtgtcg acgtcgcttc caatctacac cccctcgcc   118560 caacgcggtg agcgcttttcg cggctgtata ttccgcggtt tctgcacccg cgtatcgctc  118620
gatggcacgc tgggtctct  ttggggacgg ggtgttgcac ccatccccgt ctcgataaca   118680
atcgccgggt accccgtctg gttcacaaga atcggtgctc tcctctgatt cttcttccac  118740
tataaagtct tccccgtccg atgattccgc gtcggaatcc cgaaattcaa ttacatccga  118800
tggcgtagac ccatcatcgt cgctatcgtc ttcaccacca tcatcagata cgtcacattc  118860
cagtgcgctc ctatgcaaag gaacattcgg cgcctcaatg aacccgtctt cccccccgagg  118920 gggtcgatgg gacacttcca ttaaagtagc gcgtaagcac tgcgtctggg tgggttgaag   118980
ctgtaacaat tcctcccagc acgctaacgt gggacgctgt ctggtgcgac ccattagata  119040
aaagtcgagg catatgcgcc gcaatcttcg tgaatctcgc gtgacgcgtc ccgacgactg  119100
tgcaatacat aaaaaaacac ggttgatgtc ctcaacgagc ctggccgggt ggatctccca  119160
acccggagta caaaacgcgc cggggccccg cgacgtatcc cggccgttca ggggtcctgg  119220
tgcagatcca tattccatct ttccgttaac atcaaccgat gccccgggtt ttgactcgga  119280
cgagtcgccc cgcgtagccg gtgaggtgca aaacatgtcc ttggggccgt agtaaccttt  119340
tcccttaaaa ccgactcgac gctgtcgcgt tatgaatcgg acgaaccctg cacaacaaaa  119400
cacacaccca aacgtttaca tctatgaata aggctacttg ggtaaaatgg caatggggga  119460
ttccggggcg ggagaccttc gattgggttg cctttataac accaaaaaaa gggggggggcc  119520
```

```
ccgtgtgttt ttttttatca cgtcaaatcg attttaaaaa gcctgccgct ccatttggaa 119580
tatatatatt ctgtgaaaag cccgcccaca ccccataaaa ccgcgacatc gcgggaacac 119640
gcgcgaacaa gaaactctct ctctttctct atatatatat atatatatat atatatatat 119700
agaaagaaag tgcgaacggt ggttggacac atgccaaaac atgaaaaccc atacagtgaa 119760
aaaacgggaa gtgcgaatgc agatcaaaag agtgtatccg attggcgtac accacagaca 119820
tgcggacgcc caatttaacc cccccccttt ttcacccccc caccccaccc cattccaccc 119880
caggaagtgc gaacgggttt acatgcctca gatatgaagt tcttcgactt gttttttgaat 119940 aaatttttt gtgattttct acaacggttt agagaattat ggttataaac atcggcgggg 120000
taccgcgccc cctccccatc ggcggggtac cgcgccccct ccccatcggc ggggtaccgc 120060 gcccccctccc catcggcggg gtaccgcgcc ccctccccat cggcgggta ccgcgccccc 120120 tccccatcgg cgggggtta cgtgaacacc acaaccccgt gtgtatttta tgggttatcg 120180
cgggcttcgt gccgcctgac ataatcgttg ggaggggtgg tggtgtatac gcttgttgat 120240
tgcgcgaacg taatgacgac ggagagggac ccaaacacac cgtcgacgtg catttgatta 120300
actagatgcc ggatgggtgg aaacaacccg tgttatataa gatgttttgc atgtgagaca 120360
accccaattg tgtttatgta tattatatat cgtctgtaga cacacgatga ttggttgtta 120420
tttaaacata tgtaaatgaa attcacatgt ctggtatccc ttgttatgat gttgtaaggt 120480
atgcggaaat agacaccggg cgtacatcgc caaccagcgg tctctcctta aacgcatact 120540
atggtccatg aacttcccgc ctcgagtctc gtccaatcac tacatcgtct tatcattaag 120600
aatatttaca cggtgacgac acggggagga aatatgcggt cgaggggggg gcacaacacg 120660
ttttaagtac tgttggaact ccctcaccaa ccgcaatcgc aatcctttga aggctgcgag 120720
agcgtttgga aaactcgggt acgtctaaat tcacccccagt gcgatggata cgccgccgat 120780
gcagcgctct acacccccaac gcgcgggggtc gcctgatact ttggagttaa tggacctgtt 120840
ggacgcggcc gcggcggccg ccgaacacag gccccgggtg gtcacctcga gtcagcctga 120900
cgatctacta tttggagaga acgggtcat ggtgggacgg gaacacgaga tcgtttcaat 120960
tccctccgta tcgggacttc aaccagaacc cagaacggaa gatgttggcg aagagctaac 121020
acaagacgac tacgtatgcg aggacggtca ggatctaatg ggctcgcctg taatcccgct 121080
ggccgaggtc ttccacaccc gattctcgga ggccggcgcg cgagaaccaa caggagccga 121140 tcgctcccctt gagacagtct ctctcggaac gaagcttgct aggtctccaa aaccaccgat 121200
gaacgatggg gaaacgggca gaggtacgac ccctccgttc ccgcaggcct tctcccctgt 121260 atccccgcg tctcctgttg gagacgccgc cgggaacgat caacgggaag accagcggtc 121320
tataccccga caaacgacga gaggaaattc accaggtttg ccgtcggtgg tccatcgaga 121380
cagacaaact cagtccatct cgggtaaaaa gccgggcgat gagcaagcgg gtcatgcgca 121440
tgcatcgggg gacggagtag ttctccagaa aactcaacgg cccgctcagg gaaagagccc 121500
gaagaaaaag actttgaagg ttaaggtccc actcccggcg cggaaacccg gtggacctgt 121560
acccggcccg gttgagcaat tgtaccacgt cctttcggac agcgttcccg ctaagggggc 121620
aaaggcggac ctgccgtttg agaccgatga taccgcccca aggaaacatg atgcccgggg 121680
tataacacct cgcgtccctg gacgttcgtc gggggggcaaa cctagagcgt ttttggccct 121740
gccgggaaga tccacgcac cagacccgat tgaggatgac agcccagtgg agaaaaagcc 121800
aaagagtcgt gagtttgttt cgtcttcatc ctcttcctcg tcgtggggat cgtcatcgga 121860
```

-continued

```
ggatgaagac gatgaacccc ggcgcgtttc ggtgggaagt gaaactacag gcagcaggtc   121920
cggacgcgaa cacgccccct ccccgtcaaa ttcggatgat tcggactcaa atgatggtgg   121980
gtcgacgaaa caaaatatcc aaccgggata tcgatccatc agcggtcccg atccgaggat   122040
tcgtaagacc aaacgtcttg cgggggaacc ggggcgccag agacagaaat catttttccct  122100 gccgcgatcc agaaccccga taattccccc ggtgtcgggg ccgctcatga tgcccgacgg   122160
aagcccttgg cccggatcgg caccccctccc atccaacagg gtgcggtttg gaccgtccgg  122220
ggagaccaga gagggtcact gggaggatga ggctgtgaga gcggcgcggg ctcgttacga   122280
ggcctcaacg gaacccgtgc cgctttacgt gccggagttg ggagatccgg ctagacagta   122340
ccgcgcgctg attaacctga tctactgtcc agacagagac cctatagcat ggctccagaa   122400
ccccaagctg accggtgtca actcggccct gaaccagttc taccaaaagc tgttgccacc   122460
gggacgggcg ggtaccgccg ttacggggag cgtagcgtct cccgttccgc atgtaggcga   122520
agccatggcc acgggggagg ccctctgggc tctcccccac gcggccgcgg ccgtggctat   122580
gagccgtcga tacgaccggg cccaaaaaca ctttatccta cagagtctcc gcagagcctt   122640
tgccagcatg gcataccccg aggcaacggg ctccagtccg gcggcgcgga tctcccgcgg   122700
tcacccttct ccaacaaccc cggccacaca ggctcccgac cctcagccgt cggccgccgc   122760
acgctctctt tctgtgtgtc caccggatga tcgtttacga actccgcgca agcgcaagtc   122820
ccagccagtc gagagcagaa gcctcctcga caagattagg gagacacccg tcgcggacgc   122880
ccgggttgca gacgatcatg tggttttccaa ggccaagagg cgggtatccg agcccgtgac  122940
catcacctcg ggccctgtgg tggatccccc cgccgtaata acgatgccac ttgacggacc   123000 ggcccccaaac gggggatttc ggcgtattcc ccggggggcc ctgcataccc cggtcccgtc   123060
ggaccaggct cgcaaggcgt actgtacccc cgaaaccatc gcccgtctgg tcgacgaccc   123120
attgtttccc acggcctggc gccctgcgct aagctttgat cccggcgcct ggcggaaat    123180 cgccgctcgg cgtccgggcg gaggagaccg acggtttggt ccacccagcg gagtggaggc   123240
gctgcgacgg aggtgcgcct ggatgcggca gatcccagac ccggaggatg tgaggcttct   123300
gatcatctac gatccgttgc ccggagagga catcaacggc cccctcgaga gcaccctcgc   123360
gacagatccg ggaccgtcat ggagtccatc ccgagggggga ctgtctgtgg tcctggcagc   123420
cctgagtaac cggttgtgcc tgccgagcac tcatgcctgg gccgggaact ggaccggccc   123480
gccggacgtg tccgctttga acgcccgggg cgtttttatta ctgtcgaccc gagacctggc   123540 cttttgccggg gccgtcgagt atctaggctc gcggttggcc tctgcccggc gccggttgct   123600
ggtgttggac gcggtggccc tcgagaggtg gcccagggat ggaccgcctt tgtctcagta   123660
tcacgtgtac gtccgggccc cggcgcgacc ggacgcccag gccgtcgtcc gatggccaga   123720
ctcggcggtc acagaaggac tcgcccggcc cgtgtttgca tcgtcgcgca cctttgggcc   123780
agcgagtttt gctcgtatcg agactgcgtt tgccaacctg tacccgggcg aacaaccccct  123840 gtgtttgtgc cgcggtggga acgtcgcata caccgtgtgt acccgcgcgg gccccaagac   123900
ccgcgtcccc ctgtcgcccc gtgaataccg gcagtacgtg ctgccgggtt ttgacggttg   123960
caaggacctc gcgcgacagt ctcggggtct ggggctcggg gcagccgact ttgtggacga   124020
ggcggcacat agccaccgcg cagcaaaccg atggggcctg ggtgccgcgc ttcgacccgt   124080
cttccttccc gagggacgga gaccgggggc cgcggggccg gaggcggcg acgtacccac    124140 ctgggcgagg gtgttttgcc gccacgccct gctggaaccc gaccctgccg cagaaccact   124200
cgtgcttcca cccgtggccg gtcggtcggt ggcgctgtat gcgtcggcgg acgaggctcg   124260
```

```
gaatgccctc cccccgattc ccagagtaat gtggccgccc ggttttgggg ccgcggagac    124320
ggtgttggag gggagcgacg gaacacggtt cgtgttcgga caccacgggg gctcggaacg    124380
gccgtcagaa acccaggcgg ggcgacagcg gcgcaccgca gacgacagag aacacgcttt    124440
ggagctggac gattgggagg tggggtgtga agacgcgtgg gacagcgagg aggggggcgg    124500
ggacgacggg gacgcaccgg ggtcatcctt tggggtgagc atcgtgtcgg tggccccggg    124560
tgtgctgcga gaccgccggg tgggtttgcg cccggcggtc aaggtggagc tgttgtcctc    124620
gtcctcgtcc tccgaggacg aggacgatgt gtggggaggg cgcggggggg ggagccccc    124680 gcagagtcgg gggtgacgga gtccctcct tttctcgtga gcgccactgg cgcgcggact    124740
gtttgttgtt aataaaagcg gaacggtttt tatgaaaaaa gtgtctgtct gtctgtgcgg    124800
gcgggcgacg ggcgggctgg tcggaccccc ccccgaaaat aaccccccc cggtttctgg    124860 gcgcccggcg gaccccggga gagg                                          124884
```

<210> SEQ ID NO 77
<211> LENGTH: 12
<212> TYPE: DNA
<213> ORGANISM: Varicella zoster

<400> SEQUENCE: 77
ctgcagatag tt                                                             12

<210> SEQ ID NO 78
<211> LENGTH: 4
<212> TYPE: PRT
<213> ORGANISM: Varicella zoster

<400> SEQUENCE: 78

Leu Gln Ile Val
1

<210> SEQ ID NO 79
<211> LENGTH: 12
<212> TYPE: DNA
<213> ORGANISM: Varicella zoster

<400> SEQUENCE: 79
ctgcagatga ta                                                             12

<210> SEQ ID NO 80
<211> LENGTH: 4
<212> TYPE: PRT
<213> ORGANISM: Varicella zoster

<400> SEQUENCE: 80

Leu Gln Met Ile
1